(12) United States Patent
Druley et al.

(10) Patent No.: US 11,149,305 B2
(45) Date of Patent: Oct. 19, 2021

(54) DETECTION OF RARE SEQUENCE VARIANTS, METHODS AND COMPOSITIONS THEREFOR

(71) Applicant: Washington University, St. Louis, MO (US)

(72) Inventors: Todd E. Druley, St. Louis, MO (US); Andrew Young, St. Louis, MO (US)

(73) Assignee: Washington University, St. Louis, MO (US)

( * ) Notice: Subject to any disclaimer, the term of this patent is extended or adjusted under 35 U.S.C. 154(b) by 1053 days.

(21) Appl. No.: 15/545,437

(22) PCT Filed: Jan. 22, 2016

(86) PCT No.: PCT/US2016/014559
§ 371 (c)(1),
(2) Date: Jul. 21, 2017

(87) PCT Pub. No.: WO2016/118883
PCT Pub. Date: Jul. 28, 2016

(65) Prior Publication Data
US 2018/0002747 A1    Jan. 4, 2018

Related U.S. Application Data

(60) Provisional application No. 62/106,967, filed on Jan. 23, 2015.

(51) Int. Cl.
| | |
|---|---|
| *C12P 19/34* | (2006.01) |
| *C12Q 1/6858* | (2018.01) |
| *C12Q 1/6886* | (2018.01) |
| *C12Q 1/6855* | (2018.01) |
| *C12Q 1/6869* | (2018.01) |
| *C12Q 1/6883* | (2018.01) |

(52) U.S. Cl.
CPC ......... *C12Q 1/6858* (2013.01); *C12Q 1/6855* (2013.01); *C12Q 1/6869* (2013.01); *C12Q 1/6883* (2013.01); *C12Q 1/6886* (2013.01); *C12Q 2600/156* (2013.01)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS

2015/0031559 A1* 1/2015 Casbon ................ C12Q 1/6869
506/4

OTHER PUBLICATIONS

Casbon, J. et al., "A method for counting PCR template molecules with application to next-generation sequencing," Nucl. Acids Res., Apr. 13, 2011, pp. 1-8, vol. 39, No. 12, e81.
Flaherty, P. et al., "Ultrasensitive detection of rare mutations using next-generation targeted resequencing," Nuc. Acids Res., 2012, pp. 1-12, vol. 40, No. 1.
Forshew, T. et al., "Noninvasive Identification and Monitoring of Cancer Mutations by Targeted Deep Sequencing of Plasma DNA," Sci. Transl. Med., May 30, 2012, pp. 1-12, vol. 4, No. 136, 136ra68.
Fu, G. et al., Molecular indexing enables quantitative targeted RNA sequencing and reveals poor efficiencies in standard library preparations, PNAS, Feb. 4, 2014, pp. 1891-1896, vol. 111, No. 5.
Godley, L. et al., "Therapy-related Myeloid Leukemia," NIH Public Access Author Manuscript, available in PMC Aug. 1, 2009, pp. 1-20, Published in final edited form as: Semin. Oncol., Aug. 2008, pp. 418-429, vol. 35, No. 4.
Hiatt, J. et al., "Single molecule molecular inversion probes for targeted, high-accuracy detection of low-frequency variation," Genome Res., 2013, pp. 843-654, vol. 23, Cold Spring Harbor Laboratory Press.
Holstege, H. et al., "Somatic mutations found in the healthy blood compartment of a 115-yr-old woman demonstrate oligoclonal hematopoiesis," Genome Res., 2014, pp. 733-742, vol. 24, Cold Spring Harbor Laboratory Press.
Hourigan, C. et al., "Minimal Residual Disease in Acute Myeloid Leukemia," NIH Public Access Author Manuscript, available in PMC Sep. 15, 2014, pp. 1-24, Published in final edited form as: Nat. Rev. Clin. Oncol., Aug. 2013; pp. 460-471, vol. 10, No. 8.
Illumina Inc., "TruSight Tumor Sample Preparation Guide," Part #15042911, Rev. A, May 2013, pp. 1-52.
International Search Report and Written Opinion dated Apr. 28, 2016 from related PCT Application No. PCT/US2016/014559, 13 pgs.
Jabara, C. et al., "Accurate sampling and deep sequencing of the HIV-1 protease gene using a Primer ID," PNAS, Dec. 13, 2011, pp. 20166-20171, vol. 108, No. 50.
Kinde, I. et al., "Detection and quantification of rare mutations with massively parallel sequencing," PNAS, Jun. 7, 2011, pp. 9530-9535, vol. 108, No. 23.
Kohlmann, A. et al., "Monitoring of residual disease by next-generation deep-sequencing of RUNX1 mutations can identify acute myeloid leukemia patients with resistant disease," Leukemia, 2014, pp. 129-137, vol. 28, Macmillan Publishers Limited.
Langmead, B. et al., "Fast gapped-read alignment with Bowtie 2," Nat. Methods, Apr. 2012, pp. 357-359, vol. 9, No. 4, with Online Methods, 1 pg.
Ley, T. et al., "Genomic and Epigenomic Landscapes of Adult De Novo Acute Myeloid Leukemia," N. Engl. J. Med., May 30, 2013; pp. 2059-2074, vol. 368, No. 22.
Li, H. et al., "The Sequence Alignment/Map format and SAMtools," Bioinformatics, 2009, pp. 2078-2079, vol. 25, No. 16.

(Continued)

*Primary Examiner* — Frank W Lu
(74) *Attorney, Agent, or Firm* — Polsinelli PC

(57) ABSTRACT

The present disclosure encompasses methods of error corrected sequencing (ECS) that enable detection of very rare mutations well below the error rate of convention next generation sequencing (NGS). Further, the methods disclosed herein enable multiplex targeting of genomic DNA.

7 Claims, 42 Drawing Sheets
(20 of 42 Drawing Sheet(s) Filed in Color)
Specification includes a Sequence Listing.

(56) References Cited

OTHER PUBLICATIONS

Loman, N. et al., "Performance comparison of benchtop high-throughput sequencing platforms," Nat. Biotechnol., Advance Online Publication, 2012, pp. 1-6, with Online Methods, 2 pgs., Nature Publishing Group.

Lou, D. et al., "High-throughput DNA sequencing errors are reduced by orders of magnitude using circle sequencing," PNAS, Dec. 3, 2013, pp. 19872-19877, vol. 110, No. 49.

Miner, B. et al., "Molecular barcodes detect redundancy and contamination in hairpin-bisulfite PCR," Nuc. Acids Res., 2004, pp. 1-4, vol. 32, No. 17, e135.

Quail, M. et al., "SASI-Seq: sample assurance Spike-Ins, and highly differentiating 384 barcoding for Illumina sequencing," BMC Genomics, 2014, pp. 1-12, vol. 15, No. 110.

Salipante, S et al., "Detection of minimal residual disease in NPM1-mutated acute myeloid leukemia by next-generation sequencing," NIH Public Access Author Manuscript, available in PMC May 1, 2015, pp. 1-16, Published in final edited form as: Mod. Pathol., Nov. 2014, pp. 1438-1446, vol. 27, No. 11.

Schmitt, M. et al., Detection of ultra-rare mutations by next-generation sequencing, PNAS, Sep. 4, 2012, pp. 14508-14513, vol. 109, vol. 36.

Smith, E. et al., "Biased estimates of clonal evolution and subclonal heterogeneity can arise from PCR duplicates in deep sequencing experiments," Genome Biol., 2014, 1-10, vol. 15, No. 420.

Thorvaldsdottir, H. et al., "Integrative Genomics Viewer (IGV): high-performance genomics data visualization and exploration," Brief Bioinform., 2012, pp. 178-192, vol. 14, No. 2, Oxford University Press.

Untergasser, A. et al., "Primer3—new capabilities and interfaces," Nucl. Acids Res., Jun. 22, 2012, pp. 1-12, vol. 40, No. 15, e115.

Walter, M. et al., "Clonal Architecture of Secondary Acute Myeloid Leukemia," N. Engl. J. Med.,Mar. 22, 2012, pp. 1090-1098, vol. 366, No. 12.

Welch, J. et al., "The Origin and Evolution of Mutations in Acute Myeloid Leukemia," Cell,Jul. 20, 2012, pp. 264-278, vol. 150, Elsevier Inc.

Wong, T. et al., "The Role of TP53 Mutations in the Origin and Evolution of Therapy-Related AML," HHS Public Access Author Manuscript, available in PMC Aug. 26, 2015, pp. 1-23, Published in final edited form as: Nature, Feb. 26, 2015, pp. 552-555, vol. 518, No. 7540.

* cited by examiner

DETECTION OF RARE SEQUENCE VARIANTS, METHODS AND COMPOSITIONS THEREFOR

CROSS REFERENCE TO RELATED APPLICATIONS

This application claims the benefit PCT Application PCT/US2016/014,559, filed Jan. 22, 2016, which claims the benefit of U.S. Provisional Application No. 62/106,967, filed Jan. 23, 2015, the disclosures of which is hereby incorporated by reference in its entirety.

GOVERNMENTAL RIGHTS

This invention was made with government support under 1K08CA140720-01A1 awarded by the National Institutes of Health. The government has certain rights in the invention.

FIELD OF THE INVENTION

The present disclosure encompasses methods of error corrected sequencing (ECS) that enable detection of very rare mutations well below the error rate of conventional next generation sequencing (NGS). Further, the methods disclosed herein enable multiplex targeting of genomic DNA.

BACKGROUND OF THE INVENTION

Massively parallel next generation sequencing is a powerful tool for whole genome sequencing. Its low cost relative to prior methods and ease in automation allow for large scale analyses of large genomes or many samples with an error rate of 1%. For many sequencing applications, this is sufficient, however when searching for rare mutations in a heterogeneous population, this 1% error rate can confound the isolation of single base mutations in a small population of cells with technical sequencing errors. Detecting rare mutations at 2-5% variant allele fraction (VAF) using current methods requires costly and time-intensive deep resequencing, and lower-frequency variants are undetectable regardless of sequencing depth.

Several groups have tried to mitigate this problem through a variety of methods, including counting PCR amplicons (Casbon et al. 2011), large amounts of template and small numbers of cycles combined with statistical analyses (Flaherty et al. 2012), tagging of DNA molecules during initial PCR (Miner et al 2004, Jabara et al. 2011, Smith et al 2014 and Schmitt et al. 2012), and performing hybridization capture reactions in lieu of PCR (Hiatt et al 2013). The methods of Casbon and Flaherty require complex mathematical models on the current data and are unsuitable for high throughput applications.

Previous implementations of error-corrected next-generation sequencing (NGS) have limitations that have hampered their clinical applicability. First, some methods cannot be targeted and are not compatible with multiplexing, which limits their ability to handle mammalian-sized genomes (Lou et al., 2013; Schmitt et al., 2012). The method of Schmitt also hinges on obtaining sequencing reads of both strands of the same molecule. In theory, this would mean about half of the sequencing power would be lost due to pairing up of data strands, however, due to experimental limitations, nearly three quarters of the sequencing reads are not included in the data analyses. While this is acceptable for some applications, Illumina® sequencing methods are expensive and this method of error correction requires wasting resources on data that are never going to be analyzed.

Several other targeted methods require large amounts of starting material. Schmitt's method as described uses 3 µg of DNA isolated from a phage library in *Escherichia coli* for library preparation. Jabara used 10,000 RNA molecules from a single HIV strain. Kinde and colleagues (2011) used a DNA library from 100,000 cells to isolate rare mutations using low-efficiency two-dimensional capture arrays. Such amounts of template are not available for sequencing genomic DNA samples of limited quantity.

SUMMARY OF THE INVENTION

In an aspect, the disclosure provides a method of identifying a genetic mutation in a biological sample comprising nucleic acid obtained from a subject. The method comprises: (a) amplifying one or more regions of interest from the biological sample comprising nucleic acid, wherein a plurality of amplicons for each region of interest are generated; (b) attaching an adapter and a random component to each amplicon generated in (a) and amplifying; (c) sequencing the amplicons comprising the random component generated in (b), wherein redundant reads are generated and wherein the redundant reads are grouped by the random component and a consensus sequence is identified; and (d) comparing the consensus sequence to a reference sequence, wherein a consensus sequence that differs from the reference sequence comprises a genetic mutation.

In another aspect, the disclosure provides a method of identifying a genetic mutation in a biological sample comprising nucleic acid obtained from a subject. The method comprises: (a) hybridizing a primer pool comprising one or more primer pairs specific to one or more regions of interest from the biological sample comprising nucleic acid, extending from an upstream primer of the primer pair to a downstream primer of the primer pair, and ligating the extension product to the downstream primer of the primer pair, wherein products comprising the regions of interest flanked by sequences required for amplification are generated; (b) attaching an adapter comprising a random component and attaching an adapter comprising an index sequence to the products from (a) and amplifying; (c) sequencing the products comprising the random component generated in (b), wherein redundant reads are generated and wherein the redundant reads are grouped by the random component and a consensus sequence is identified; and (d) comparing the consensus sequence to a reference sequence, wherein a consensus sequence that differs from the reference sequence comprises a genetic mutation.

In still another aspect, the disclosure provides a method of detecting minimal residual disease (MRD) in a subject. The method comprises: (a) hybridizing a primer pool comprising one or more primer pairs specific to one or more regions of interest from a biological sample comprising nucleic acid obtained from the subject, extending from an upstream primer of the primer pair to a downstream primer of the primer pair, and ligating the extension product to the downstream primer of the primer pair, wherein products comprising the regions of interest flanked by sequences required for amplification are generated; (b) attaching an adapter comprising a random component and attaching an adapter comprising an index sequence to the products from (a) and amplifying; (c) sequencing the products comprising the random component generated in (b), wherein redundant reads are generated and wherein the redundant reads are grouped by the random component and a consensus sequence is identified; and (d) comparing the consensus sequence to a reference sequence, wherein a consensus sequence that differs from the reference sequence comprises a genetic mutation and is indicative of MRD.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A, FIG. 1B) DNA extracted from a diagnostic leukemia sample with known mutations in RUNX1 (FIG. 1A) and IDH2 (FIG. 1B) was serially diluted into non-cancer, unrelated human DNA. Two replicates were run per sample/dilution. The coefficient of determination ($r^2$) between diluted tumor concentration in the sample and VAF in the generated read families was 0.9999 and 0.9991 for RUNX1 and IDH2, respectively. (FIG. 1C) The VAF at every nucleotide not expected to contain mutations in the dilution series experiment were analyzed to determine the error profile of the error-corrected consensus sequences compared with conventional deep sequencing. A cumulative distribution function of VAF demonstrated a reduced error profile in read families relative to conventional deep sequenced reads. (FIG. 1D) The most frequent class of substitution seen in read families was in G to T (C to A) transversions, which was consistent with oxidative conversion of guanine to 8-oxo-guanine. (FIGS. 1E, 1F) The leukemia-specific variants identified in ASXL1 and U2AF1 at diagnosis (circled) were not distinguishable from sequencing errors in the same substitution class by conventional deep sequencing. (FIGS. 1G, 1H) Targeted error-corrected sequencing identified the ASXL1 variant in the 2002 banked sample at 0.004 VAF and the U2AF1 variant in the 2004 banked sample at 0.009 VAF.

FIG. 5A is samples from 2002 and FIG. 5C is samples from 2004. Correcting the sequencing errors with ECS clearly identified the ASXL1 variant at 0.0042 VAF in 2002 (FIG. 5D), 0.092 VAF in 2003 (FIG. 5E) and 0.029 VAF in 2004 (FIG. 5F).

FIG. 6A is samples from 2002 and FIG. 6C is samples from 2004. Correcting the sequencing errors with ECS did not identify the U2AF1 variant in 2002 (FIG. 6D), but did identify the U2AF1 variant at 0.031 VAF in 2003 (FIG. 6E) and 0.0089 VAF in 2004 (FIG. 6F).

FIG. 9A depicts (a) the annealing of primers to genomic DNA, (b) single strand extension, and (c) ligation. FIG. 9B depicts (d) the newly minted single-stranded amplicon after capture, (e) attachment of an adapter with a sample-specific index (fixed) via PCR, (f) attachment of an adapter with an ECS index (random) via PCR, and (g) amplifying of this molecule to make read families.

FIG. 10A shows to libraries sequenced on the same run with an $R^2$ of 0.9718 and FIG. 10B shows two libraries sequenced on different runs with an $R^2$ of 0.7536.

FIG. 15A shows the detected rare variants by function of which the majority are exonic. FIG. 15B shows the detected exonic rare variants by function of which the majority are nonsynonymous SNVs.

FIG. 18A shows the histogram coverage per amplicon. FIG. 18B show the histogram coverage per amplicon with variants called.

FIG. 19A shows the exonic mutations per target space in the panel. FIG. 19B shows the intronic mutations per target space in the panel.

FIG. 25A shows that VAF measured by ECS is highly correlated with VAF measured by ddPCR ($R^2$=0.98). FIG. 25B shows that even when specifically focusing on a VAF of <0.01, ECS and ddPCR still correlated ($R^2$=0.72).

DETAILED DESCRIPTION OF THE INVENTION

Figure 1A:
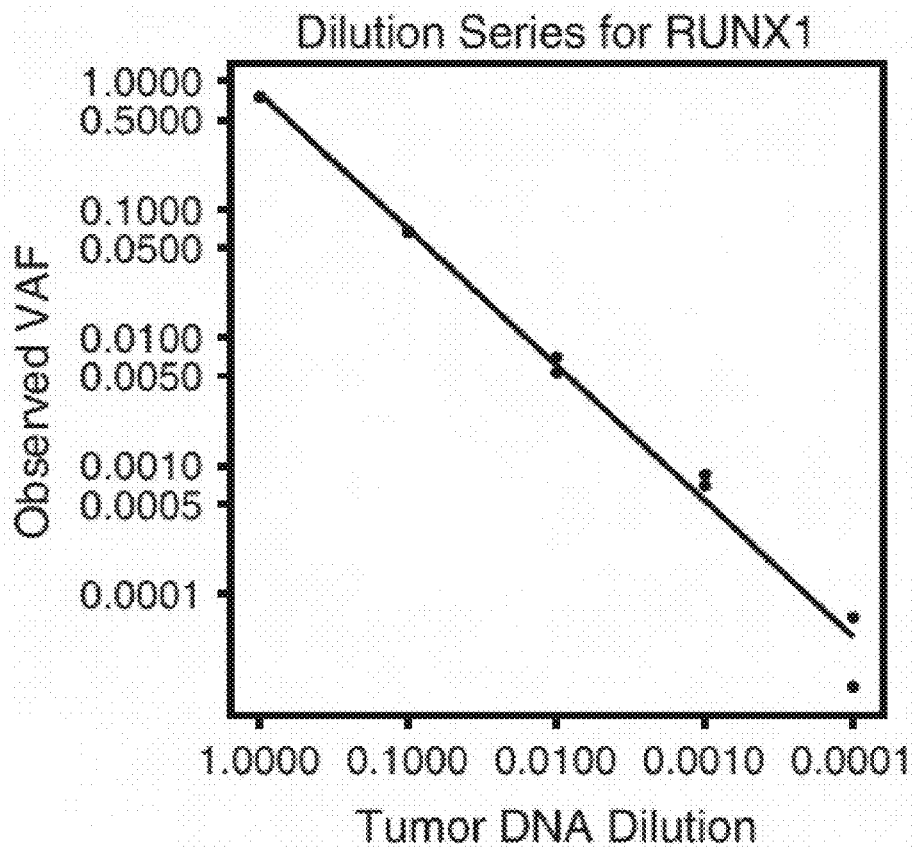
FIGS. 1A, 1B, 1C, 1D, 1E, 1F, 1G and 1H depict graphs showing benchmarking for ECS and the identification of rare pre-leukemic mutations.

The present inventors have developed sequencing methods for identification of rare mutations. Methods of present disclosure can be used to quantify rare somatic mutations, such as, for example, DNA from clinical specimens. Importantly, the limit of detection for the disclosed method is at least two orders of magnitude below the error rate of the Illumina® sequencing platform performed by standard methods.

In various embodiments, methods of the present disclosure involve PCR amplification of multiple regions of interest in the genome, attaching adaptors comprising a random component and/or index sequences to the amplified DNA, performing sequencing, creating read families of the same index sequence and comparing reads in the same family. By these methods, true variations in the sequence can be distinguished from technical artifacts.

The methodology disclosed herein is described in greater detail below.

(a) Sample Preparation

The disclosure encompasses a method of identifying a rare sequence in a sample comprising nucleic acid. In an embodiment, the disclosure encompasses a method of identifying a genetic mutation in a sample comprising nucleic acid. Specifically, the disclosure encompasses a method of identifying a genetic mutation in a biological sample comprising nucleic acid obtained from a subject. A first iteration of the method may be used to query about 1 to about 20 genomic loci (e.g. region of interest). A second iteration of the method may be used to query about 1 to about 600 or more genomic loci.

A region of interest may be any nucleic acid amenable to standard PCR. Non-limiting examples of a region of interest may be a nucleic acid used to identify a rare mutation or low levels associated with drug-resistance, graft rejection, residual disease, tumors, immune diseases, fetal DNA, and microbial infection or contamination. With respect to microbial infection or contamination, a region of interest may be a nucleic acid used to identify a bacterial strain. It is known in the art that 16S nucleic acid is a good, widely used nucleic acid to identify a bacterial strain. In an embodiment, the primer pair comprises sequences complementary to a 16S nucleic acid sequence. In another embodiment, the region of interest may be one or more nucleic acids used to diagnose cancer, wherein a mutation within that region of interest is indicative of cancer. Specifically, the region of interest may be one or more nucleic acids used to diagnose leukemia. For example, the region of interest may be any nucleic acid known to be mutated in leukemia.

The sample comprising nucleic acid may be a sample from a subject, the environment, a laboratory, or any sample in which nucleic acid is present. When the sample is from a subject, the sample may be from stool, sputum, urine, plasma, peripheral blood, serum, bone marrow, tissue, and other bodily fluids. The tissue sample may be a tissue biopsy. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may be used "as is" or the nucleic acid may be purified from the sample prior to sample preparation.

The subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

i. First Iteration

In an aspect, a method of the disclosure comprises, in part, amplifying one or more regions of interest from a biological sample comprising nucleic acid. The amplification generates a plurality of amplicons for each region of interest.

Amplification takes place in the presence of one or more primer pairs. A first primer of the primer pair comprises a sequence complementary to an upstream portion of the region of interest and a second primer of the primer pair comprises a sequence complementary to a downstream portion of the region of interest. The primer pairs are designed to anneal to complementary strands of nucleic acid (i.e. on primer of the primer pair anneals to the sense strand and one primer of the primer pair anneals to the antisense strand). The complementary sequence may be altered based on the region of interest to be amplified. The complementary sequences of the primer pair may comprise about 10 to about 100 nucleotides complementary to the region of interest. For example, the complementary sequences of the primer pair may comprise about 15 to about 50 nucleotides complementary to the region of interest. In an embodiment, the complementary sequences of the primer pair may comprise about 20 to about 40 nucleotides complementary to the region of interest. In another embodiment, the complementary sequences of the primer pair may comprise about 20 to about 35 nucleotides complementary to the region of interest.

One or more primer pairs is contacted with a sample comprising nucleic acid. Nucleic acid may be, for example, RNA or DNA. Modified forms of RNA or DNA may be used. In an exemplary embodiment, the nucleic acid is genomic DNA. The amount of nucleic acid in the sample may be about 200 to about 1000 ng or more. For example, the amount of nucleic acid in the sample may be about 400 to about 800 ng. In certain embodiment, the amount of nucleic acid in the sample is about 200 ng, about 300 ng, about 400 ng, about 500 ng, about 600 ng, about 700 ng, about 800 ng, about 900 ng or about 1000 ng or more. In some embodiments, the amount of nucleic acid in the sample may be about 1 µg, about 5 µg, about 10 µg, about 20 µg, about 30 µg, about 40 µg, or about 50 µg. It is important to note that as the amount of nucleic acid increases, the amount of random components (described below) must proportionally increase to ensure that the same random component is not utilized twice. A person of skill in the art would understand how to scale the methodology based on the amount of nucleic acid used.

In general, amplification of the region of interest is carried out using polymerase chain reaction (PCR). A PCR reaction may comprise sample comprising nucleic acid, one or more primer pairs, polymerase, water, buffer, and deoxynucleotide triphosphates (dNTPs) in a single reaction vial. PCR may be performed according to standard methods in the art. By way of non-limiting example, the PCR reaction may comprise denaturation, followed by about 15 to about 30 cycles of denaturation, annealing and extension, followed by a final extension. In an exemplary embodiment, the PCR reaction comprises denaturation at about 98° C. for about 30 seconds, followed by about 15 to about 30 cycles of (about 98° C. for about 10 seconds, about 62-72° C. for about 30 seconds, about 72° C. for about 30 seconds), followed by a final extension at about 72° C. for about 2 minutes.

In certain embodiments, a single reaction vial is used per primer pair. In other embodiments, a single reaction vial comprises more than one primer pair such that more than one region of interest is amplified per reaction vial. More specifically, amplification of a region of interest may be multiplexed. Accordingly, a single reaction comprises primer pairs sufficient to amplify about 1-5, about 5-10, about 10-15, or about 15-20 regions of interest. In other embodiments, a single reaction comprises primer pairs sufficient to amplify 2, 3, 4, 5, 6, 7, 8, 9, 10, 11, 12, 13, 14, 15, 16, 17, 18, 19, or 20 regions of interest.

In a different embodiment, a single reaction vial may comprise more than one primer pair and the amplification may be carried out for about 10-20 cycles, or about 15-20 cycles. Then, the amplicons may be separated into more than one reaction vial, one primer pair is then added to each reaction vial, and the reaction may be carried out for an additional about 10-20 cycles, or about 15-20 cycles.

Optionally, the amplicons may be purified prior to attaching an adapter, random component, and/or index sequence (described below in Section 1(b)). Methods of purifying amplicons are known in the art. For example, AMPure bead cleanup may be used.

ii. Second Iteration

In an aspect, a method of the disclosure comprises, in part, hybridizing a primer pool comprising one or more primer pairs specific to one or more regions of interest from the biological sample comprising nucleic acid, extending from an upstream primer of the primer pair to a downstream primer of the primer pair, and ligating the extension product to the downstream primer of the primer pair. The hybridization, extension and ligation generates products comprising the regions of interest flanked by sequences required for amplification.

The primer pool comprises one or more primer pairs designed to anneal to the same strand of nucleic acid. A first primer of the primer pair comprises a sequence complementary to an upstream portion of the region of interest and a second primer of the primer pair comprises a sequence complementary to a downstream portion of the region of interest. The complementary sequence may be altered based on the region of interest to be amplified. The complementary sequences of the primer pair may comprise about 10 to about 100 nucleotides complementary to the region of interest. For example, the complementary sequences of the primer pair may comprise about 15 to about 50 nucleotides complementary to the region of interest. In an embodiment, the complementary sequences of the primer pair may comprise about 20 to about 40 nucleotides complementary to the region of interest. In another embodiment, the complementary sequences of the primer pair may comprise about 20 to about 35 nucleotides complementary to the region of interest. In an exemplary embodiment, the primer pool is the TruSight® Myeloid Sequencing Panel (Illumina).

The primer pool is contacted with a sample comprising nucleic acid. Nucleic acid may be, for example, RNA or DNA. Modified forms of RNA or DNA may be used. In an exemplary embodiment, the nucleic acid is genomic DNA. The amount of nucleic acid in the sample may be about 200 to about 1000 ng or more. For example, the amount of nucleic acid in the sample may be about 400 to about 800 ng. In certain embodiment, the amount of nucleic acid in the sample is about 200 ng, about 300 ng, about 400 ng, about 500 ng, about 600 ng, about 700 ng, about 800 ng, about 900 ng or about 1000 ng or more. In some embodiments, the amount of nucleic acid in the sample may be about 1 µg, about 5 µg, about 10 µg, about 20 µg, about 30 µg, about 40 µg, or about 50 µg. It is important to note that as the amount of nucleic acid increases, the amount of random components (described below) must proportionally increase to ensure that the same random component is not utilized twice. A person of skill in the art would understand how to scale the methodology based on the amount of nucleic acid used.

Hybridization of the primer pool to the nucleic acid may be done via methods standard in the art. For example, the primer pool and nucleic acid may be incubated at elevated temperature for about 1 to about 2 hours. More specifically, the primer pool and nucleic acid may be incubated at about 95° C. for about 1 minute and then the temperature may be allowed to decrease to about 40° C. for about 80 minutes.

Following hybridization, a polymerase extends from the upstream primer through the region of interest, followed by ligation to the 5' end of the downstream primer using ligase. This process results in the formation of products comprising the regions of interest flanked by sequences required for amplification. If the nucleic acid is DNA, the polymerase may be any suitable DNA polymerase known in the art.

Further, if the nucleic acid is DNA, the ligase may be any suitable DNA ligase known in the art. Extension and ligation may be carried out via methods standard in the art and dependent upon the polymerase and ligase utilized. For example, extension and ligation may be conducted at about 37° C. for about 45 minutes.

Optionally, following hybridization, the unbound primers may be washed away prior to proceeding to the extension and ligation step. Methods of washing away unbound primers are known in the art.

A single reaction vial comprises the entire primer pool such that more than one region of interest per reaction vial may be amplified downstream in the method. More specifically, the method enables multiplex targeting from genomic DNA. Accordingly, a single reaction comprises primer pairs sufficient to hybridize to about 1-5 or about 5-10, about 10-20, about 20-30, about 30-40, about 40-50, about 50-60, about 60-70, about 70-80, about 80-90, about 90-100, about 100-150, about 150-200, about 200-250, about 250-300, about 300-350, about 350-400, about 400-450, about 450-500, about 500-550, about 550-600, about 600-700, about 700-800, about 800-900, or about 900-1000 regions of interest. Alternatively, a single reaction comprises primer pairs sufficient to hybridize to more than 100, more than 150, more than 200, more than 250, more than 300, more than 350, more than 400, more than 450, more than 500, more than 550, more than 600, more than 650, more than 700, more than 750, more than 800, more than 850, more than 900, more than 950, more than 1000, more than 1050, more than 1100, more than 1150, more than 1200, more than 1250, more than 1300, more than 1350, more than 1400, more than 1450, more than 1500, more than 1550, more than 1600, more than 1650, more than 1700, more than 1750, more than 1800, more than 1850, more than 1900, more than 1950, or more than 2000 regions of interest. In certain embodiments, a single reaction comprises primer pairs sufficient to hybridize to about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1550, about 1600, about 1650, about 1700, about 1750, about 1800, about 1850, about 1900, about 1950, or about 2000 regions of interest. In other embodiments, a single reaction comprises primer pairs sufficient to hybridize to about 5, about 10, about 15, about 20, about 25, about 30, about 35, about 40, about 45, about 50, about 55, about 60, about 65, about 70, about 75, about 80, about 85, about 90, about 95, or about 100 regions of interest. In still other embodiments, a single reaction comprises primer pairs sufficient to hybridize to about 500, about 510, about 515, about 520, about 525, about 530, about 535, about 540, about 545, about 550, about 555, about 560, about 565, about 570, about 575, about 580, about 585, about 590, about 595, or about 600 regions of interest.

(b) Error-Corrected Sequencing Library Preparation

A method of the disclosure comprises, in part, attaching an adapter, random component, and/or index sequence to each amplicon or product generated in Section 1(a).

As used herein, an "adapter" is a sequence that permits universal amplification. A key feature of the adapter is to enable the unique amplification of the amplicon or product only without the need to remove existing template nucleic acid or purify the amplicons or products. This feature enables an "add only" reaction with fewer steps and ease of automation. The adapter is attached to the 5' and 3' end of the amplicon or product. The adapter may be Y-shaped, U-shaped, hairpin-shaped, or a combination thereof. In a specific embodiment, the adaptor is Y-shaped. In an exemplary embodiment, the adapter may be an Illumina adapter for Illumina sequencing.

As used herein, a "random component" is composed of random nucleotides to generate a complexity of random components far greater than the number of unique amplicons or products to be sequenced. This ensures that having the same random component attached to multiple amplicons or products is an extremely statistically improbable event. A random component may also be referred to as a barcode. The random component design can theoretically generate $9.1 \times 10^8$ to $1.4 \times 10^{10}$ unique random components. This complexity can easily be expanded by increasing the length of the random regions in the random component. In an embodiment, the random component may be about 5 to about 100 nucleotides. In another embodiment, the random component may be about 10 to about 25 nucleotides. For example, the random component may be about 15 to about 20 nucleotides. In still another embodiment, the random component is about 16 to about 18 nucleotides. Accordingly, the random component may be 10, 11, 12, 13, 14, 15, 16, 17, 18, 19, 20, 21, 22, 23, 24 or 25 or more nucleotides. The random component is attached to the 5' or 3' end of the amplicon or product. In a specific embodiment, the random component is attached to the 5' end of the amplicon or product.

In addition to a random component and an adapter, an index sequence may also be attached to each amplicon or product generated. The addition of an index sequence allows pooling of multiple samples into a single sequencing run. This greatly increases experimental scalability, while maintaining extremely low error rates and conserving read length. The index sequence may be about 5 to about 10 nucleotides. Accordingly, the index sequence may be 5, 6, 7, 8, 9 or 10 or more nucleotides. In an embodiment, the index sequence is about 6 nucleotides.

In a specific embodiment, an adapter, a random component and an index sequence are attached to each amplicon or product. In an embodiment, a nucleotide sequence comprising an adaptor and a random component is attached to the 5' end of each amplicon or product and a nucleotide sequence comprising an adaptor and an index sequence is attached to the 3' end. In another embodiment, a nucleotide sequence comprising an adaptor and a random component is attached to the 3' end of each amplicon or product and a nucleotide sequence comprising an adaptor and an index sequence is attached to the 5' end. In still another embodiment, a nucleotide sequence comprising an adaptor, a random component and an index sequence is attached to the 5' end and a nucleotide sequence comprising an adaptor is attached to the 3' end. In still yet another embodiment, a nucleotide sequence comprising an adaptor, a random component and an index sequence is attached to the 3' end and a nucleotide sequence comprising an adaptor is attached to the 5' end. In an exemplary embodiment, a nucleotide sequence comprising SEQ ID NO:1 is attached to each amplicon or product at the 5' end and a nucleotide sequence comprising SEQ ID NO:2 is attached to each amplicon or product at the 3' end. In another exemplary embodiment, a nucleotide sequence comprising SEQ ID NO:2 is attached to each amplicon or product at the 5' end and a nucleotide sequence comprising SEQ ID NO:1 is attached to each amplicon or product at the 3' end.

The nucleotide sequence comprising an adapter, a random component and/or an index sequence may be attached to the amplicon or product via methods known in the art. In certain embodiments, the nucleotide sequence comprising an adapter, a random component and/or an index sequence is ligated to an amplicon or product via methods standard in the art. For example, the nucleotide sequence is annealed at about 95° C. for about 5 minutes, then the temperature is decreased by about 1° C., about every 30 seconds until about 4° C. Enrichment of the properly ligated products is then carried out. Methods of enriching properly ligated products are known in the art. For example, PCR amplification is carried out using the ligation product and appropriate primers. In an exemplary embodiment, the PCR is carried out as follows: about 98° C. for about 30 seconds, followed by about 6 cycles of about 98° C. for about 10 seconds, about 57° C. for about 30 seconds, and about 72° C. for about 30 seconds, finishing with an extension at about 72° C. for about 2 minutes.

In other embodiments, the nucleotide sequence comprising an adapter, a random component and/or an index sequence is attached to an amplicon or product via PCR. For example, the amplicon or product may be contacted with a nucleotide sequence comprising an adaptor and an index sequence and a PCR reaction is conducted. Then, this product is contacted with a nucleotide sequence comprising an adaptor and a random component and a PCR reaction is conducted. The resulting product is a nucleotide sequence comprising an adaptor, a random component, a region of interest, an index sequence and a downstream adaptor. Alternatively, the amplicon or product may be contacted with a nucleotide sequence comprising an adaptor and a random component and a PCR reaction is conducted. Then, this product is contacted with a nucleotide sequence comprising an adaptor and an index sequence and a PCR reaction is conducted. The resulting product is a nucleotide sequence comprising an adaptor, an index sequence, a region of interest, a random component and a downstream adaptor.

The products or amplicons comprising an adapter, a random component and/or an index sequence are then subjected to exponential PCR. In an embodiment, an exponential PCR reaction may comprise the products or amplicons comprising an adapter, a random component and/or an index sequence, primers, polymerase, water, buffer, and deoxynucleotide triphosphates (dNTPs) in a single reaction vial. Exponential PCR may be performed according to standard methods in the art. By way of non-limiting example, the exponential PCR reaction may comprise denaturation, followed by about 15-30 cycles of denaturation, annealing and extension, followed by a final extension. In a specific embodiment, the exponential PCR reaction comprises denaturation at about 95° C. for about 3 minutes, followed by about 16-33 cycles of (about 95° C. for about 30 seconds, about 62-72° C. for about 30 seconds, about 72° C. for about 60 seconds), followed by a final extension at about 72° C. for about 5 minutes.

Upon performing exponential PCR, the products or amplicons comprising an adapter, a random component and/or an index sequence are amplified. The exponential PCR products comprise: an adapter, a random component, a region of interest, a downstream adapter and an index sequence.

Optionally, the products or amplicons comprising an adapter, a random component and/or an index sequence may be purified prior to exponential PCR. Methods of purifying products or amplicons are known in the art. For example, AMPure bead cleanup may be used.

(c) Error-Corrected Sequencing

A method of the disclosure comprises, in part, sequencing the exponential PCR product. According to the method of the disclosure, sequencing of the exponential PCR product generates redundant reads. The redundant reads are grouped by random component and a consensus sequence is identified such that the redundant reads mitigate sequence errors.

Sequencing may be performed according to standard methods in the art. Sequencing is preferably performed on a massively parallel sequencing platform, many of which are commercially available including, but not limited to Illumina, Roche/454, Ion Torrent, and PacBIO. In an exemplary embodiment, Illumina sequencing is used.

Reads may be separated by the index sequence and trimmed to remove primer sequences. Reads may be grouped by the random component. In certain embodiments, groups of reads with less than three, less than four, or less than 5 reads may be removed. To eliminate ambiguous sequences, the random components may be sorted by abundance and clustered at an identity of about 85%. Alternatively, the random components may be sorted by abundance and clustered at an identity of about 65% to about 95%. The random components may be clustered from most abundant to least abundant. Given that most sequencing errors are random and that the correct sequence should occur more often than a variant with sequencing errors, the abundance-weighted clustering provides a means to eliminate spurious random components that are most likely due to sequencing errors while retaining the more abundant (and most likely true positive) random components.

This redundant sequencing of each amplicon or product allows the error-correction of each amplicon or product. For example, a consensus sequence is generated for each random component group by scoring and weighing the nucleotide at each base position. Sequences with a consensus sequence that is identical to the most abundant sequence associated with the same random component are kept, this process is called quality filtering. Specifically, at every position, the nucleotides called by each sequence read are compared and a consensus nucleotide is called if there is at least about 90% agreement between the reads. If there is less than about 90% agreement, an "N" is called in the consensus sequence at that position.

The inventors demonstrated that the methodology disclosed herein was 99% specific to detect variants above 0.0034 VAF for G to T (C to A) substitutions, 0.00020 VAF for C to T (G to A) substitutions, and 0.000079 VAF for the other eight possible substitutions.

(d) Comparison to Reference Sequence

After an error-corrected consensus sequence (ECCS) has been identified, the ECCS may be compared to a reference sequence to determine the presence of one or more mutations. A reference sequence may be a sequence without any known mutations. A reference sequence without any known mutations may be referred to as a wild-type sequence. In certain embodiments, a reference sequence is a human sequence.

Comparison of the ECCSs to a reference sequence may identify clinically silent single nucleotide variations (SNVs). Specifically, the method disclosed herein may identify a genetic mutation that is present at a frequency of less than 1 in 1,000 in the sample (0.1%). For example, the method disclosed herein may identify a genetic mutation that is present at a frequency of less than 1 in 1,000, less than 1 in 2,000, less than 1 in 3,000, less than 1 in 4,000, less than 1 in 5,000, less than 1 in 6,000, less than 1 in 7,000, less than 1 in 8,000, less than 1 in 9,000, or less than 1 in 10,000 in the sample. In a specific embodiment, the method disclosed herein may identify a genetic mutation that is present at a frequency of less than 1 in 10,000 in the sample (0.01%).

II. Methods of Use

A method of the invention may be used to quantitate as well as to determine a sequence. For example, the relative abundance of two or more analyte nucleic acid fragments may be compared. A method of the invention may be used to identify rare mutants in a population of DNA templates, to measure polymerase error rates, or to judge the reliability of oligonucleotide synthesis. Additionally, a method of the invention may be used to diagnose, treat or prevent a disease in a subject. Identification of a rare mutation could facilitate the diagnosis of a disease, enable the proper methodology, such as a therapeutic, to treat the disease, or prevent the onset of disease by administration of prophylactic therapies. Still further, a method of the invention may be used to detect genetic mutations involved in cancer or other diseases, such as immune-mediated diseases. In another embodiment, a method of the invention may be used to identify and quantify a microbial infection of a subject. The knowledge gained may be used to assess the health of the subject. Further, a method of the invention may be used as a quality control measurement in clinical labs or in synthetic biology to determine microbial contamination.

The results described in the examples below describe a method of identifying ultra-rare pre-leukemic clones using the methodology described above. The methodology disclosed herein substantially improves the accuracy and depth of massively parallel sequencing. Thus, the methodology results in an assay to determine a VAF of 1:10,000 molecules in individuals at high depth with high precision. The methodology disclosed herein may be applied to virtually any sample preparation workflow or sequencing platform. As demonstrated here, the approach can easily be used to identify rare or low abundant mutations indicative of disease, such as leukemia.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Quantifying Ultra-Rare Pre-Leukemic Clones Via Targeted Error-Corrected Sequencing The quantification of rare clonal and subclonal populations from a heterogeneous DNA sample has multiple clinical and research applications for the study and treatment of leukemia. Specifically, in the hematopoietic compartment, recent reports demonstrate the presence of subclonal variation in normal and malignant hematopoiesis,[1,2] and leukemia is now recognized as an oligoclonal disease.[3] Currently, clonal heterogeneity in leukemia is studied using next-generation sequencing (NGS) targeting subclone-specific mutations. With this method, detecting mutations at 2-5% variant allele fraction (VAF) requires costly and time-intensive deep resequencing and identifying lower frequency variants is impractical regardless of sequencing depth. Recently, various methods have been developed to circumvent the error rate of NGS.[4,5] These methods tag individual DNA molecules with unique oligonucleotide indexes, which enable error correction after sequencing.

Here we present a direct application of error-corrected sequencing (ECS) to study clonal heterogeneity during leukemogenesis and validate the accuracy of this method with a series of benchmarking experiments. Specifically, we demonstrate the ability of ECS to identify leukemia-associated mutations in banked pre-leukemic blood and bone marrow from patients with either therapy-related acute myeloid leukemia (t-AML) or therapy-related myelodysplastic syndrome (t-MDS). T-AML/t-MDS occurs in 1-10% of individuals who receive alkylator- or epipodophyllotoxin-based chemotherapy or radiation to treat a primary malignancy.[6] For the seven individuals surveyed in this study, matched leukemia/normal whole-genome sequencing identified the t-AML/t-MDS-specific somatic mutations present at diagnosis. We applied our method for ECS to identify leukemia-specific mutations in four individuals from DNA extracted from blood and bone marrow samples collected years before diagnosis. In a separate study into the role of TP53 mutations in t-AML/t-MDS leukemogenesis, this method was used to identify leukemia-associated mutations at low frequency in samples banked years before diagnosis.[7] In two cases, subclones were identified below the 1% threshold of detection governed by conventional NGS. These results highlight the ability of targeted ECS to identify clinically silent single-nucleotide variations (SNVs).

Figure 1B:
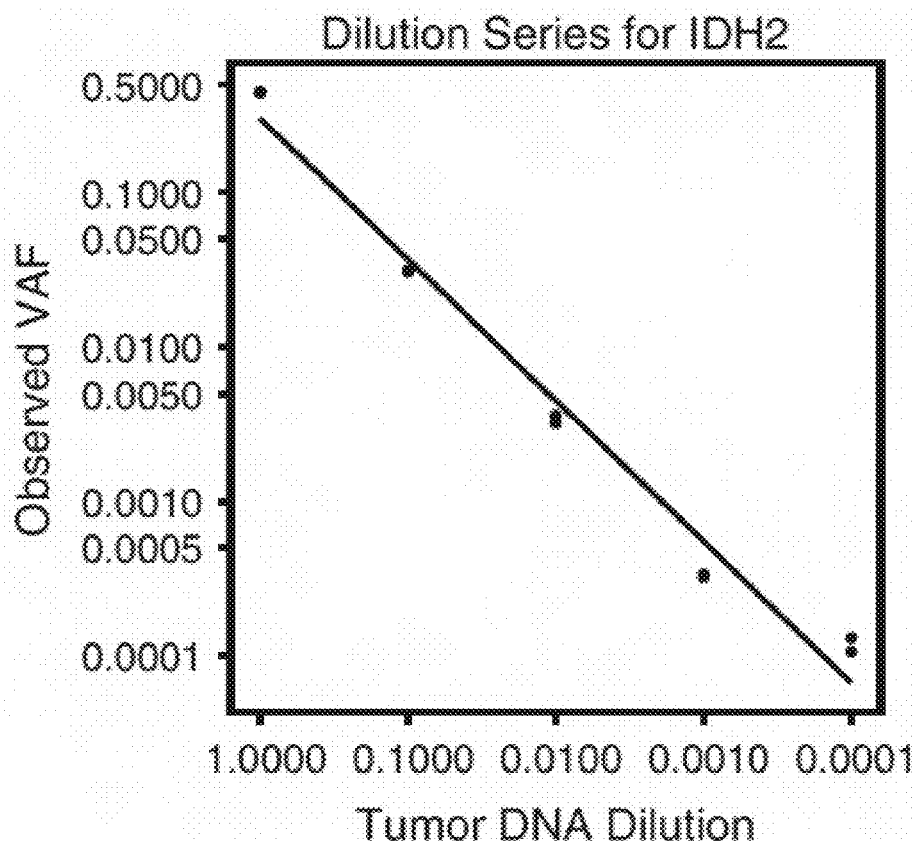
Figure 1C:
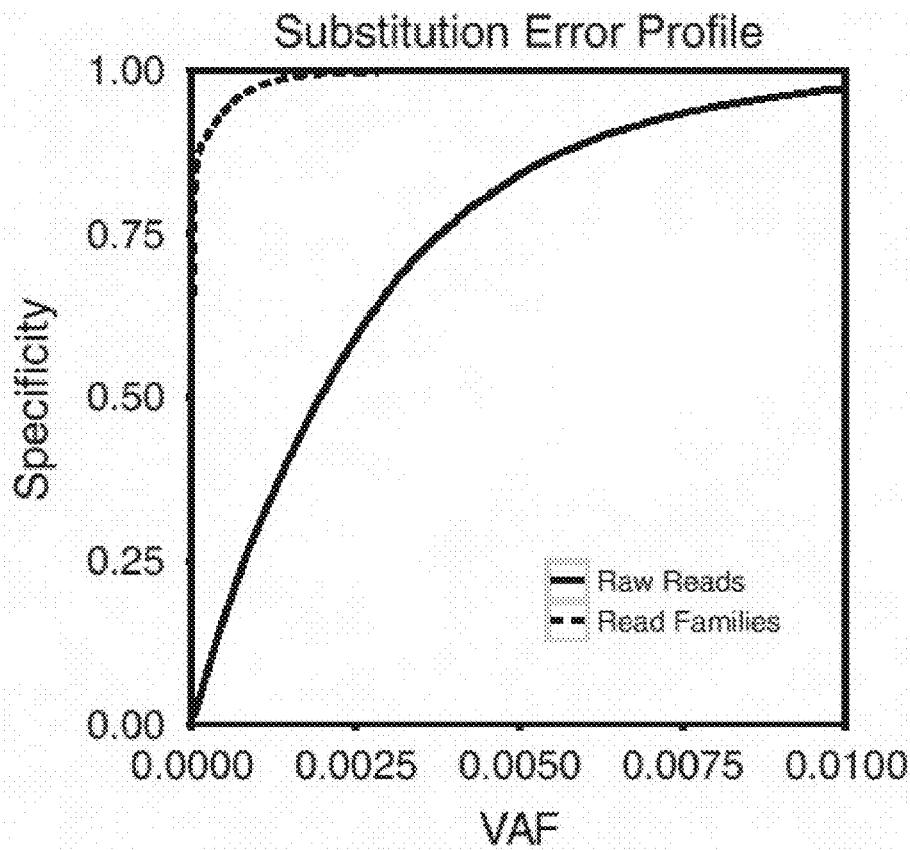
Figure 1D:
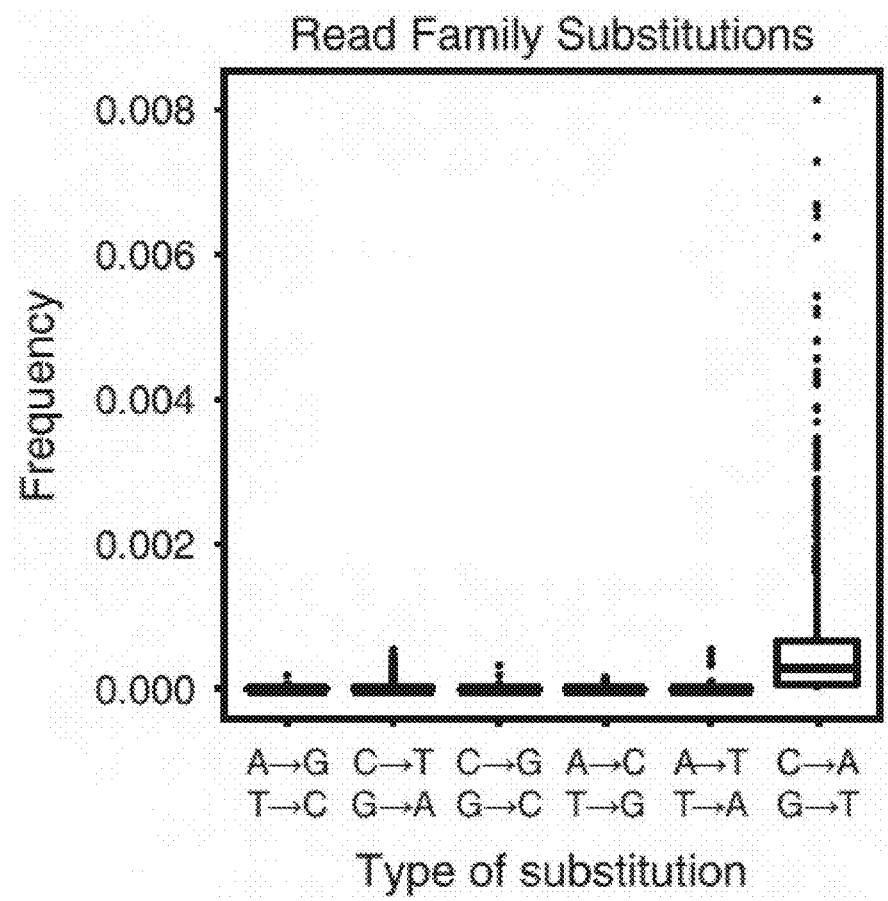
Figure 3:
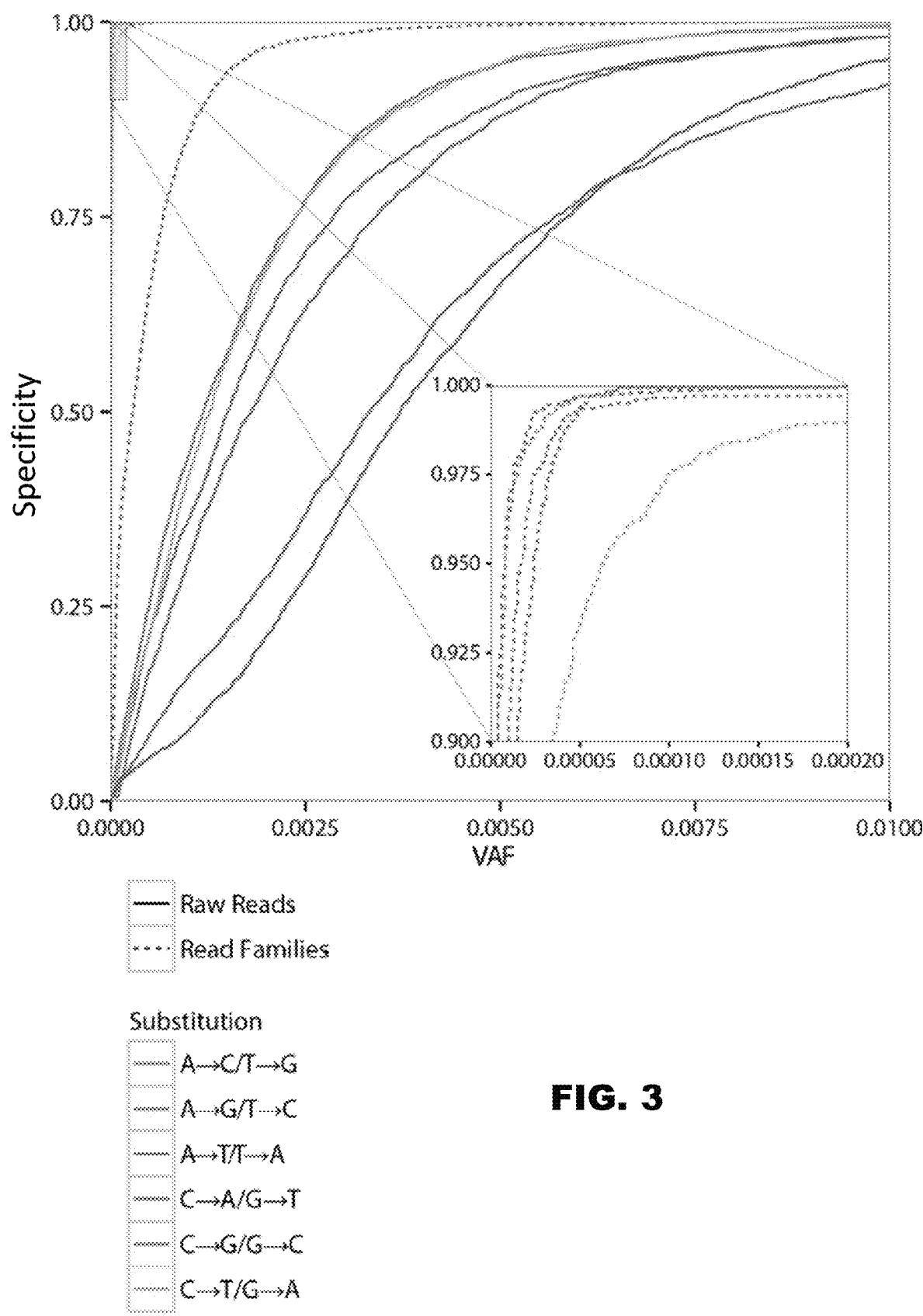
FIG. 3 depicts a graph showing the cumulative distribution function of the error profile comparing ECS to conventional deep sequencing. The variant allele fraction for each non-variant position covered in the dilution series experiment was sorted and plotted cumulatively. The variant allele fractions of errors were higher in every nucleotide covered across all substitution types for the raw sequenced reads compared the error-corrected consensus sequences generated from read families.
Figure 4:
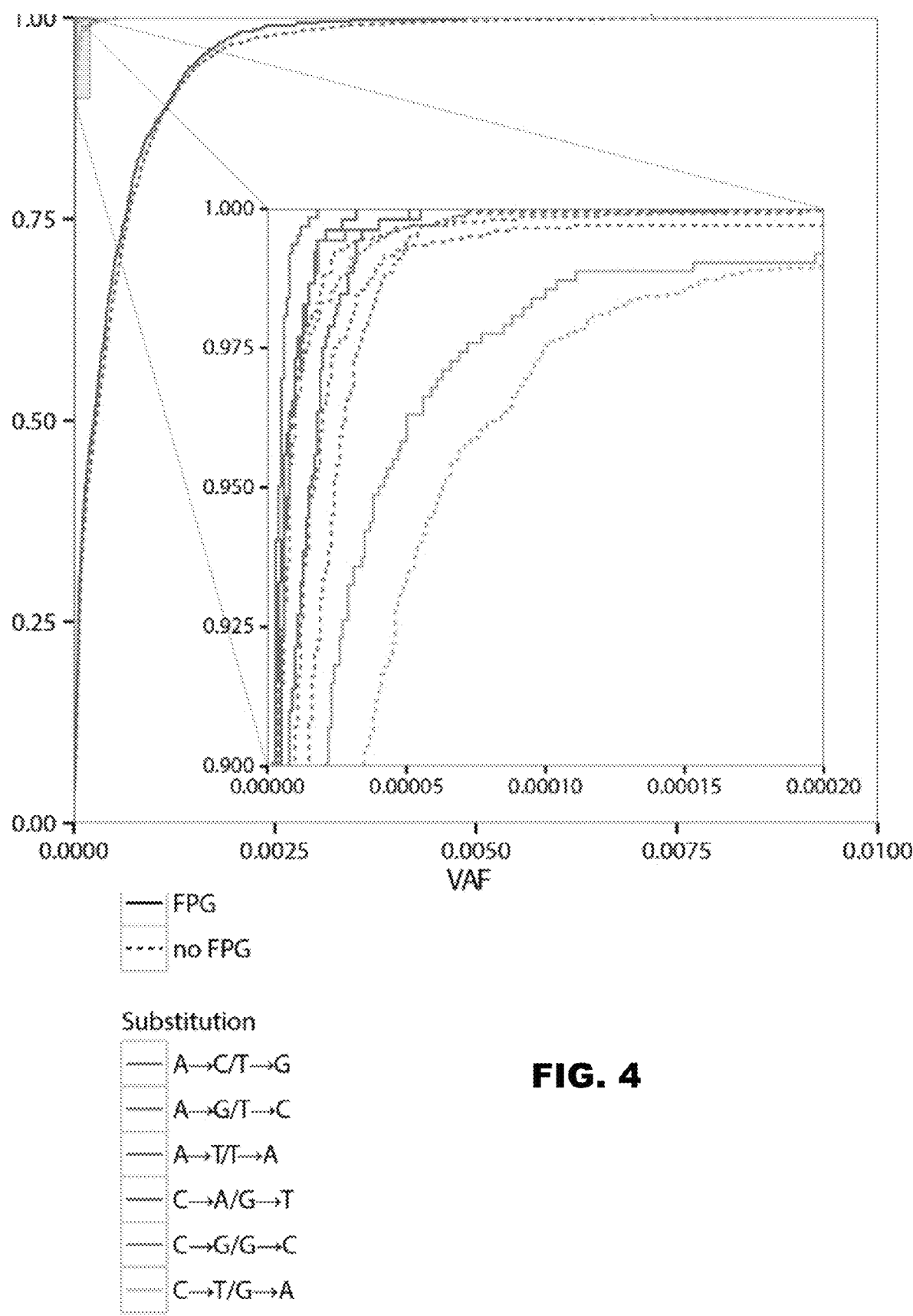
FIG. 4 depicts a graph showing the cumulative distribution function of read family error profile per specific substitution type with and without FPG pretreatment. The error profile of G to T (C to A) substitutions, consistent with guanine oxidation to 8-oxo guanine, was higher than the other classes of mutations. The C to T (G to A) substitutions, consistent with cytosine deamination to uracil, was visible just over the error profile for the remaining 8 types of substitutions (inset). FPG pretreatment did not appreciably change the error profile.
Figure 5A:
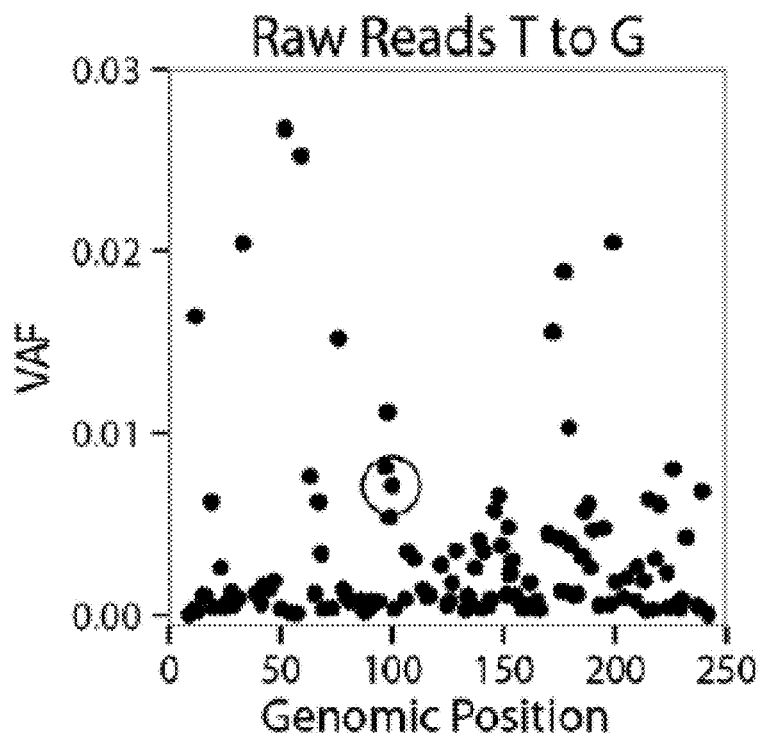
FIGS. 5A, 5B, 5C, 5D, 5E and 5F depict graphs showing ASXL1 mutations over time in UPN684949. Formalin-fixed paraffin-em bedded bone marrow samples were banked over three years (2002, 2003, 2004) from this individual. Conventional deep sequencing (FIGS. 5A, 5B, 5C) only distinguished the ASXL1 variant from the T to G sequencing errors in the 2003 banked sample at 0.097 VAF (FIG. 5B).
Figure 5B:
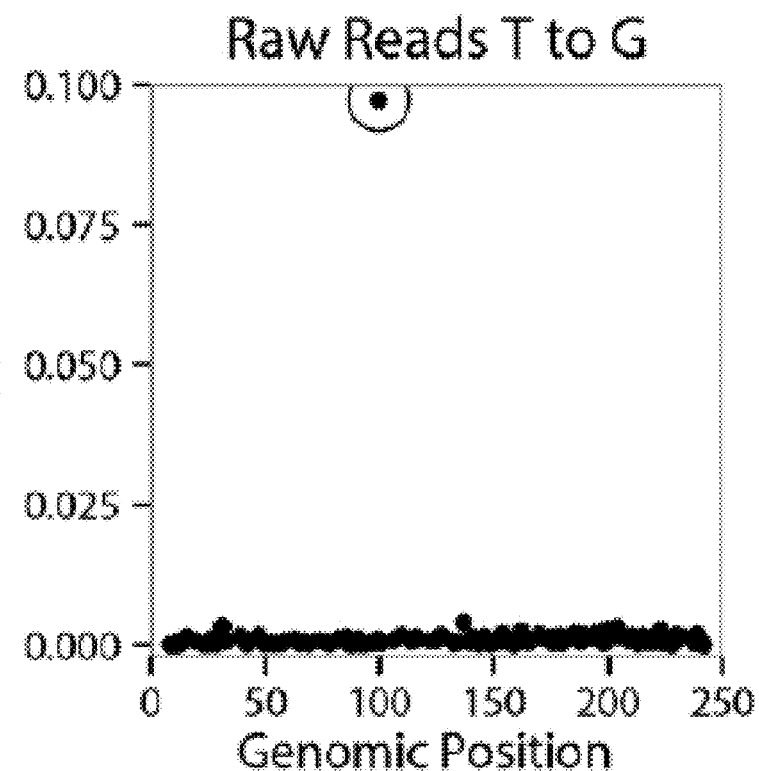
Figure 5C:
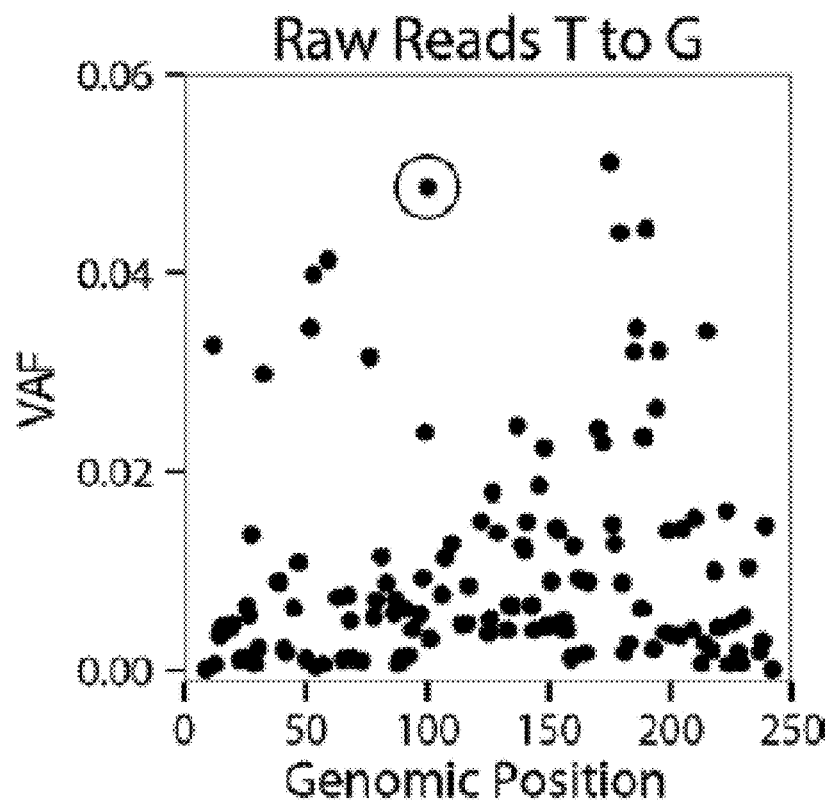
Figure 5D:
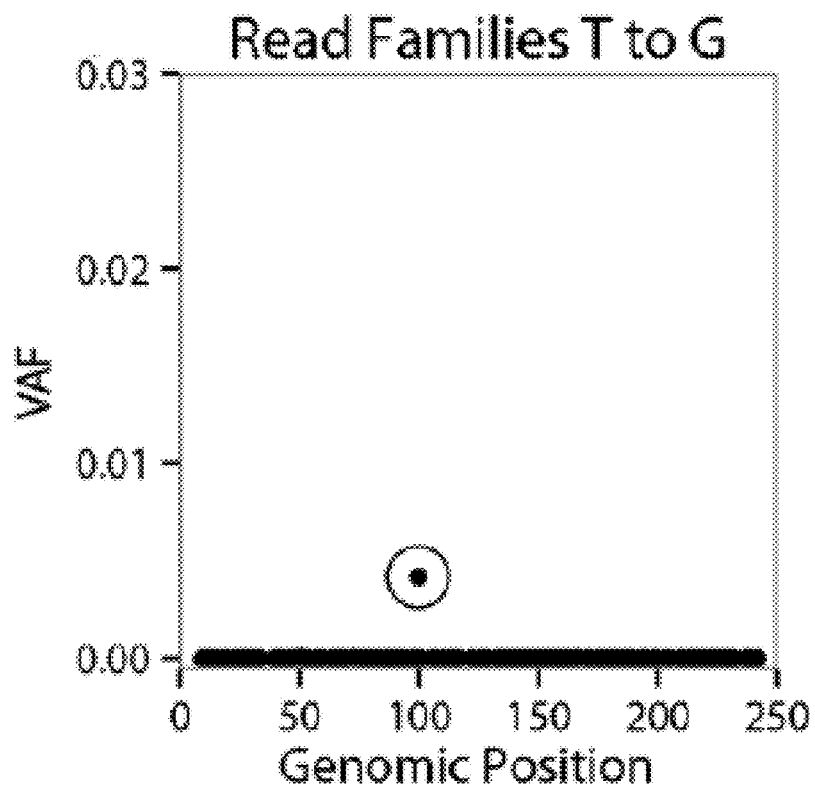
Figure 5E:
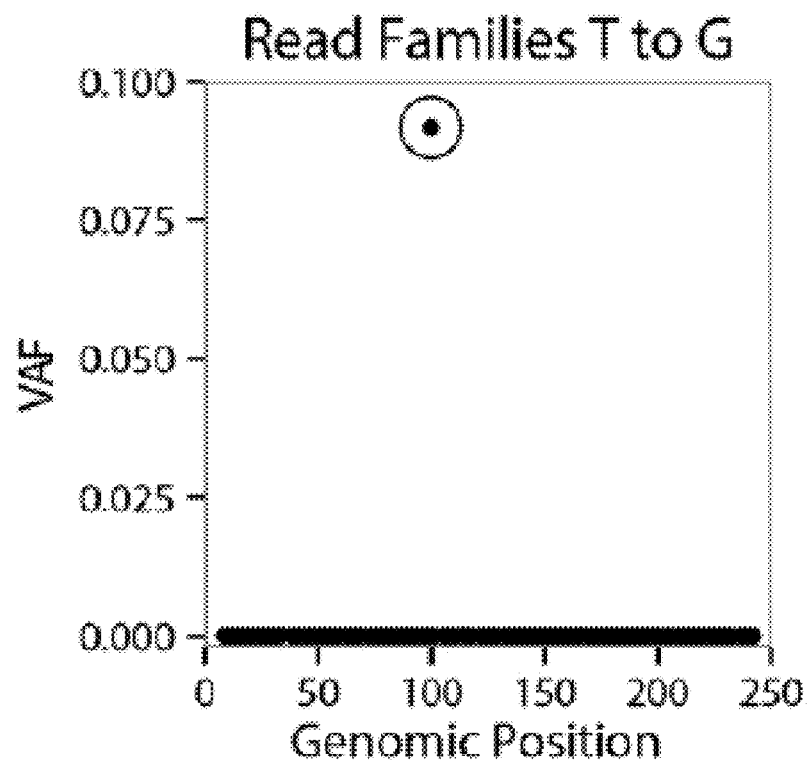
Figure 5F:
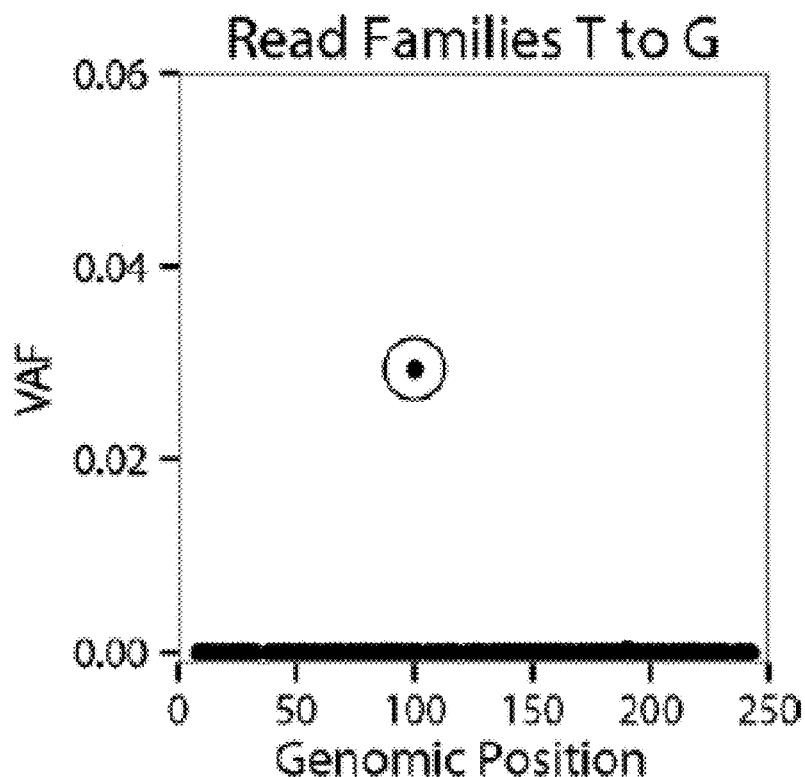
Figure 6A:
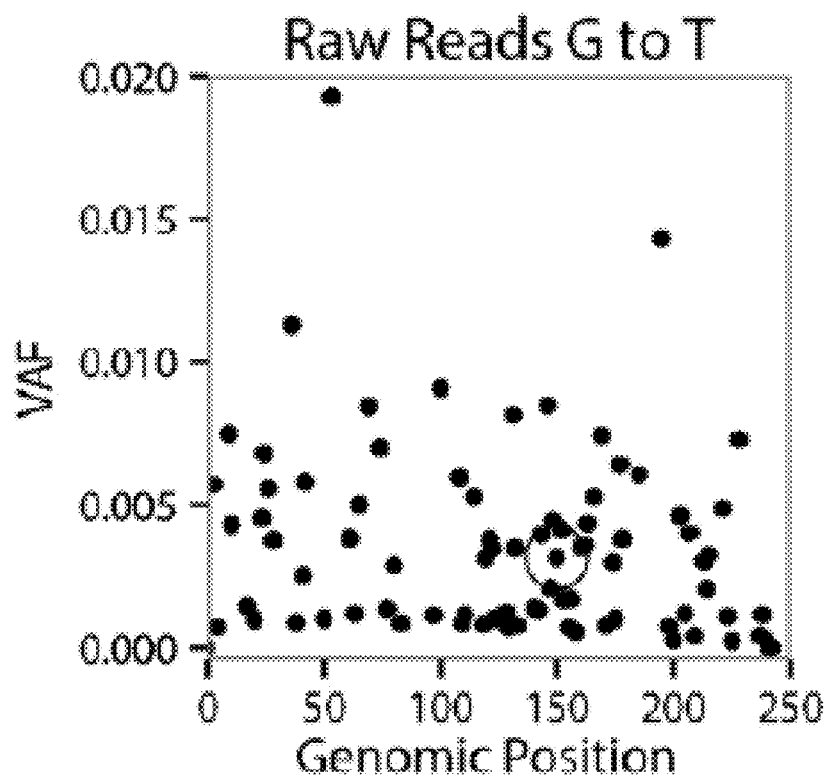
FIGS. 6A, 6B, 6C, 6D, 6E and 6F depict graphs showing U2AF1 mutations over time in UPN684949. Formalin-fixed paraffin-em bedded bone marrow samples were banked over three years (2002, 2003, 2004) from this individual. Conventional deep sequencing (FIGS. 6A, 6B, 6C) only distinguished the U2AF1 variant from the G to T sequencing errors in the 2003 banked sample at 0.036 VAF (FIG. 6B).
Figure 6B:
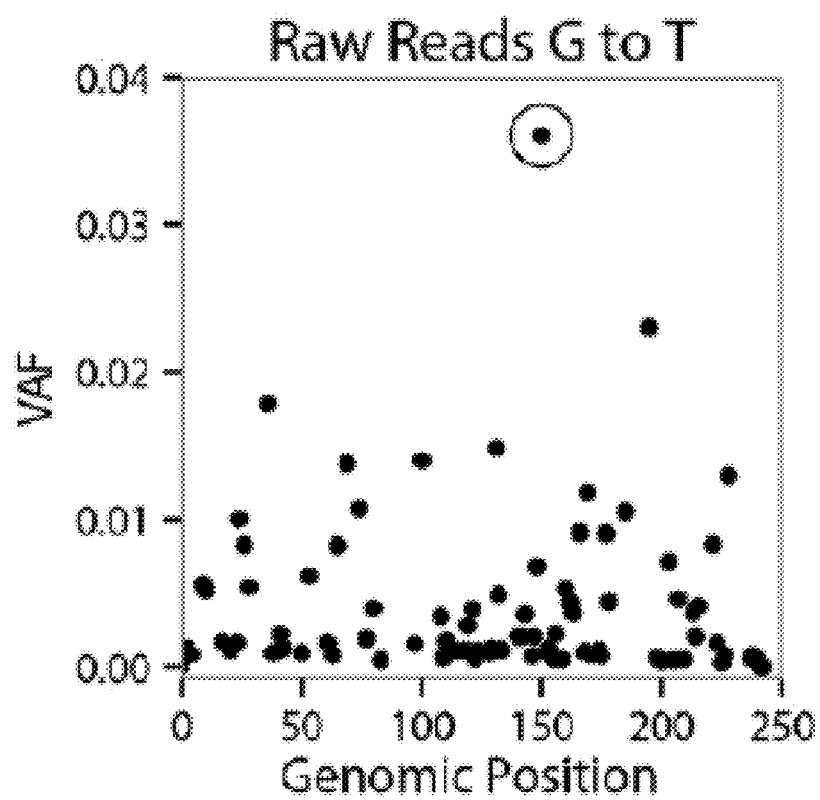
Figure 6C:
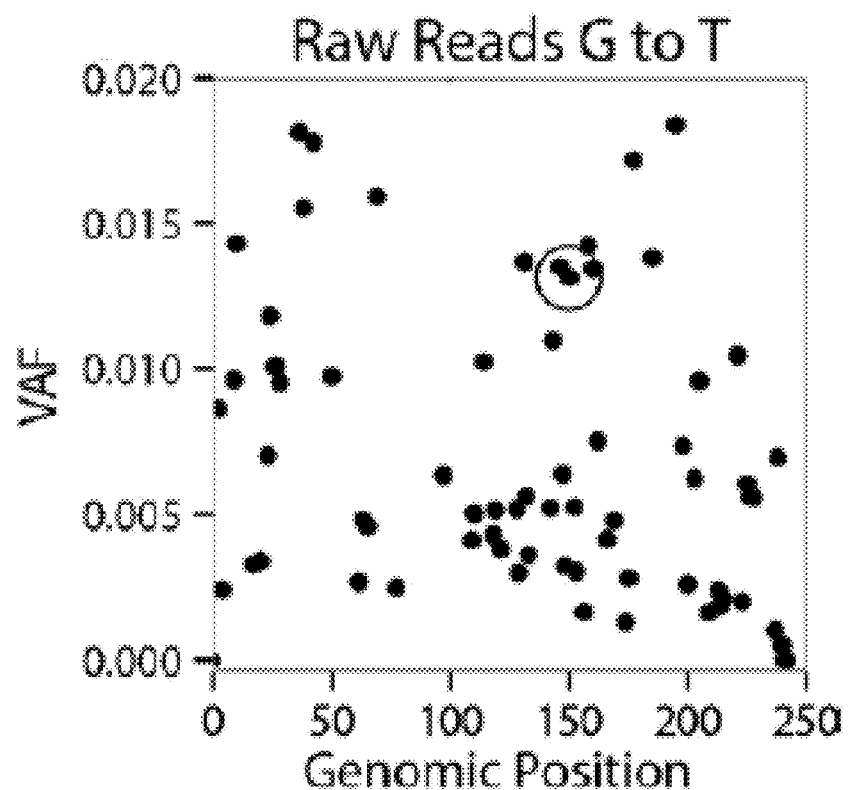
Figure 6D:
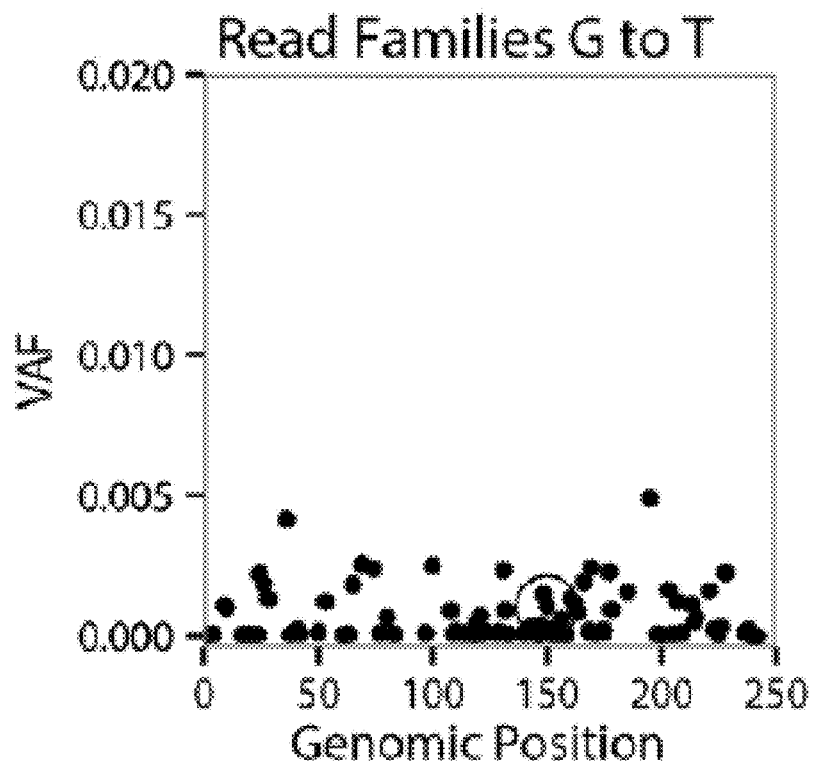
Figure 6E:
Figure 6F:
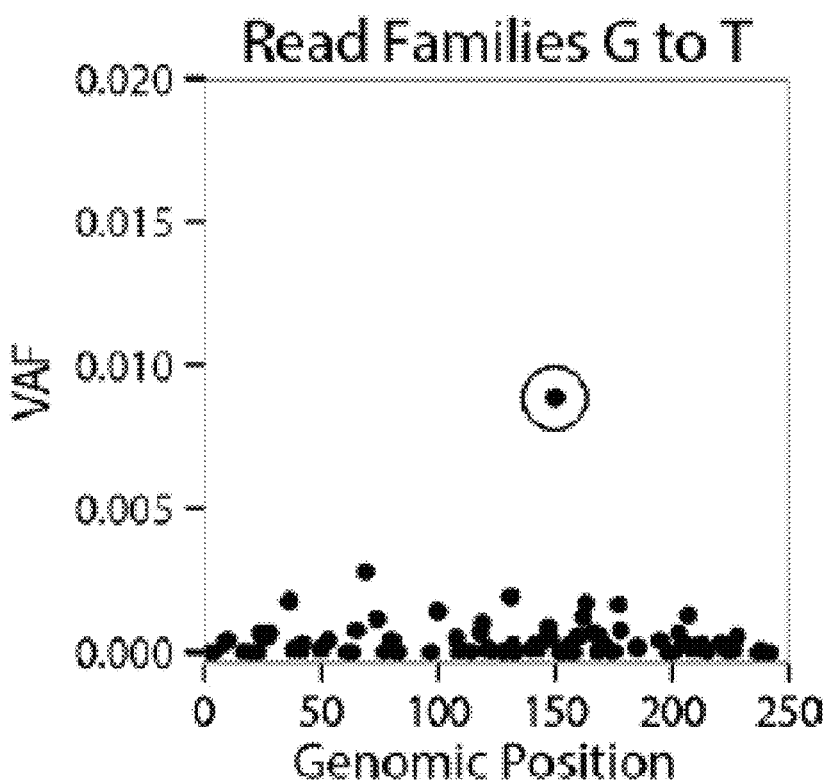

We employed ECS by tagging individual DNA molecules with adapters containing 16 bp random oligonucleotide molecular indexes in a manner similar to other reports.[4,5,8] Our implementation of ECS easily targets loci of interest by single or multiplex PCR and inserts seamlessly into the standard NGS library preparation (FIG. 2, Methods for Example 1). Our deviations from the standard protocol are ligation of customized adapters containing random indexes instead of the manufacturer's supplied adapters and a quantitative PCR (qPCR) quantification step before sequencing (Table 2). Following sequencing, sequence reads containing the same index and originating from the same molecule are grouped into read families. Sequencing errors are identified by comparing reads within a read family and removed to create an error-corrected consensus sequence (ECCS). We performed a dilution series experiment to assess bias during library preparation and determine the limit of detection for ECS. For this experiment, we spiked DNA from a t-AML sample into control human DNA, which was serially diluted over five orders of magnitude. The experiment was comprised of two technical replicates targeting two separate mutations (20 total independent libraries). The results demonstrate that ECS is quantitative to a VAF of 1:10,000 molecules and provides a highly reproducible digital readout of tumor DNA prevalence in a heterogeneous DNA sample ($r^2$ of 0.9999 and 0.9991, FIGS. 1A, 1B). We next characterized the error profile based on the wild-type nucleotides included in the dilution series experiment. Variant identification using the ECCSs was 99% specific at a VAF of 0.0016 versus 0.0140 for deep sequencing alone (FIG. 1C). We noticed that ECCS errors were heavily biased towards G to T transversions and to a lesser degree C. to T transitions (FIG. 1D, FIG. 3), as previously observed.[4,9] When separated by substitution type, variants identified from the ECCSs were 99% specific at a VAF of 0.0034 for G to T (C to A) mutations, 0.00020 for C to T (G to A) mutations and 0.000079 for the other eight possible substitutions. Although excess G to T mutations are a known consequence of DNA oxidation leading to 8-oxo-guanine conversion,[4] the pretreatment of samples with formamidopyrimidine-DNA glycosylase before PCR amplification did not appreciably improve the error profile of G to T mutations (FIG. 4).

As proof of principle, we applied ECS to study rare pre-leukemic clonal hematopoiesis in seven individuals who later developed t-AML/t-MDS. Leukemia/normal whole-genome sequencing at diagnosis was used to identify the leukemia-specific somatic mutations in each patient's malignancy (Table 3). We applied targeted ECS to query these 18 different loci in 10 cryopreserved or formalin-fixed paraffin-embedded blood and bone marrow samples that were 9-22-year old and banked up to 12 years before diagnosis (Table 4).

We generated ~25 Gb of 150 bp paired-end reads from six Illumina (San Diego, Calif., USA) MiSeq runs. We targeted 1-7 somatic mutations per individual (25 mutations spanning 5.5 kb from 15 genes in total) and identified leukemia-specific subclonal populations in four individuals up to 12 years before diagnosis (Table 1). For each sequencing library, we tagged ~2.5 million locus-specific amplicons generated from genomic DNA using high-fidelity PCR with randomly indexed custom adapters. Sequencing errors were removed to create ECCSs as described above. Each ECCS was then aligned to the reference genome for variant calling (FIG. 2).

Figure 1E:
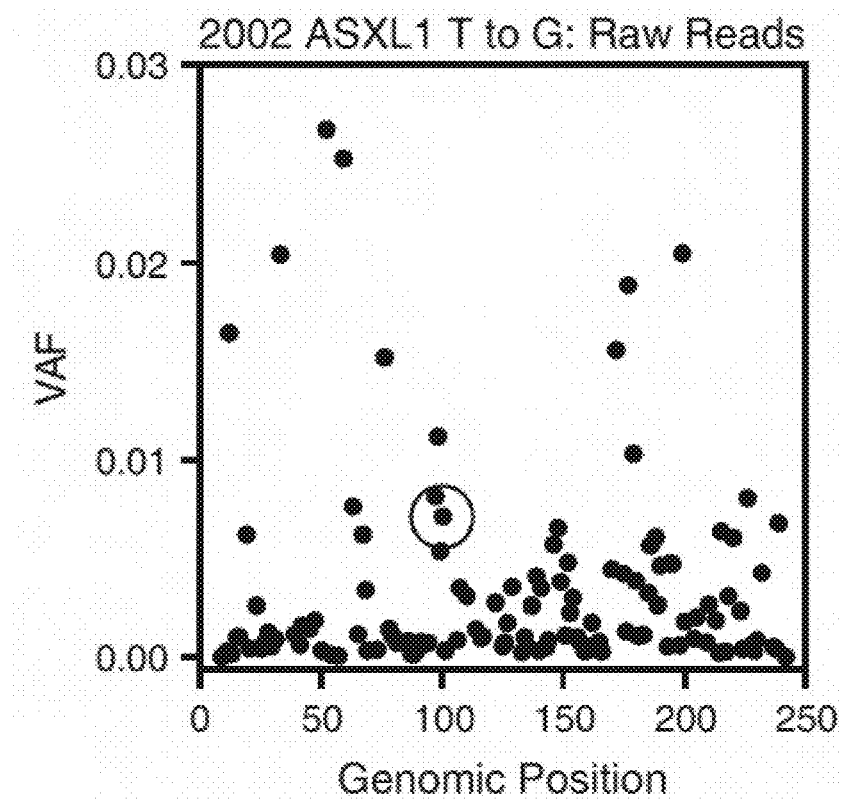
Figure 1F:
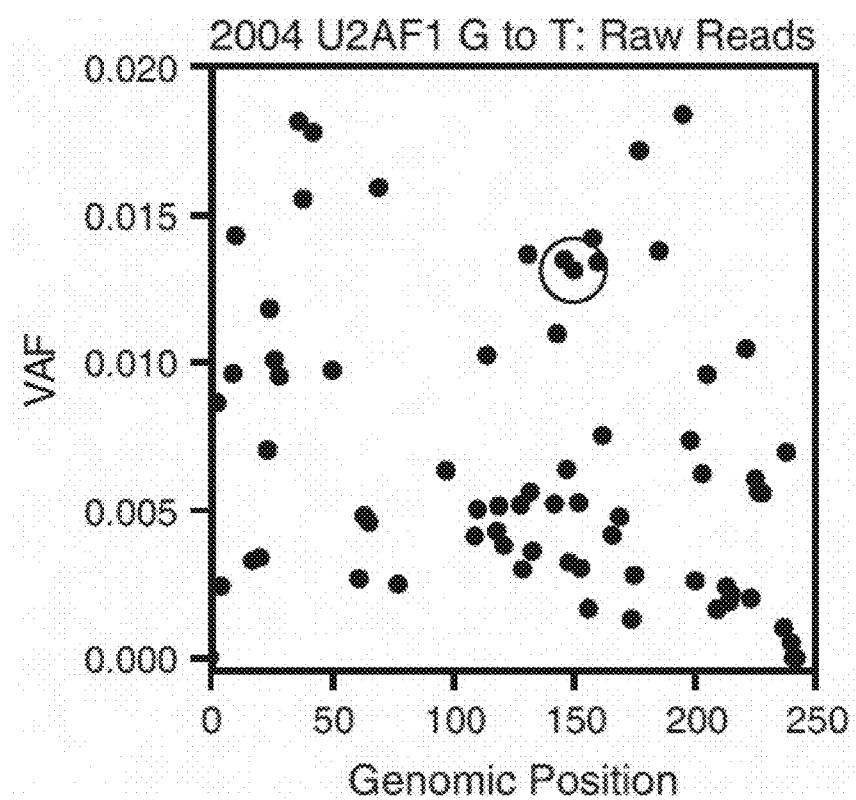
Figure 1G:
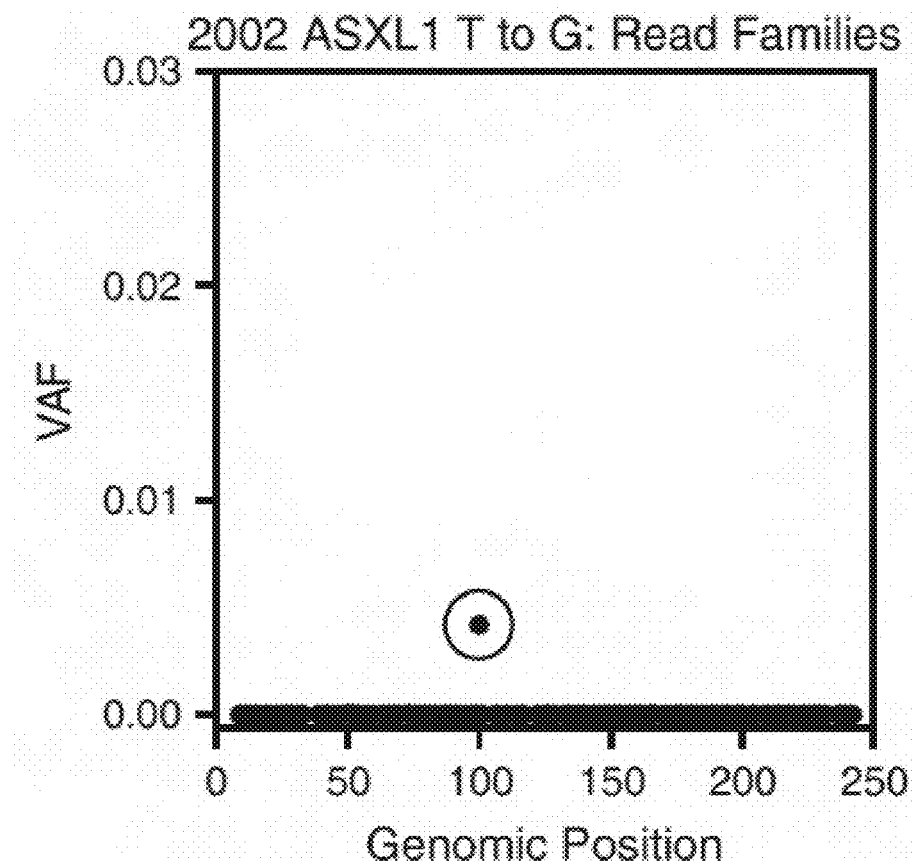
Figure 1H:
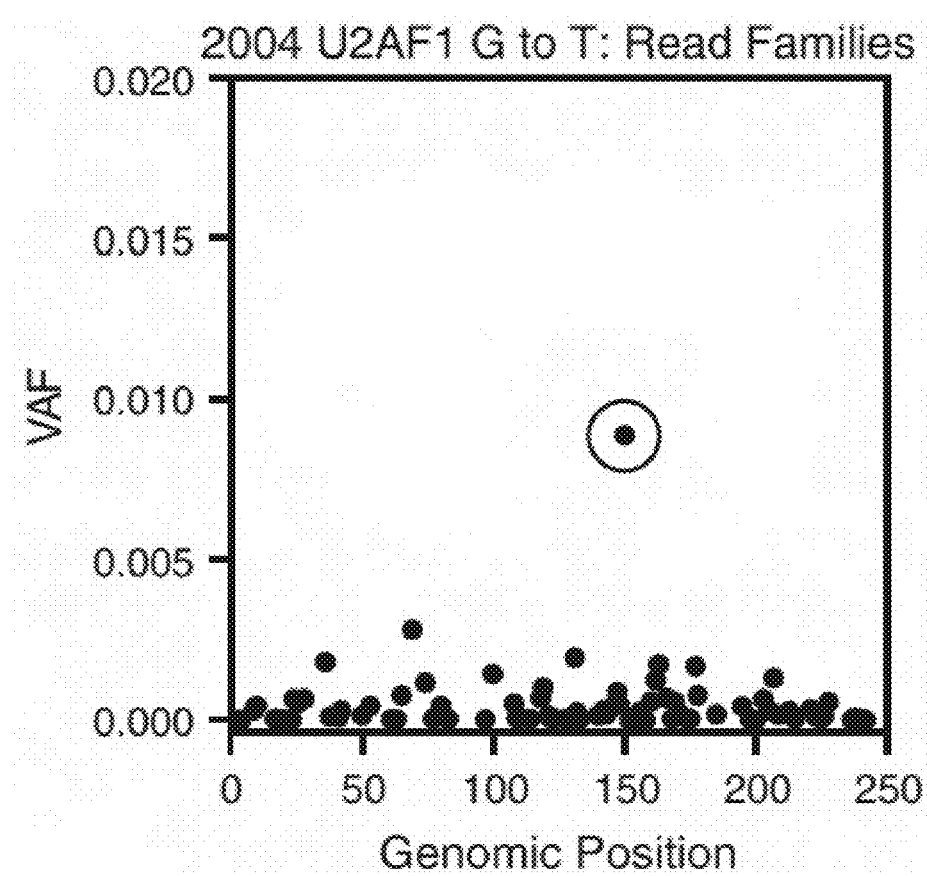

Using conventional deep sequencing, we detected t-AML/t-MDS-specific mutations in prior banked samples at variant allele fractions between 0.03 and 0.87 (data not shown). In one individual (UPN 684949), deep sequencing alone was insufficient to distinguish known ASXL1 and U2AF1 mutations from the sequencing errors in samples banked 5 and 3 years before t-MDS diagnosis, respectively (FIG. 1E, FIG. 1F). However, ECS identified the L866* nonsense mutation in ASXL1 at a VAF of 0.004 (FIG. 1G) and the S34Y missense mutation in U2AF1 at a VAF of 0.009 (FIG. 1H. In addition, ECS was able to temporally quantify these mutations from three pre-t-MDS samples banked yearly from 3 to 5 years before diagnosis (FIG. 5, FIG. 6). In two cases (UPN643006 and UPN942008), only a subset of the variants identified at diagnosis were present in the prior banked sample (Table 1). Specifically, in the UPN643006 sample, banked 12 years before diagnosis, a single-nucleotide deletion in ASXL1 was present at VAF 0.03. But, the G to T substitution in ASXL1, CTT deletion in GATA2 and G to T substitution in U2AF1 were not detectable in this prior banked sample.

Here we present a practical and clinically oriented application for targeted error-corrected NGS utilizing single molecule indexing. This method easily integrates into existing NGS library preparation protocols and enables the quantification of previously undetectable mutations in heterogeneous DNA samples. A modification to the standard NGS library preparation is the replacement of the stock adapters with our randomly indexed adapters and the addition of a qPCR step before sequencing. The qPCR step limits the number of molecules sequenced, ensuring adequate coverage for each read family. With these two modifications, we achieve highly specific detection for rare mutations. The bioinformatics analysis is straightforward and does not require proprietary algorithms or tools (Methods for Example 1). Our results highlight the ability of this method to identify rare subclonal populations in a heterogeneous biological sample. As applied to t-AML/t-MDS, we show these previously undetectable mutations are present years before diagnosis and fluctuate in prevalence over time.

A clinical application of ECS is to quantify minimal residual disease (MRD). As the genomic characterization of leukemia becomes more readily available, identifying causative genetic lesions and rare therapy-resistant subclones will become increasingly useful for risk stratification, therapeutic selection and disease monitoring. Already, whole-genome sequencing of AML has demonstrated that nearly every case of AML harbors one or more somatic SNVs.[10] These SNVs are more reliable clonal markers of malignancy than cell surface markers, which can change over time. Leveraging this information, conventional NGS was implemented retrospectively to detect MRD harboring leukemia-specific insertions/deletions (indels) as rare as 0.00001 VAF in NPM1[11] and 0.0001 VAF in RUNX1.[12] This was possible because indels are only rarely generated erroneously by NGS. Unfortunately, measuring rare leukemia-associated substitutions is limited owing to the relatively high error profile of conventional NGS.[13] However, ECS can achieve the 1:10,000 limit of detection featured by conventional MRD platforms.[14] For patients whose leukemia lacks suitable markers for conventional MRD, ECS could offer an alternative with comparable sensitivity and specificity that is easy to implement in a clinical sequencing lab. Furthermore, the ability to multiplex targets for ECS enables the surveillance of known mutations and the simultaneous discovery of new somatic mutations. Ongoing work will directly compare gold-standard MRD methods with targeted ECS in patients with and without relapsed leukemia.

Methods for Example 1

Study Design:

Blood and bone marrow samples from patients treated for t-AML/t-MDS at Washington University were banked or accessed following informed consent under Human Research Protection Protocol #201011766. Patients included in this study underwent matched leukemia and non-cancer (skin) whole genome sequencing on the Illumina HiSeq 2500 platform, which identified tumor-specific somatic coding mutations in leukemia samples. Our study focused on identifying these known mutations from matched blood or bone marrow samples banked 1-12 years prior to the initial diagnosis of t-AML/t-MDS.

Figure 2A:
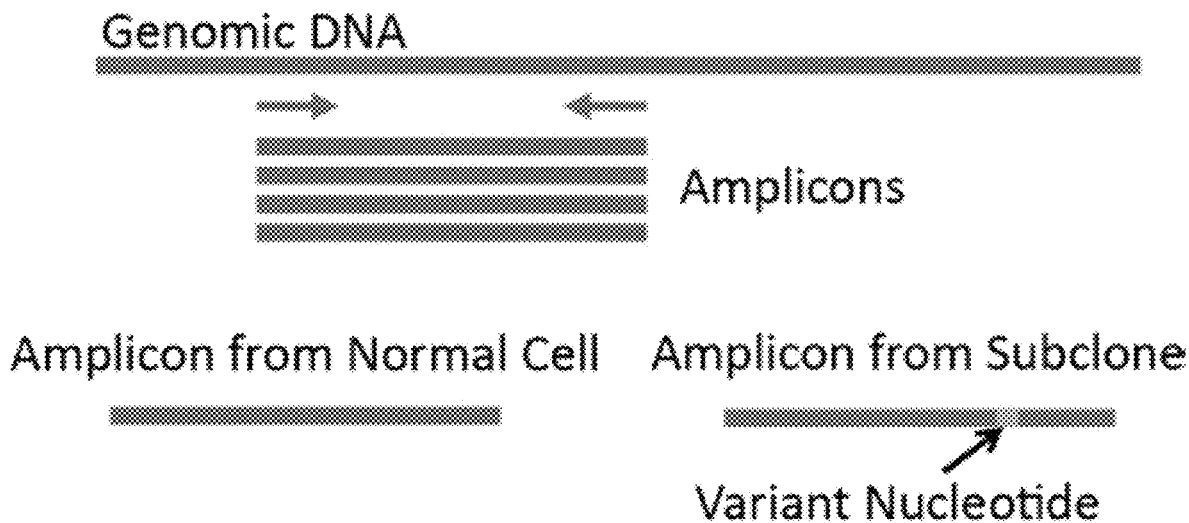
FIGS. 2A, 2B, 2C, 2D, 2E and 2F depict schematics of the error-corrected sequencing workflow. Schematic depiction of library preparation (FIGS. 2A, 2B, 2C) and bioinformatics analysis (FIGS. 2D, 2E, 2F) for generating read families and error-corrected consensus sequences. First, the region of interest is amplified from genomic DNA (FIG. 2A), then the sequencing library is prepared (FIG. 2B) generating a sequence library (FIG. 2C). From the sequence library, read families are generated (FIG. 2D) and an error-corrected consensus sequence (ECCS) is created (FIG. 2E). The ECCSs are aligned to identify a variant allele (FIG. 2F).

Sample Preparation:

Genomic DNA was generated from either FFPE or cryopreserved peripheral blood or bone marrow samples using the QIAamp DNA FFPE Tissue or DNA Mini Kit (Qiagen). PCR primers were designed using primer3[1] to amplify regions harboring individual leukemia-specific mutations from the banked biological samples (Table 5). The concentration of each purified DNA sample was determined using the Qubit dsDNA HS Assay Kit (Life Technologies). Genomic DNA (400-800 ng) was amplified using the Q5 High-Fidelity 2× Master Mix (New England Biolabs) in a 25 uL reaction with 0.5 uM primers (FIG. 2A). The following conditions were used: 98 C for 30 s; 16-30 cycles of 98 C for 10 s, 62-72 C (based on a separate optimization) for 30 s and 72 C for 30 s; 72 C for 2 m; hold 10 C. The PCR reactions were purified using the Agencourt AMPure XP (Beckman Coulter) bead-based protocol without modification.

For a few of the patient samples, the amount of input genomic DNA was limited. In these cases, modifications were made to the protocol to amplify multiple leukemia-specific mutations from the same biological sample (multiplex PCR). Patient-specific primers were pooled during a first round of PCR and amplified for roughly 16 cycles, similar to pre-amplification described in TAm-Seq[2]. After purification the DNA was split into a single PCR reaction per patient-specific SNVs and amplified using only that specific primer pair, again for roughly 16 cycles. This allowed us to generate diverse amplicon pools for multiple loci using only 400-800 ng of starting DNA.

Figure 2B:
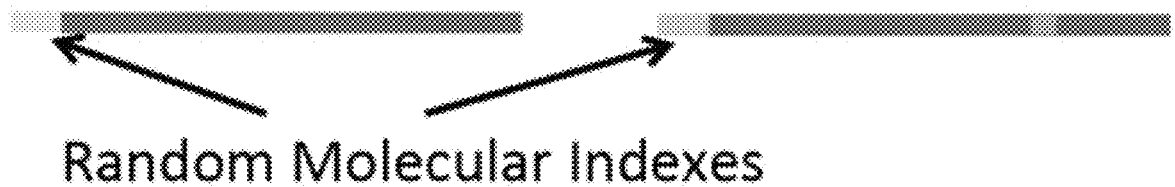

ECS Library Preparation:

The concentration of the purified PCR products was measured using the Qubit dsDNA HS Assay Kit (Life Technologies). NGS libraries were prepared from 800 ng of amplicons for each sample/mutation using the Illumina TruSeq DNA Sample Preparation Kit (Illumina). We replaced the Illumina-provided Y-shaped adapters with custom adapters containing a random 16 base pair oligonucleotide index sequence (Table 2). Adapters were diluted to 40 uM in Tris-EDTA with 5 nM NaCl and annealed using the following conditions: 95 C for 5 m then decreased by 1 C every 30 s to 4 C. Aside from the custom adapters used for ligation, the library preparation protocol from Illumina was mostly unchanged (FIG. 2B). Enrichment for correctly ligated products was completed using a 50 uL Q5 PCR amplification with 2 uL of ligation product and 0.5 uM Illumina specific primers under the following conditions: 98 C for 30 s; 6 cycles of 98 C for 10 s, 57 C for 30 s and 72 C for 30 s; 72 C for 2 m; hold 10 C The PCR reaction was purified using a modified Ampure bead cleanup, which increased the size range of purification to remove adapter dimers. 100 uL of beads were washed twice with ddH2O to remove the stock polyethylene glycol (PEG) solution. The solution was replaced with 25.5 uL 50% wt/vol PEG (Sigma), 37.5 uL 5M NaCl and 37 uL ddH2O. The PCR reaction was added to this solution and purified per the standard Ampure protocol.

Quantification by qPCR:

We sought to generate read families from a single randomly-indexed molecule with roughly seven-fold coverage. Given the bandwidth of a single Illumina MiSeq run was roughly 15-18 million read pairs, we sought to generate sequencing libraries from roughly 2.5 million molecules. To achieve this, we quantified the concentration of each library using the qPCR NGS Library Quantification Kit, Illumina GA (Agilent Technologies). Based on the measured concentration, each library was diluted to 0.4 pM such that a 10 uL volume of the diluted library would contain ~2.5 million molecules. The 10 uL aliquot of diluted sequencing library was then amplified for 16-20 cycles and purified with the same Q5 and modified Ampure bead protocol used for the previous enrichment PCR step. The final library was visualized on a 2% SYBR Safe gel (Life Technologies) and quantified using Qubit dsDNA HS Assay Kit. When multiplexing samples on a single lane of sequencing, individual sequencing libraries were combined in equimolar amounts after enrichment PCR and the pooled sample was diluted and quantified using qPCR as stated previously. However, we also found it possible to pool amplicons in equimolar amounts after the initial genomic DNA amplification and make a single sequencing library. Up to 7 different amplicons were multiplexed on a single MiSeq run. Multiplexing was only possible with mutations in different genes or within different exons of the same gene because the samples were demultiplexed by alignment.

Figure 2C:
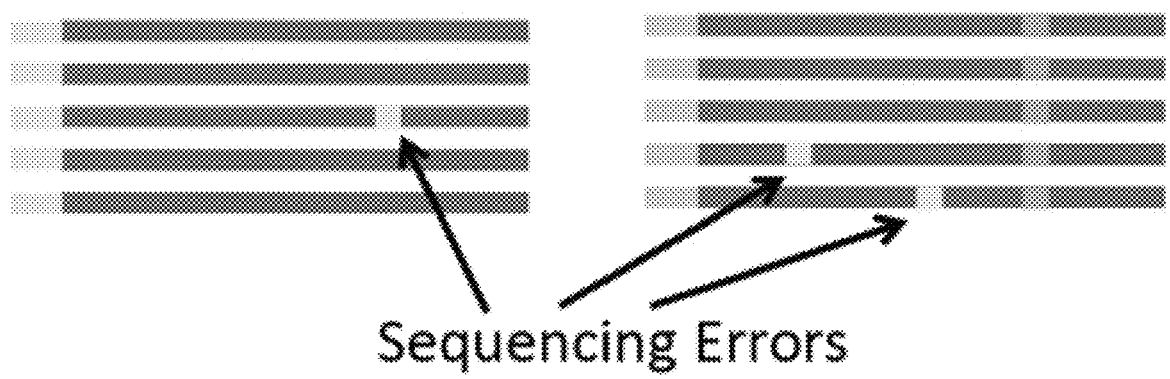

Sequencing:

Each library was sequenced on the Illumina MiSeq instrument as specified by the manufacturer (FIG. 2C). Approximately, 5-10% of PhiX control DNA was spiked into each sequencing experiment. Each completed sequencing run contained roughly 15-18M paired-end 150 bp reads. Raw sequence reads were aligned to the PhiX genome using Bowtie 2[3]. Sequence reads aligning to PhiX were removed from further analysis. The remaining sequence reads were aligned to UCSC hg19/GRCh37 using Bowtie 2 for comparison against error-corrected consensus sequences (ECCS) derived from read families (below).

Figure 2D:
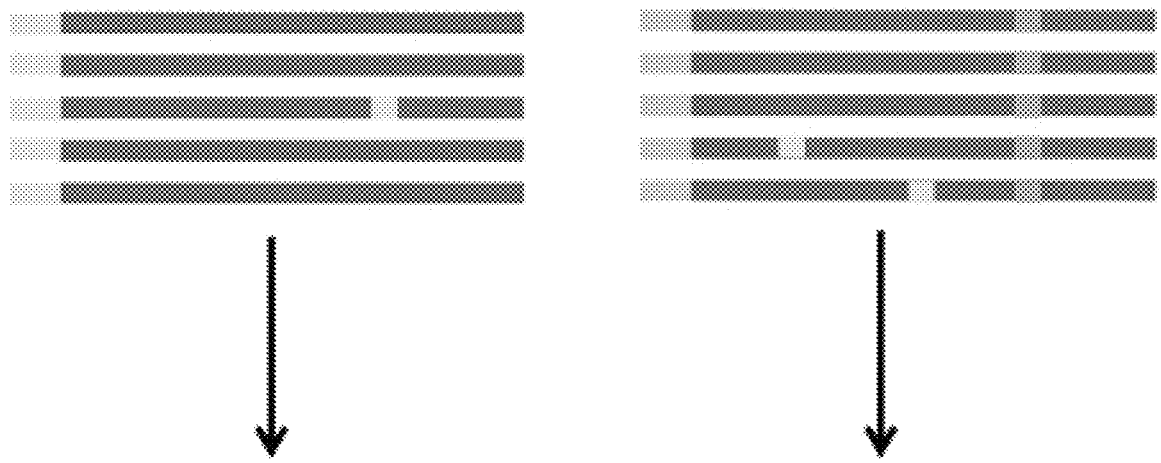
Figure 2E:
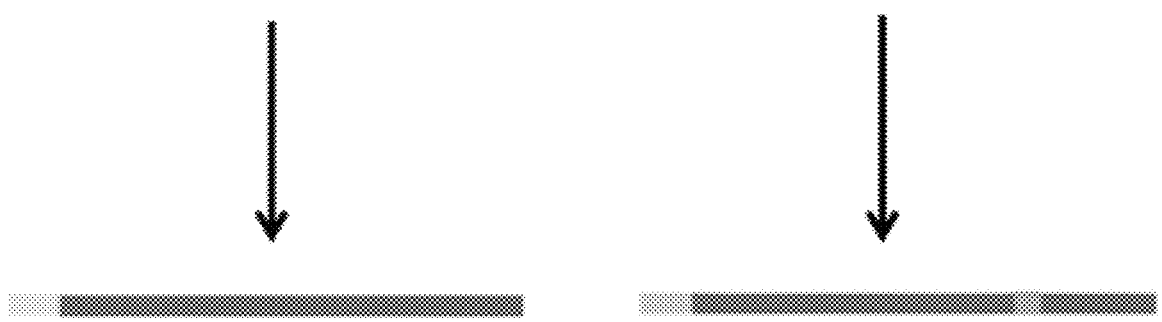
Figure 2F:
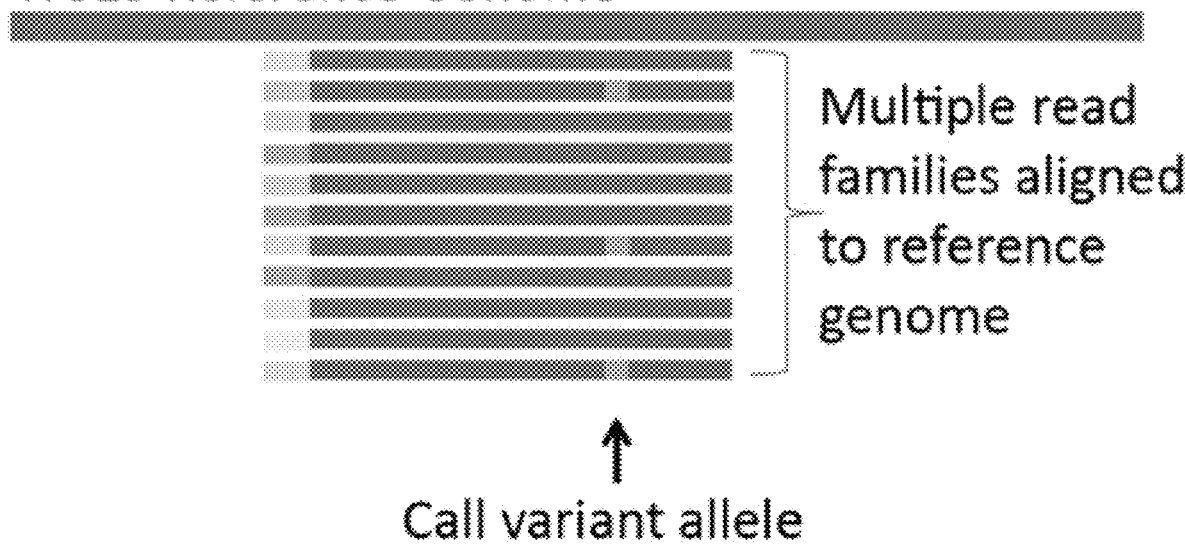
Figure 7:
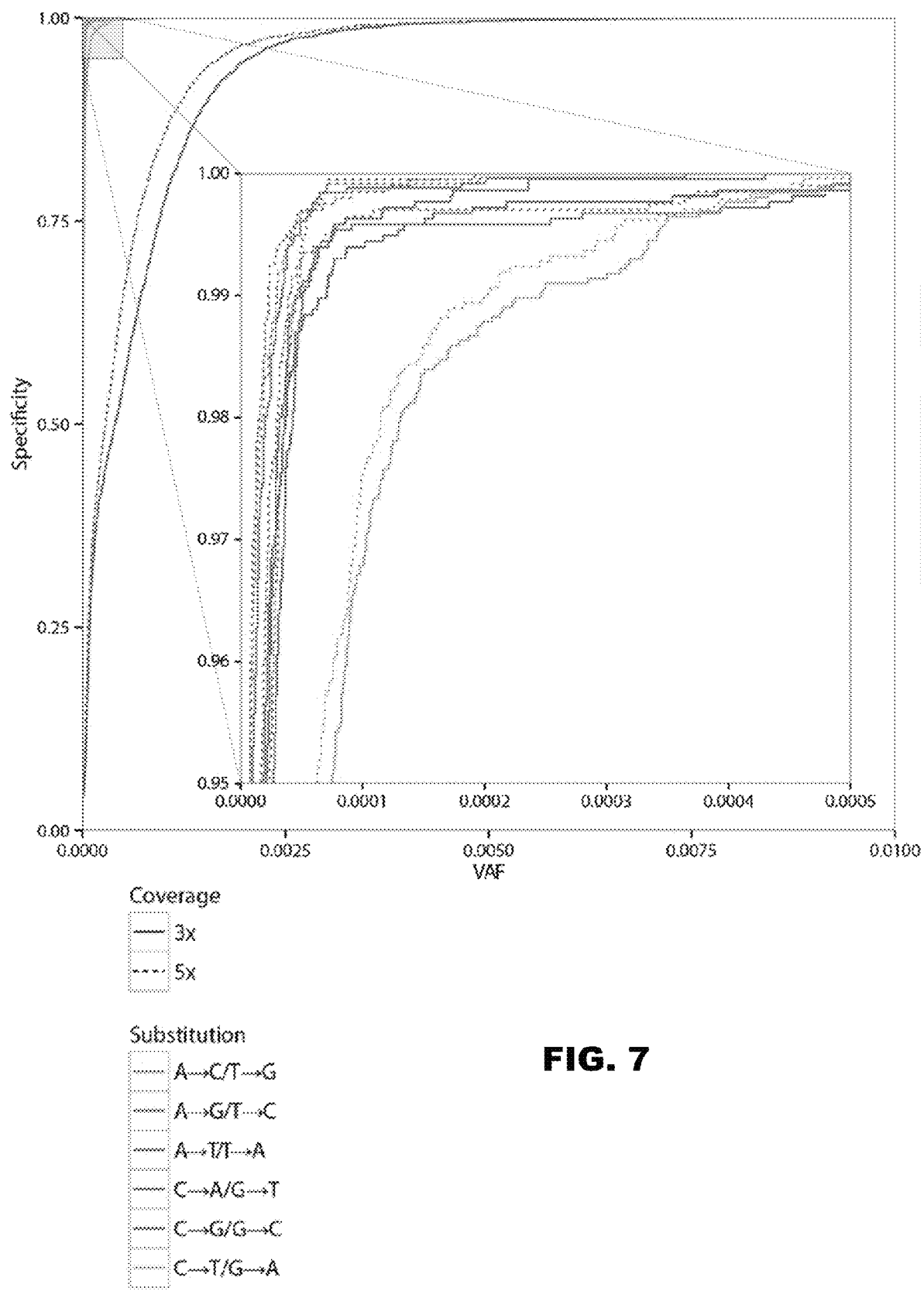
FIG. 7 depicts a graph showing the error profile observed with increased read family size. Read families generated with 3× or greater coverage (solid line) had a higher cumulative distribution of erroneous substitutions called compared to read families with 5× or greater coverage (dotted line).
Figure 8:
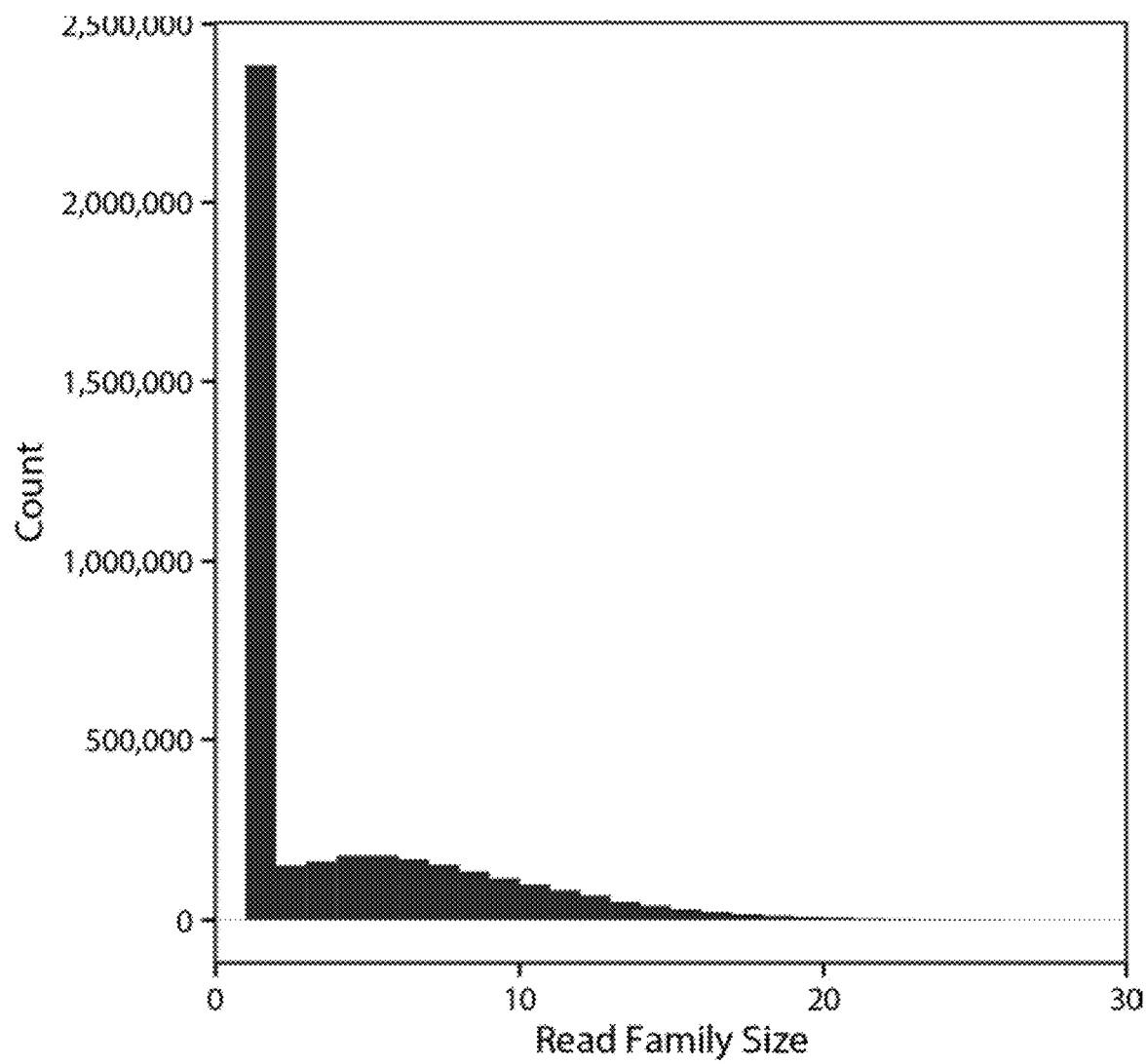
FIG. 8 depicts a graph showing the representative distribution of read family size. Singletons represent index sequences containing a sequencing error. Excluding singletons, the median read family size was 7× (mean 7.4×). Only read families with 5-20 reads were included in ECS analysis.

Error Corrected Consensus Sequences:

Sequence reads containing the same index sequence (originated from the same randomly-indexed molecule) were aligned to each other to generate read families in a fashion similar to previously published methods[4,5] (FIG. 2D). Previous studies used a minimum read family size of three[5]. We found using a more stringent cutoff of five reduced the error rate in the read families (FIG. 7). The median read family size was seven reads per index (FIG. 8). Paired-end reads within a read family were error corrected in a stepwise fashion (FIG. 2E). First, at every position, the nucleotides called by each sequence read were compared and a consensus nucleotide was called if there was at least 90% agreement between the reads. If there was less than 90% agreement, an N was called in the consensus sequence at that position. Errors that occurred during library preparation and sequencing were removed because they were not shared between different reads within a read family. Second, an ECCS was thrown out if less than 90% of the 300 nucleotides comprising the paired-end read were assigned a non-N nucleotide. These ECCSs were locally aligned to UCSC hg19/GRCh30 using Bowtie2[3] (FIG. 2F). The aligned ECCSs were processed with Mpileup[6] using the parameters-BQ0-d 10000000000000. This removed the coverage thresholds to ensure that all of the pileup output was returned regardless of variant allele fraction (VAF) or coverage. Variant allele factions comprised of both the expected mutations and the background errors for each sample were visualized using IGV[7] and graphically represented using ggplot2[8]. Each known variant was plotted relative to the error-profile of that specific substitution class (e.g. an expected C to T transition was compared against the C to T error profile). Variants distinguishable from the noise for that specific error class and located at the expected position within the amplicon were called true positives. The threshold for calling true variants varied based on the error profile of that substitution class. Based on our benchmarking studies we were 99% specific to detect variants above 0.0034 VAF for G to T (C to A) substitutions, 0.00020 VAF for C to T (G to A) substitutions and 0.000079 VAF for the other eight possible substitutions.

TABLE 1

Patient-specific leukemia-associated somatic mutations identified by ECS.

| UPN | Sample ID | Years prior | Gene | Chr | Position | Mut | Amino-acid change | Variant RFs | Reference RFs | VAF |
|---|---|---|---|---|---|---|---|---|---|---|
| 446294 | 75.02 | 1 | OBSCN | 1 | 228461129 | A to G | H1857R | 61 238 | 156 986 | 0.2806 |
|  |  |  | TP53 | 17 | 7578271 | T to A | H193L | 220 551 | 110 047 | 0.6671 |
| 499258 | 24.06 | 2 | RUNX1 | 21 | 36252865 | C to G | R139P | 2 | 486 196 | 0 |
| 574214 | 26.04 | 7 | DMD | X | 32827676 | G to A | R187* | 7 | 199 945 | 0 |
| 643006 | 80.01 | 12 | ASXL1 | 20 | 31022448 | G to T | G645C | 7 | 85 781 | 0.0001 |

TABLE 1-continued

Patient-specific leukemia-associated somatic mutations identified by ECS.

| UPN | Sample ID | Years prior | Gene | Chr | Position | Mut | Amino-acid change | Variant RFs | Reference RFs | VAF |
|---|---|---|---|---|---|---|---|---|---|---|
| | | | ASXL1 | 20 | 31022442 | del G | G645fs | 2 898 | 82 245 | 0.034 |
| | | | GATA2 | 3 | 128200135 | del CTT | K390in__fr__del | 0 | 4 187 | 0 |
| | | | U2AF1 | 21 | 44524456 | G to T | S34Y | 85 | 414 613 | 0.0002 |
| 684949 | 91.01 | 5 | ASXL1 | 20 | 31023112 | T to G | L866* | 3 583 | 853 598 | 0.0042 |
| | | | U2AF1 | 21 | 44524456 | G to T | S34Y | 545 | 514 410 | 0.0011 |
| | 92.02 | 4 | ASXL1 | 20 | 31023112 | T to G | L866* | 54 074 | 535 976 | 0.0916 |
| | | | U2AF1 | 21 | 44524456 | G to T | S34Y | 11 195 | 355 276 | 0.0305 |
| | 93.01 | 3 | ASXL1 | 20 | 31023112 | T to G | L866* | 17 319 | 573 629 | 0.0293 |
| | | | U2AF1 | 21 | 44524456 | G to T | S34Y | 827 | 92 104 | 0.0089 |
| 856024 | 30.02 | 1 | S100A4 | 1 | 153517192 | A to G | F27L | 0 | 211 512 | 0 |
| | | | IGSF8 | 1 | 160062252 | G to A | P516S | 0 | 22 614 | 0 |
| | | | PLA2R1 | 2 | 160798389 | A to G | L1431P | 2 | 338 616 | 0 |
| | | | POU3F2 | 6 | 99282794 | C to A | S15R | 8 | 201 240 | 0 |
| | | | ANKRD18B | 9 | 33524645 | G to A | C53Y | 7 | 214 836 | 0 |
| | | | ESR2 | 14 | 64701847 | G to A | A416V | 10 | 135 861 | 0.0001 |
| | | | FBN3 | 19 | 8155081 | G to A | P2029L | 0 | 152 304 | 0 |
| 942008 | 33.04 | 9 | IDH2 | 15 | 90631934 | C to T | R88Q | 23 170 | 236 587 | 0.0892 |
| | | | RUNX1 | 21 | 36231791 | T to C | D171G | 40 | 253 168 | 0.0002 |
| | 107.01 | <1 | IDH2 | 15 | 90631934 | C to T | R88Q | 138 180 | 161 371 | 0.4613 |
| | | | RUNX1 | 21 | 36231791 | T to C | D171G | 368 438 | 50 796 | 0.8788 |

Abbreviations: ECS, error-corrected sequencing; RFs, read families; VAF, variant allele fraction. Two to seven mutations were queried per individual and the number of read families containing the variant allele or reference allele were reported and used to calculate the variant allele fraction.

TABLE 2

Random 16-mer molecular indexed adapters. The terminal 5-prime phosphorylation on complementary adapter sequence was used to improve ligation efficiency (*).

| Label | Sequence | SEQ ID NO: |
|---|---|---|
| 16N Index Adapter | AGACGGCATACGAGATNNNNNNNNNNNNNNNNGTGACTGGAGTTCAGACGTGTGCTCTTCCGATCT | 1 |
| Complementary Adapter | *GATCGGAAGAGCGTCGTGTAGGGAAAGAGTGTAGATCTCGGTGGTCGCCGTATCATT | 2 |

TABLE 3

Whole-genome sequencing of diagnosis t-AML/t-MDS samples.

| UPN | Gene | Chr | Position | Mutation | AA Change | Reference Reads | Variant Reads | VAF |
|---|---|---|---|---|---|---|---|---|
| 446294 | OBSCN | 1 | 228461129 | A to G | H1857R | 3 | 5 | 0.63 |
| | TP53 | 17 | 7578271 | T to A | H193L | 79 | 106 | 0.57 |
| 499258 | RUNX1 | 21 | 36252865 | C to G | R139P | 122 | 17 | 0.12 |
| 574214 | DMD | X | 32827676 | G to A | R187* | 103 | 73 | 0.41 |
| 643006 | ASXL1 | 20 | 31022448 | G to T | G645C | 36 | 32 | 0.47 |
| | ASXL1 | 20 | 31022442 | del G | G645fs | 33 | 32 | 0.49 |
| | GATA2 | 3 | 128200135 | del CTT | K390in_frame_de | 8 | 10 | 0.56 |
| | U2AF1 | 21 | 44524456 | G to T | S34Y | 24 | 27 | 0.53 |
| 684949 | ASXL1 | 20 | 31023112 | T to G | L866* | 75 | 14 | 0.16 |
| | U2AF1 | 21 | 44524456 | G to T | S34Y | 57 | 9 | 0.14 |
| 856024 | S100A4 | 1 | 153517192 | A to G | F27L | 103 | 48 | 0.32 |
| | IGSF8 | 1 | 160062252 | G to A | P516S | 28 | 42 | 0.60 |
| | PLA2R1 | 2 | 160798389 | A to G | L1431P | 45 | 33 | 0.42 |
| | POU3F2 | 6 | 99282794 | C to A | S15R | 15 | 15 | 0.50 |
| | ANKRD18 | 9 | 33524645 | G to A | C53Y | 26 | 20 | 0.43 |
| | ESR2 | 14 | 64701847 | G to A | A416V | 40 | 22 | 0.35 |
| | FBN3 | 19 | 8155081 | G to A | P2029L | 54 | 38 | 0.41 |
| 942008 | IDH2 | 15 | 90631934 | C to T | R88Q | 10 | 10 | 0.50 |
| | RUNX1 | 21 | 36231791 | T to C | D171G | 15 | 35 | 0.70 |

TABLE 4

Summary of patient information. The type of primary malignancy, the date of primary malignancy diagnosis, the date and type of blood/bone marrow banked prior to t-AML/t-MDS diagnosis and the date of t-AML/t-MDS diagnosis are included in the table below. At t-AML/t-MDS diagnosis, tumor/normal whole genome sequencing identified leukemia-specific mutations. Some of the prior banked blood/bone marrow samples showed evidence of subclonal populations harboring those leukemia-specific mutations before the clinical detection of disease.

| UPN | Primary Malignancy Diagnosis | Date Primary Malignancy | Banked Samples | Banking Type | Date Banked | t-AML/t-MDS Diagnosis | Evidence of Pre-Leukemic Subclones |
|---|---|---|---|---|---|---|---|
| 446294 | Breast cancer | 2002 | 75.02 | FFPE | July 2005 | 2006 (t-MDS) | Yes |
| 499258 | Hodgkin's | 1998 | 24.06 | Cryo | February 2002 | 2004 (t-MDS) | No |
| 574214 | Breast cancer | 1998 | 26.04 | Cryo | January 2000 | 2007 (t-MDS) | No |
| 643006 | AML | 1989 | 80.01 | FFPE | April 1992 | 2004 (t-MDS) | Yes |
| 684949 | CLL | September 1991 | 91.01 | FFPE | November 2002 | 2007 (t-MDS) | Yes |
|  |  |  | 92.02 | FFPE | September 2003 |  | Yes |
|  |  |  | 93.01 | FFPE | October 2004 |  | Yes |
| 856024 | NHL | November 2004 | 30.02 | Cryo | March 2005 | 2006 (t-AML) | No |
| 942008 | NHL | August 1992 | 33.04 | Cryo | September 1996 | 2005 (t-AML) | Yes |
|  |  |  | 107.01 | FFPE | November 2005 |  | Yes |

TABLE 5

Primers targeting leukemia-specific variants. Primer sequences used to generate variant-specific amplicons from banked genomic DNA samples.

| UPN | Gene | FWD Primer | SEQ ID NO: | Reverse Primer | SEQ ID NO: |
|---|---|---|---|---|---|
| 446294 | OBSCN | GGAGCCTCTGACCCTGCATCCCTCC | 3 | CCCGCCTCACAGCTGTACTCCCCAG | 4 |
|  | TP53 | AGACCTCAGGCGGCTCATAGGGCAC | 5 | GGGGCTGGAGAGACGACAGGGCTG | 6 |
| 499258 | RUNX1 | TCACTAGAATTTTGAAATGTGGGTTTGTTGCC | 7 | GCACTCTGGTCACTGTGATGGCTGGC | 8 |
| 574214 | DMD | GGCGATGTTGAATGCATGTTCCAGT | 9 | AGGACTATGGGCATTGGTTGTCAAT | 10 |
| 643006 | ASXL1 | GGACCCTCGCAGACATTAAAGCCCGT | 11 | GCCTCACCACCATCACCACTGCTGC | 12 |
|  | GATA2 | CCACAGGTGCCATGTGTCCAGCCAG | 13 | CTGTGGCGGGGTGGGAGGAATGTTG | 14 |
|  | U2AF1 | TGAACACAAATGGAAAATACAACTACGAGAGAAAA | 15 | CCCAGCAAAATAATCAGCTCTCATTTTCCC | 16 |
| 684949 | ASXL1 | CACTATGAAGGATCCTGTAAATGTGACCCC | 17 | TGGTTTGGGCTGTTTCACTACCTCA | 18 |
|  | U2AF1 | TGAACACAAATGGAAAATACAACTACGAGAGAAAA | 15 | CCCAGCAAAATAATCAGCTCTCATTTTCCC | 16 |
| 856024 | S100A4 | CCACGTGGGGACTCACTCAGGCA | 19 | AATAAGACGGTCTCTGTGCCTCCTG | 20 |
|  | IGSF8 | TGGTACACGCCTTCATCCTCGGG | 21 | GCTCAGCTCTGTCCCTGCCCAGCT | 22 |
|  | PLA2R1 | ACCCTGGTGTCTGTGGCATTCTCTG | 23 | AGTCACAGCATCATTCCTCTTGCGGT | 24 |
|  | POU3F2 | CAAATGCGCGGCTCCTTTAACCGGA | 25 | GCGTGGCTGAGCGGGTGTCC | 26 |
|  | ANKRD18B | TACCACATTCGGGACTGGGAACTGC | 27 | CTCCCAGGGTCCCGGCGAACTCC | 28 |

TABLE 5-continued

Primers targeting leukemia-specific variants. Primer sequences used to generate variant-specific amplicons from banked genomic DNA samples.

| UPN | Gene | FWD Primer | SEQ ID NO: | Reverse Primer | SEQ ID NO: |
|---|---|---|---|---|---|
| | ESR2 | TGGCAATCACCCAAACCAAAGCATCGGT | 29 | AACCCAGATCACCTCGGAGCAGGCG | 30 |
| | FBN3 | GGGGACACAGTTCGCAGGGGTC | 31 | GACTGGGGTGCGGGAGGTCACAGG | 32 |
| 942008 | IDH2 | GGCGTGCCTGCCAATGGTGATGGG | 33 | CCGTCTGGCTGTGTTGTTGCTTGGGG | 34 |
| | RUNX1 | ACATGGTCCCTGAGTATACCAGCCT | 35 | GGCCACCAACCTCATTCTGTTTTGT | 36 |

REFERENCES FOR EXAMPLE 1

1 Holstege H, Pfeiffer W, Sie D, Hulsman M, Nicholas T J, Lee C C et al. Somatic mutations found in the healthy blood compartment of a 115-yr-old woman demonstrate oligoclonal hematopoiesis. *Genome Res* 2014; 24: 733-742.
2 Walter M J, Shen D, Ding L, Shao J, Koboldt D C, Chen K et al. Clonal architecture of secondary acute myeloid leukemia. *N Engl J Med* 2012; 366: 1090-1098.
3 Welch J S, Ley T J, Link D C, Miller C A, Larson D E, Koboldt D C et al. The Origin and Evolution of Mutations in Acute Myeloid Leukemia. *Cell* 2012; 150: 264-278.
4 Schmitt M W, Kennedy S R, Salk J J, Fox E J, Hiatt J B, Loeb L A. Detection of ultra-rare mutations by next-generation sequencing. *Proc Natl Acad Sci USA* 2012; 109: 14508-14513.
5 Kinde I, Wu J, Papadopoulos N, Kinzler K W, Vogelstein B. Detection and quantification of rare mutations with massively parallel sequencing. *Proc Natl Acad Sci USA* 2011; 108: 9530-9535.
6 Godley L A, Larson R A. Therapy-related myeloid leukemia. *Semin Oncol* 2008; 35: 418-429.
7 Wong T, Ramsingh G, Young A L, Miller C A, Touma W, Welch J S et al. The role of TP53 mutations in the origin and evolution of therapy-related AML. *Nature* 2015; 518: 552-555.
8 Fu G K, Xu W, Wilhelmy J, Mindrinos M N, Davis R W, Xiao W et. al. Molecular indexing enables quantitative targeted RNA sequencing and reveals poor efficiencies in standard library preparations. *Proc Natl Acad Sci USA* 2014; 111: 1891-1896.
9 Lou D I, Hussmann Ja, McBee R M, Acevedo A, Andino R, Press W H et al. High-throughput DNA sequencing errors are reduced by orders of magnitude using circle sequencing. *Proc Natl Acad Sci USA* 2013; 110: 19872-19877.
10 Cancer Genome Atlas Research Network. Genomic and epigenomic landscapes of adult de novo acute myeloid leukemia. *N Engl J Med* 2013; 368: 2059-2074.
11 Salipante S J, Fromm J R, Shendure J, Wood B L, Wu D. Detection of minimal residual disease in NPM1-mutated acute myeloid leukemia by next-generation sequencing. *Mod Pathol* 2014; 27: 1438-1446.
12 Kohlmann a, Nadarajah N, Alpermann T, Grossmann V, Schindela S, Dicker F et al. Monitoring of residual disease by next-generation deep-sequencing of RUNX1 mutations can identify acute myeloid leukemia patients with resistant disease. *Leukemia* 2014; 28: 129-137.
13 Loman N J, Misra R V, Dallman T J, Constantinidou C, Gharbia S E, Wain J et al. Performance comparison of benchtop high-throughput sequencing platforms. *Nat Biotechnol* 2012; 30: 434-439.
14 Hourigan C S, Karp J E. Minimal residual disease in acute myeloid leukaemia. *Nat Rev Clin Oncol* 2013; 10: 460-471.

REFERENCES FOR THE METHODS FOR EXAMPLE 1

1 Untergasser A, Cutcutache I, Koressaar T, Ye J, Faircloth B C, Remm M et al. Primer3—new capabilities and interfaces. *Nucleic Acids Res* 2012; 40: e115.
2 Forshew T, Murtaza M, Parkinson C, Gale D, Tsui D W Y, Kaper F et al. Noninvasive identification and monitoring of cancer mutations by targeted deep sequencing of plasma DNA. *Sci Transl Med* 2012; 4: 136ra68.
3 Langmead B, Salzberg S L. Fast gapped-read alignment with Bowtie 2. *Nat Methods* 2012; 9: 357-9.
4 Kinde I, Wu J, Papadopoulos N, Kinzler K W, Vogelstein B. Detection and quantification of rare mutations with massively parallel sequencing. *Proc Natl Acad Sci USA* 2011; 108: 9530-5.
5 Schmitt M W, Kennedy S R, Salk J J, Fox E J, Hiatt J B, Loeb L a. Detection of ultra-rare mutations by next-generation sequencing. *Proc Natl Acad Sci USA* 2012; 109: 14508-13.
6 Li H, Handsaker B, Wysoker A, Fennell T, Ruan J, Homer N et al. The Sequence Alignment/Map format and SAMtools. *Bioinformatics* 2009; 25: 2078-9.
7 Thorvaldsdóttir H, Robinson J T, Mesirov J P. Integrative Genomics Viewer (IGV): high-performance genomics data visualization and exploration. *Brief Bioinform* 2013; 14: 178-92.
8 Wickham H. ggplot2. Springer New York: New York, N.Y., 2009 doi:10.1007/978-0-387-98141-3.

Example 2. MRD Testing in AML Using Error-Corrected Sequencing

In acute myeloid leukemia (AML), minimal residual disease (MRD) testing following treatment is accomplished using multiparameter flow cytometry, which targets clonal cell surface markers; or qPCR, which targets leukemia-associated chromosomal translocations. While both methods provide prognostic information to a detection limit of 1:10,000 cells, these methods are useful in only a subset of leukemia patients[1-3]. Conversely, leukemia-specific somatic mutations occur in virtually every case of AML and present a potential target for residual disease assessment[4,5]. Our goal is to develop a sequencing-based platform to detect rare leukemic cells by their unique somatic mutation profile. Currently, next-generation sequencing is not sensitive enough to detect rare somatic mutations due to a 1% error rate. Fortunately, we have adapted methods for error-corrected sequencing (ECS) to circumvent this limitation[6-9]. Here, we have extended these methods for ECS with leukemia-specific genomic DNA capture to attempt to detect rare (<1%) persistent leukemic cells regardless of their specific somatic mutation profile.

Remission blood samples from 15 individuals treated for de novo AML were acquired. Subclonal somatic mutations in the remission samples were then identified. These results were used to quantify the burden of persistent leukemia. The results obtained were compared to conventional NGS and clinical findings.

Figure 9A:
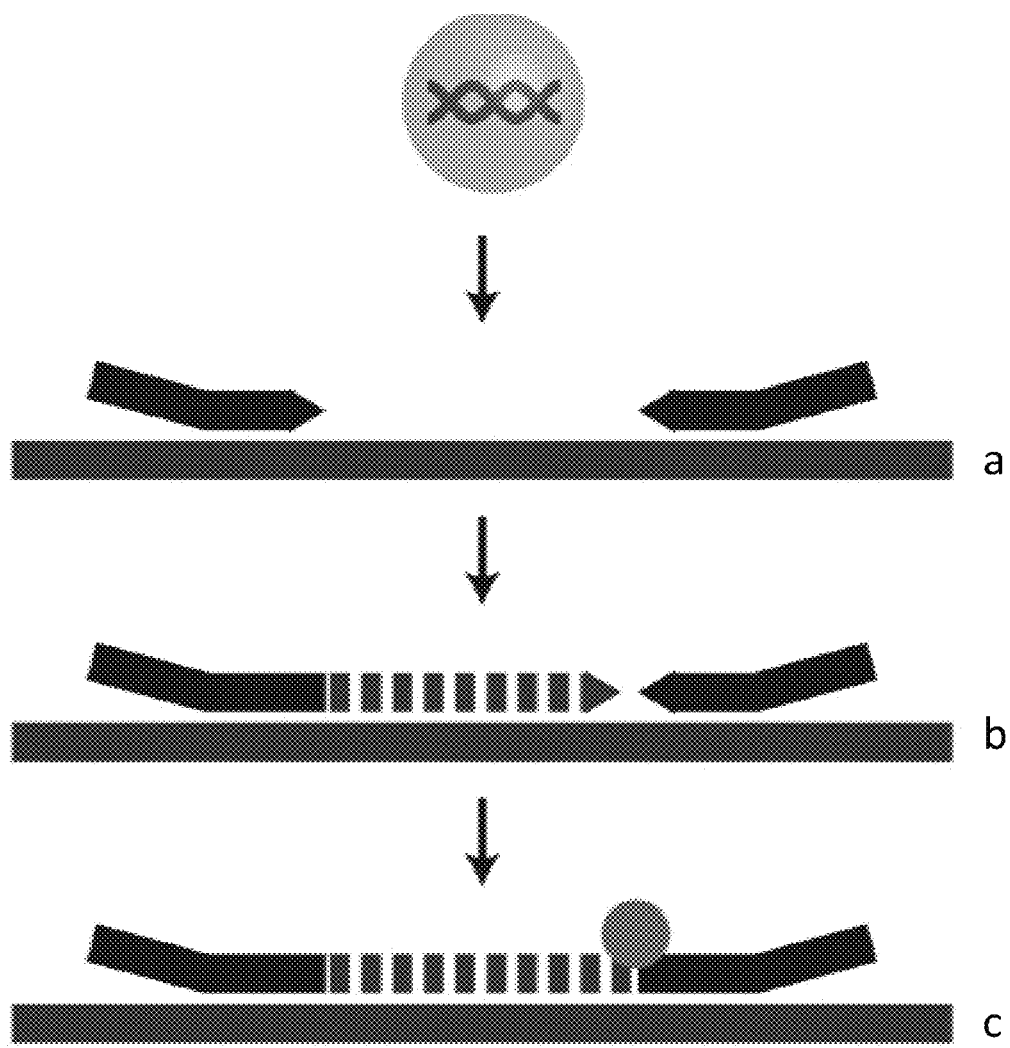
FIGS. 9A and 9B depict a method of multiplex targeted genomic capture using the error-corrected sequencing methodology.
Figure 9B:
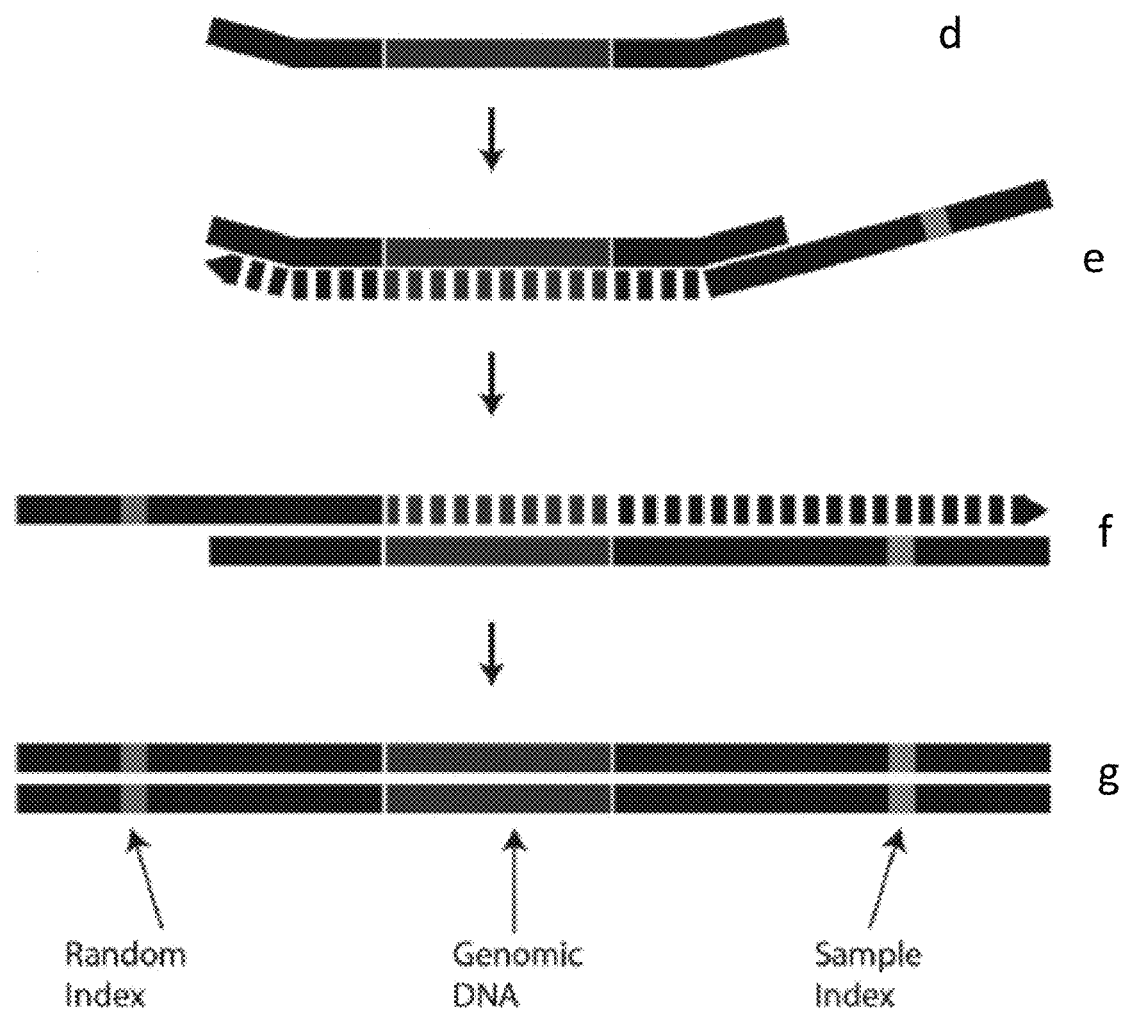

To facilitate leukemia-specific capture Illumina TruSight Myeloid Panel was used. The Panel captures 54 genes via 568 amplicons frequently mutated in AML and targets 141 kb of genomic DNA (Table 6). The Panel method is depicted in FIG. 9A, FIG. 9B.

Future directions involve further development of the TruSight capture/ECS protocol, assessment of persistent AML following treatment using leukemia-specific somatic mutations, and assessment of the role of rare subclones arising in the hematopoietic compartment of healthy individuals.

Figure 10A:
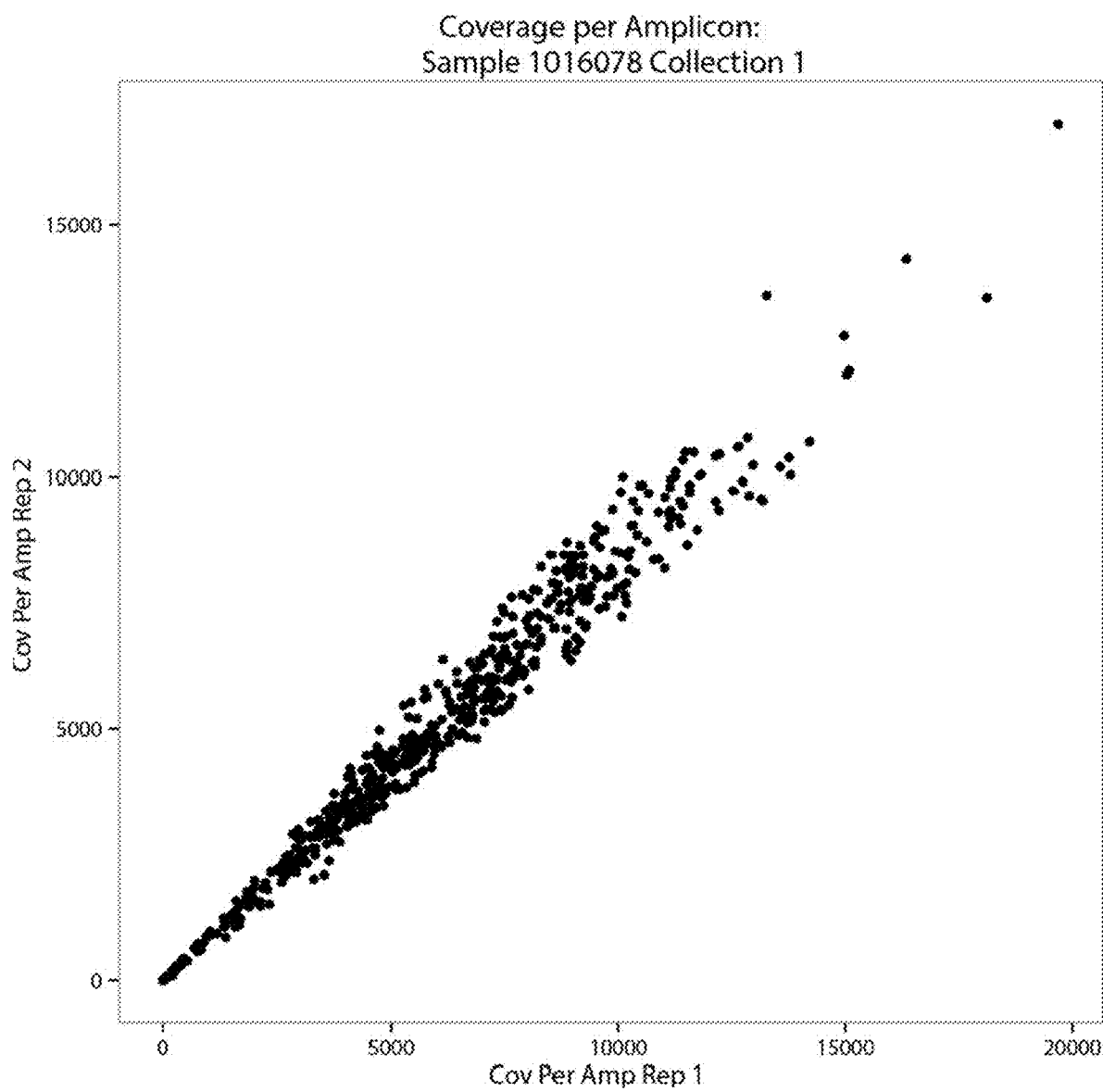
FIGS. 10A and 10B depict graphs showing that the amplicon coverage between replicates is correlated.
Figure 10B:
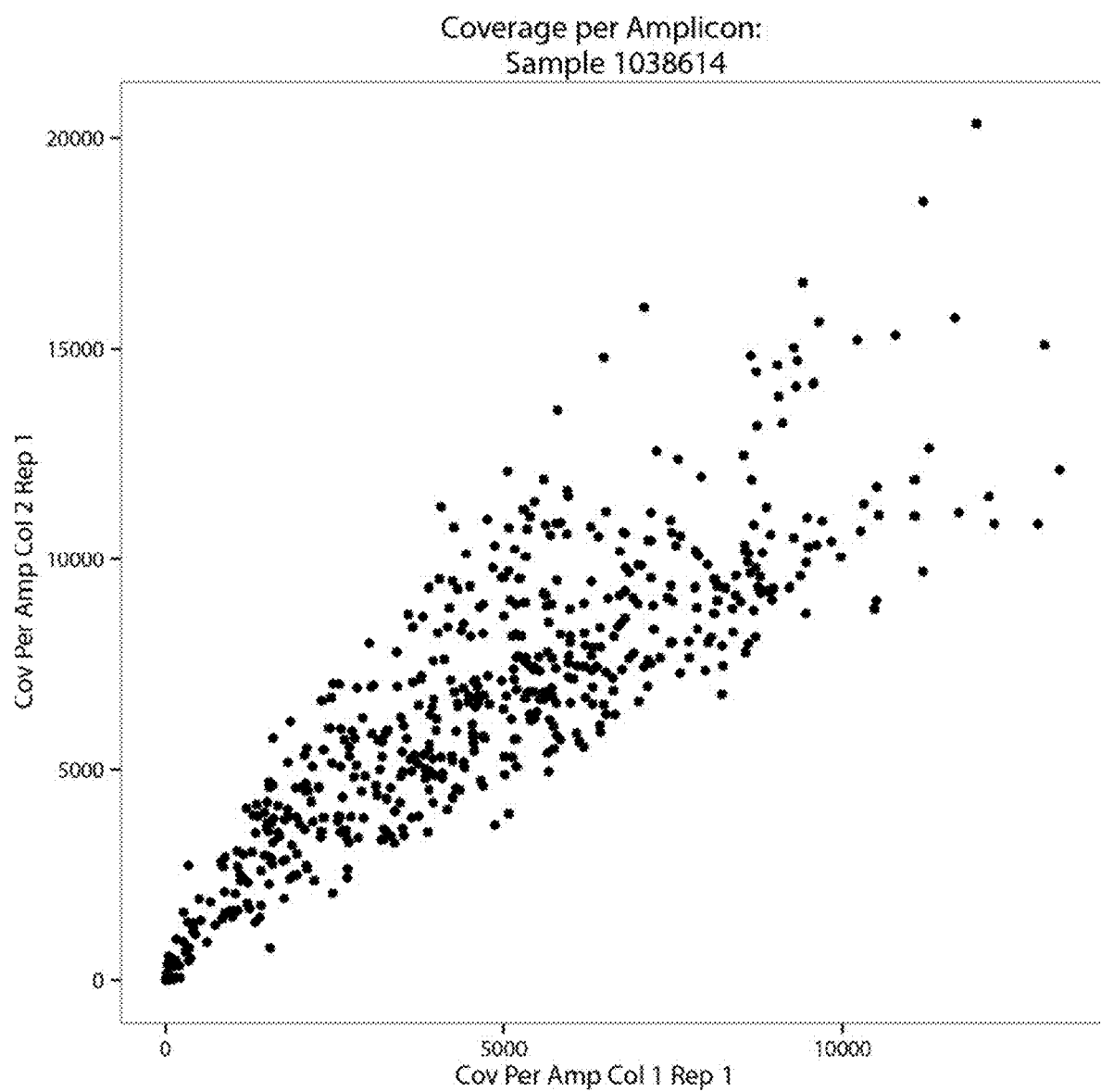
Figure 11:
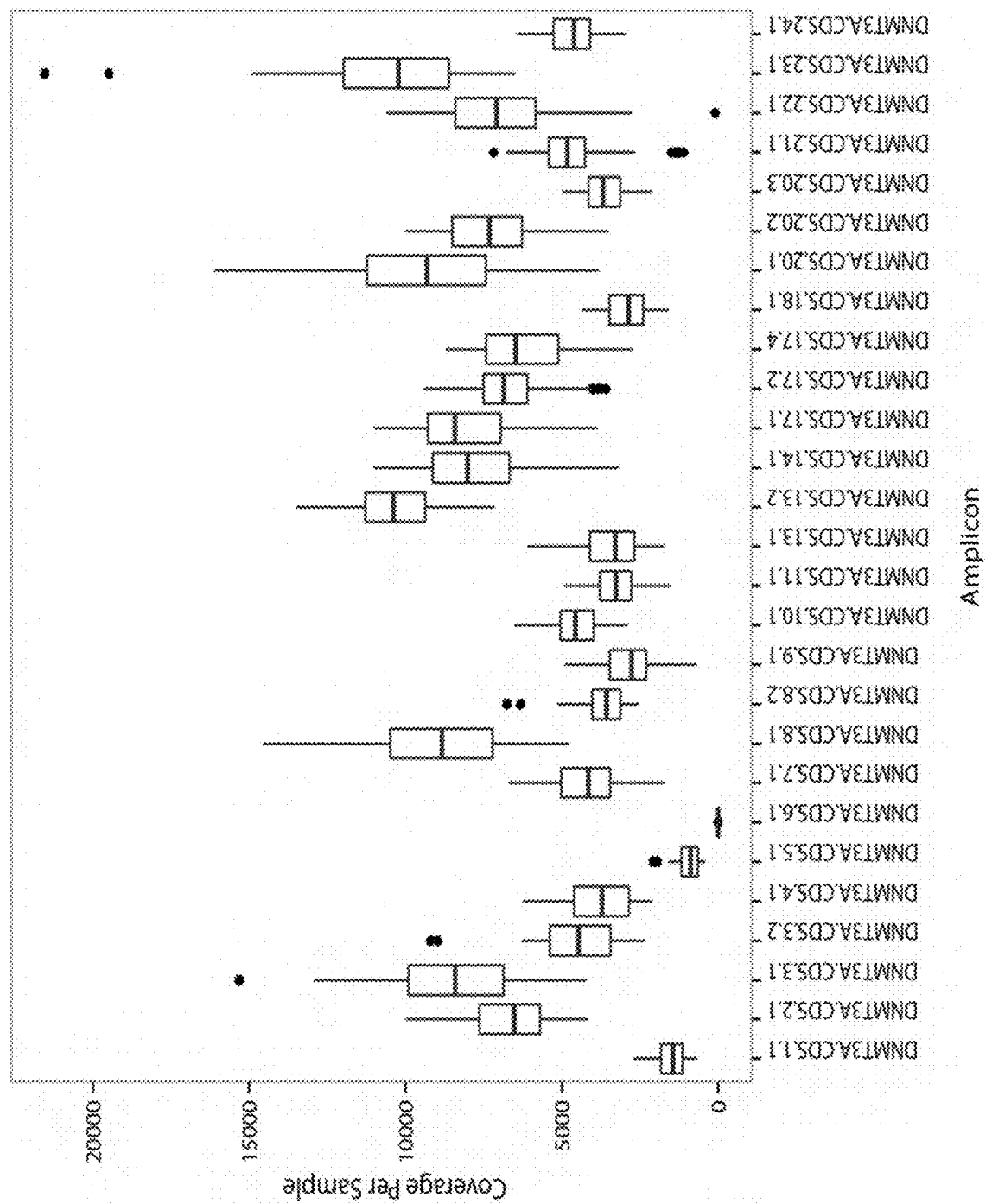
FIG. 11 depicts a graph showing that the coverage per amplicon is variable.

Example 3. Use of TruSight Myeloid Panel and ECS Protocol in a Clinical Study of Healthy Individuals In collaboration with the Nurses Healthy Study, 20 healthy elderly individuals were enrolled to examine the clinical possibilities of the TruSight Myeloid panel and ECS methodology. Paired buffy coat samples were banked 10 years apart. The average age at collection of the first sample was 57.1 years and the average age at collection of the second sample was 68.5. Samples were prepared in duplicate (80 libraries total) using the Illumina TruSight Myeloid panel and the ECS protocol. The samples were sequence on 10 NextSeq High Output (PE150) runs. Table 7 presents a summary of the sequencing results. The output per run was ~400M PE reads. Table 8 shows that the libraries appear to be mixed in equimolar ratios. There are approximately 3M read families per library. FIG. 10 shows that the amplicon coverage between replicates is correlated. FIG. 10A shows that two libraries sequenced on the same run (NHS1) had an R-squared value of 0.9718 and FIG. 10B shows that two libraries sequenced on different runs (NHS2, NHS6) had an R-squared value of 0.7536. FIG. 11, which presents data from DNMT3A, shows that the coverage per amplicon is variable.

TABLE 6

Coverage Details

| | |
|---|---|
| Cumulative target region size | ~141 kb |
| Number of target genes | 54 |
| Amplicon size | ~250 bp |
| Number of amplicons | 568 |
| Recommended mean coverage | 5,000x |
| Target minimum coverage | 500x |
| Percent exons covered at 500x | 95 |

TABLE 7

Summary of Sequencing Results.

| Library | Sequenced Reads |
|---|---|
| NHS1 | 364,776,941 |
| NHS2 | 331,997,319 |
| NHS3 | 361,510,360 |
| NHS4 | 387,756,648 |
| NHS5 | 468,765,873 |
| NHS6 | 433,606,686 |
| NHS7 | 435,037,421 |
| NHS8 | 516,437,915 |
| NHS9 | 519,524,765 |
| NHS10 | 495,292,729 |

TABLE 8

Summary of Sequencing Results.

| Library | Index | Demux Reads | Frac of Total | ECS RFs | Frac of Demux Reads |
|---|---|---|---|---|---|
| NHS1 | CACCACAC | 33,657,209 | 0.092 | 2,860,180 | 0.085 |
| NHS1 | ACAGTGGT | 33,448,218 | 0.092 | 2,804,567 | 0.084 |
| NHS1 | ACAAACGG | 33,392,978 | 0.092 | 2,784,229 | 0.083 |
| NHS1 | ACCCAGCA | 39,268,072 | 0.108 | 3,318,173 | 0.085 |
| NHS1 | ATCACGAC | 38,483,255 | 0.105 | 3,333,626 | 0.087 |
| NHS1 | CCCAACCT | 35,157,811 | 0.096 | 3,027,607 | 0.086 |
| NHS1 | AACCCCTC | 41,984,812 | 0.115 | 3,558,516 | 0.085 |
| NHS1 | CAGATCCA | 35,427,539 | 0.097 | 2,987,274 | 0.084 |

Figure 12:
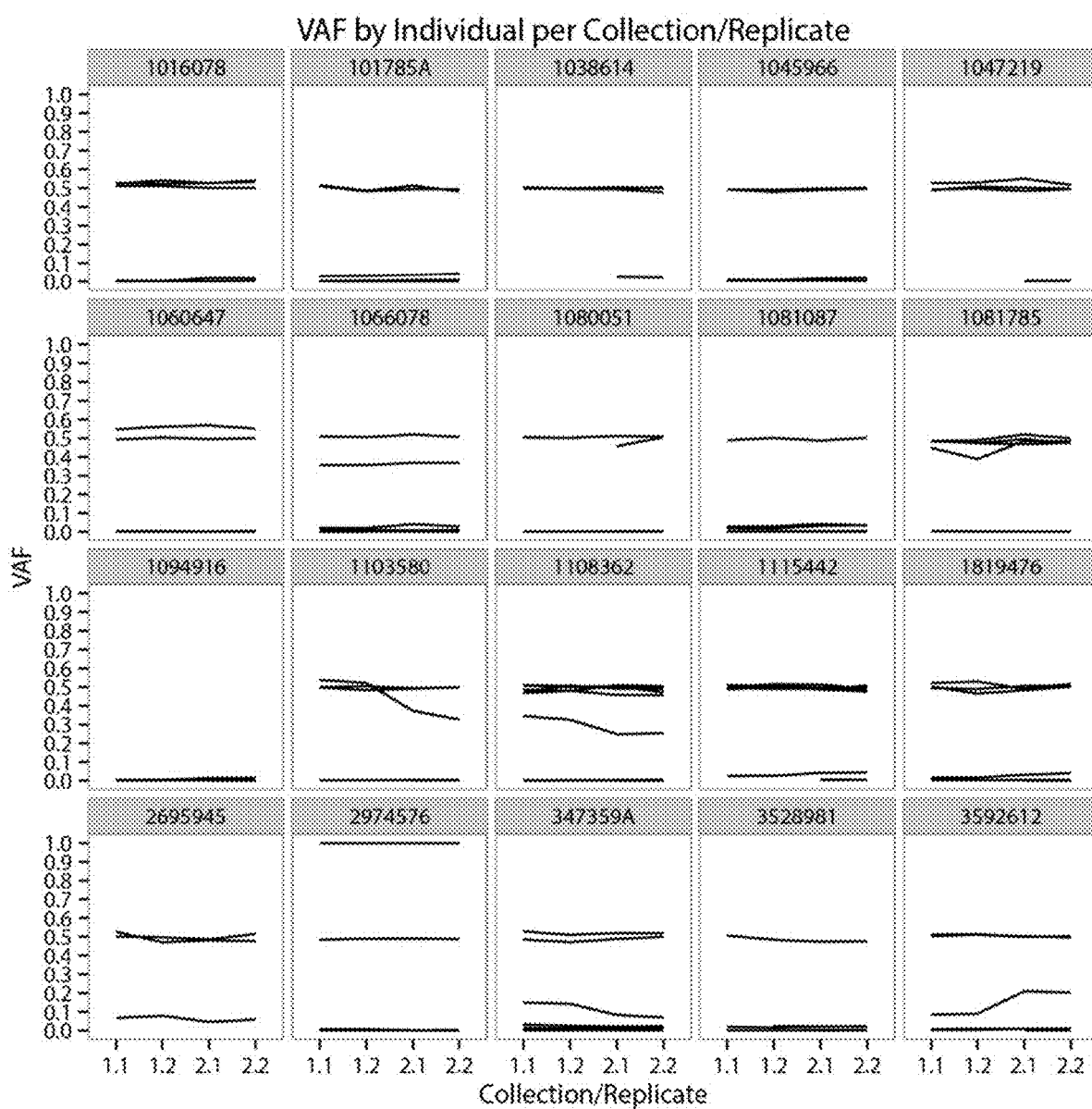
FIG. 12 depicts graphs showing the identification of constitutional and, importantly, rare SNVs in different samples. 49 germline (~0.5/1.0 VAF) SNVs were identified, 5 high VAF (0.14-0.36 VAF) SNVs were identified, and 106 low VAF (<0.1 VAF) SNVs were identified for a total of 160 SNVs identified.
Figure 13:
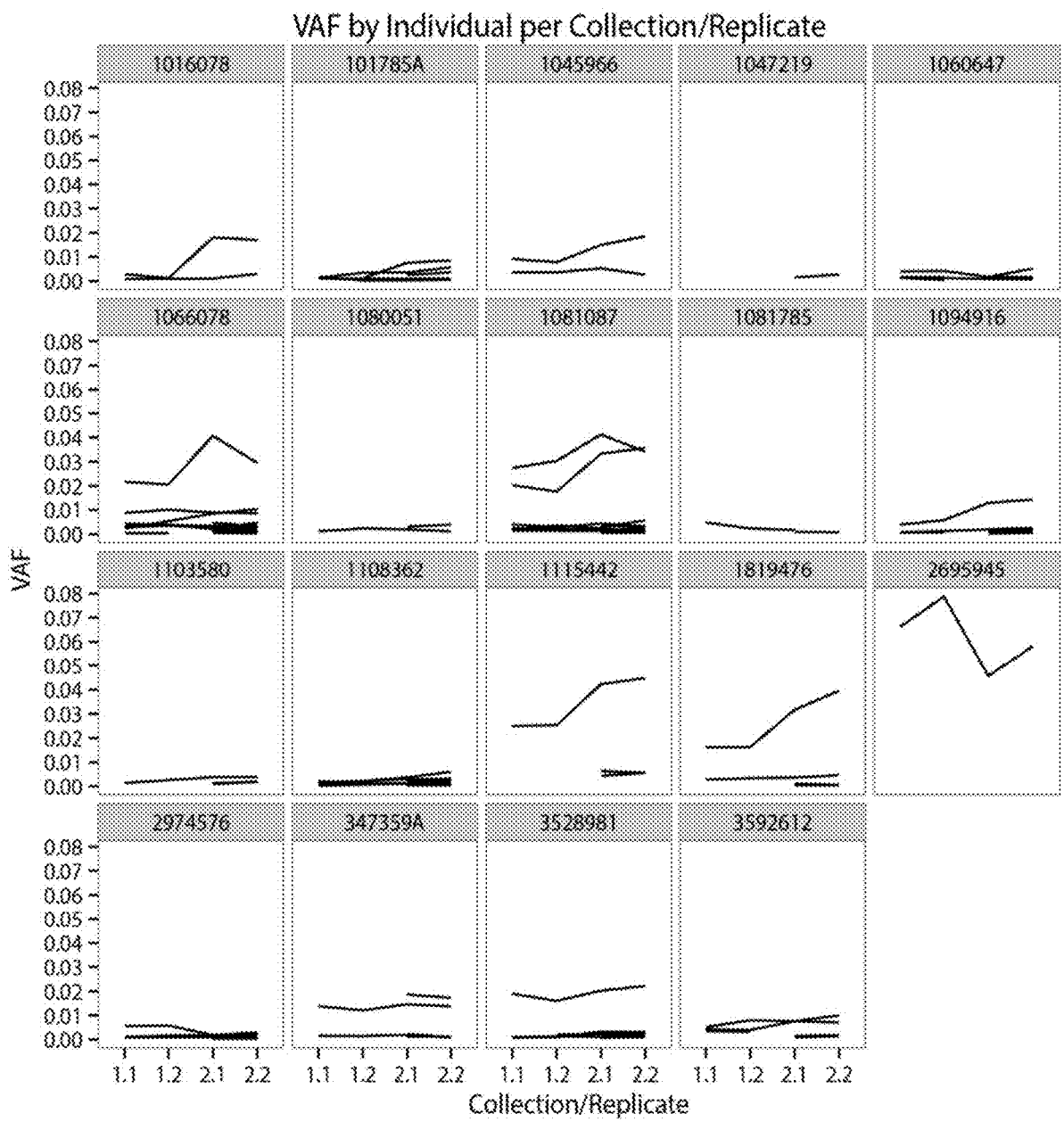
FIG. 13 depicts graphs showing that rare subclones are detected longitudinally in the same healthy individual.
Figure 14:
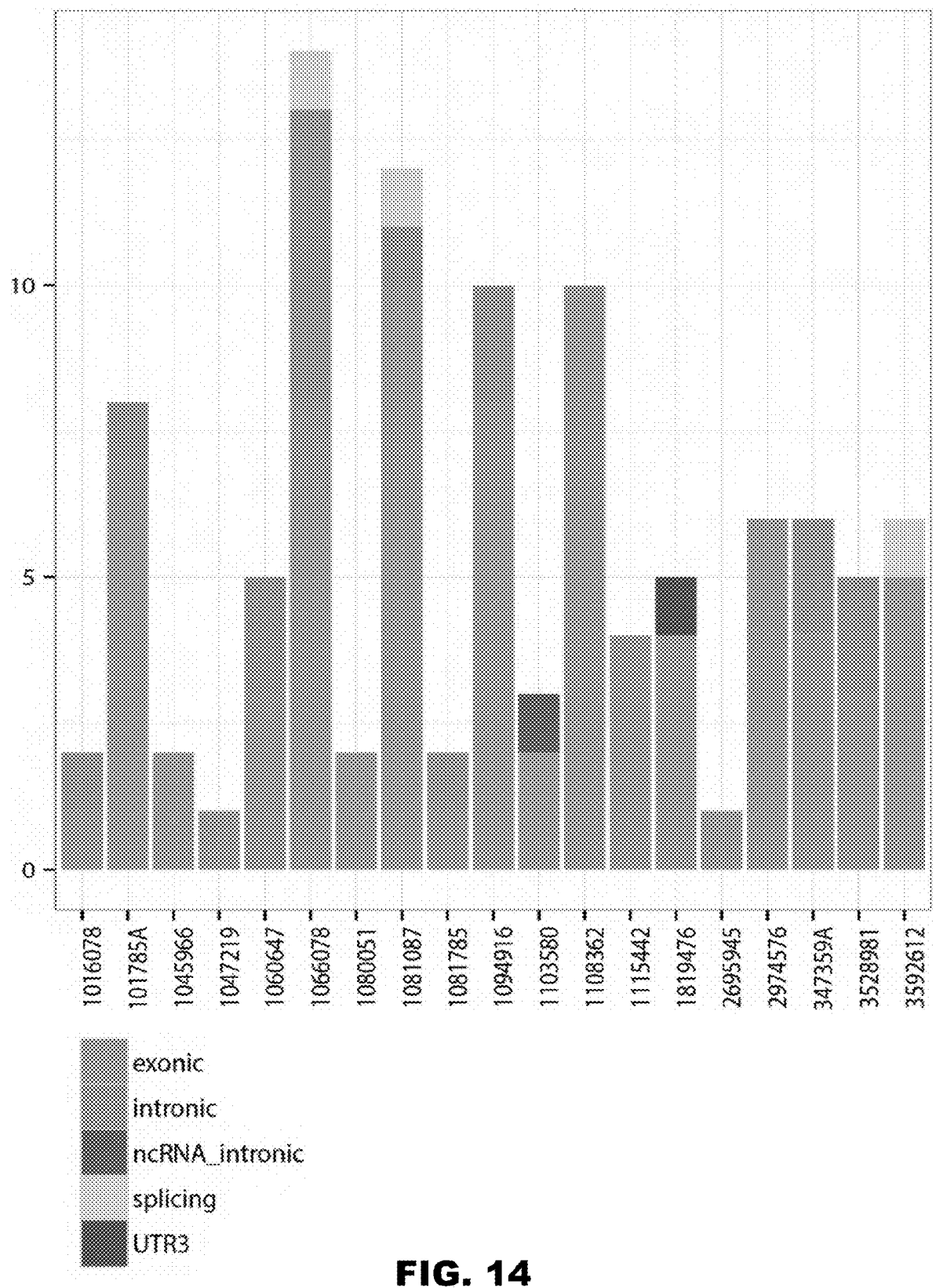
FIG. 14 depicts a graph showing that total rare subclonal variants detected per individual. The majority of the subclonal variants were detected in exonic regions.
Figure 15A:
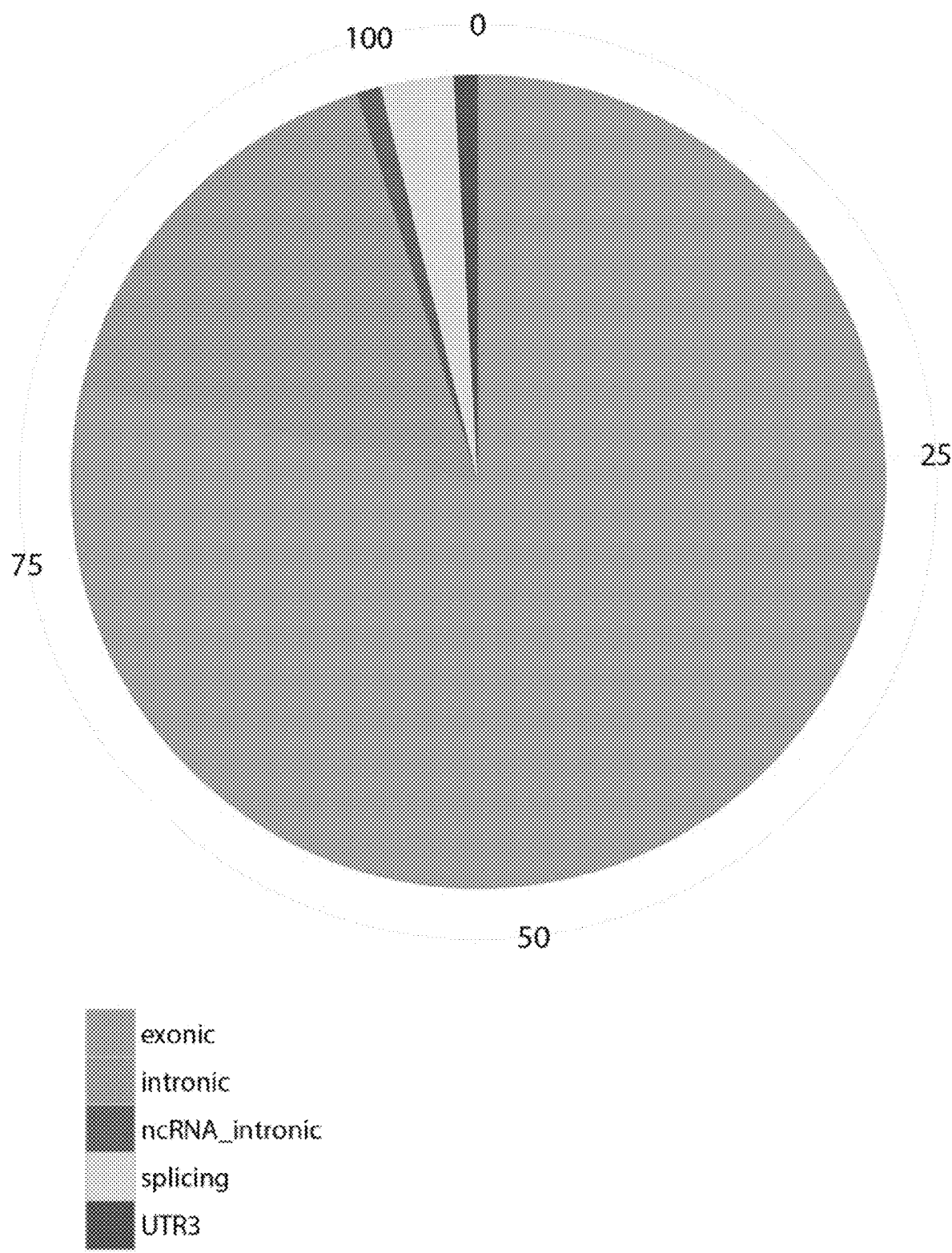
FIGS. 15A and 15B depict pie charts showing the classification of detected rare subclonal variants.
Figure 15B:
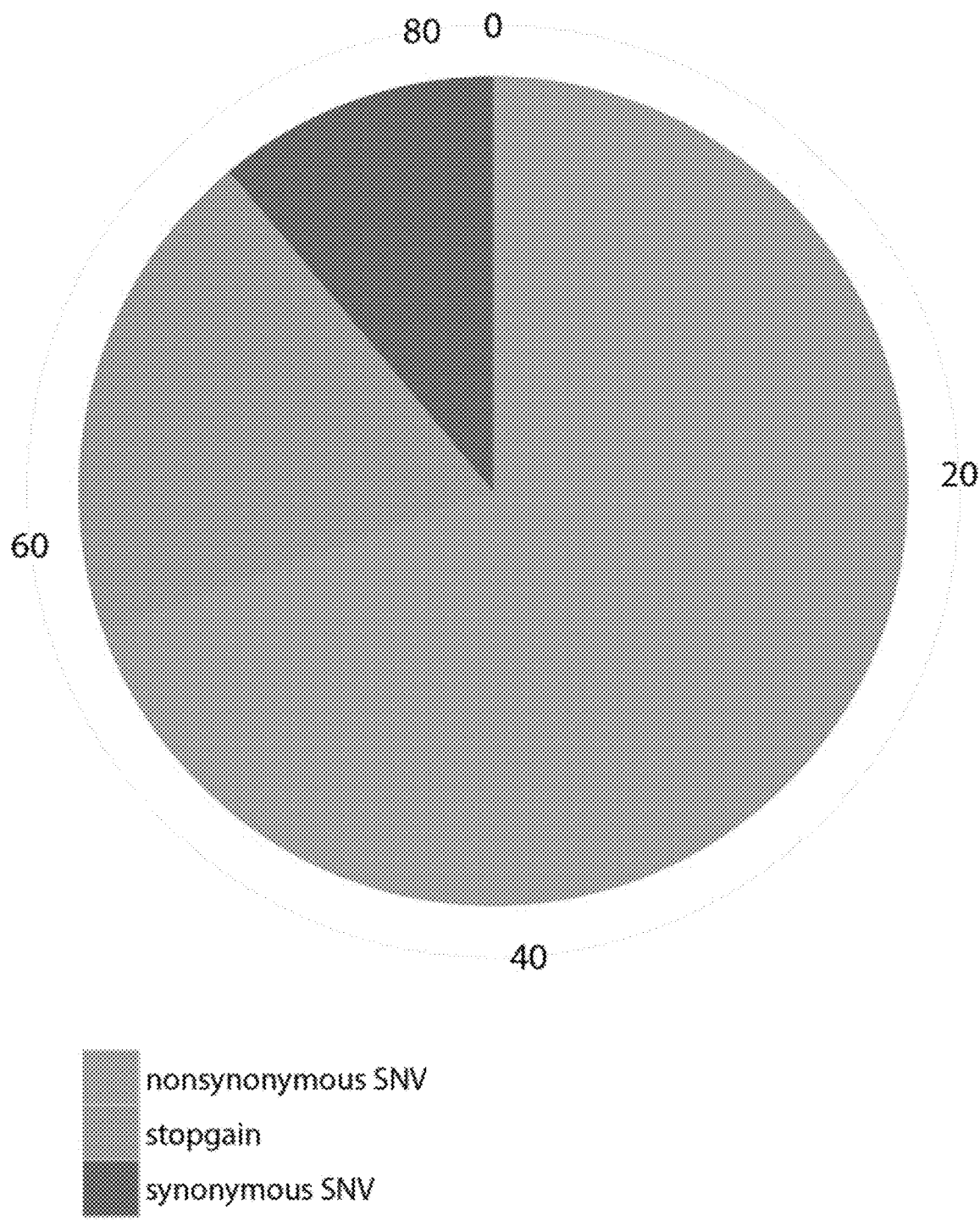
Figure 16:
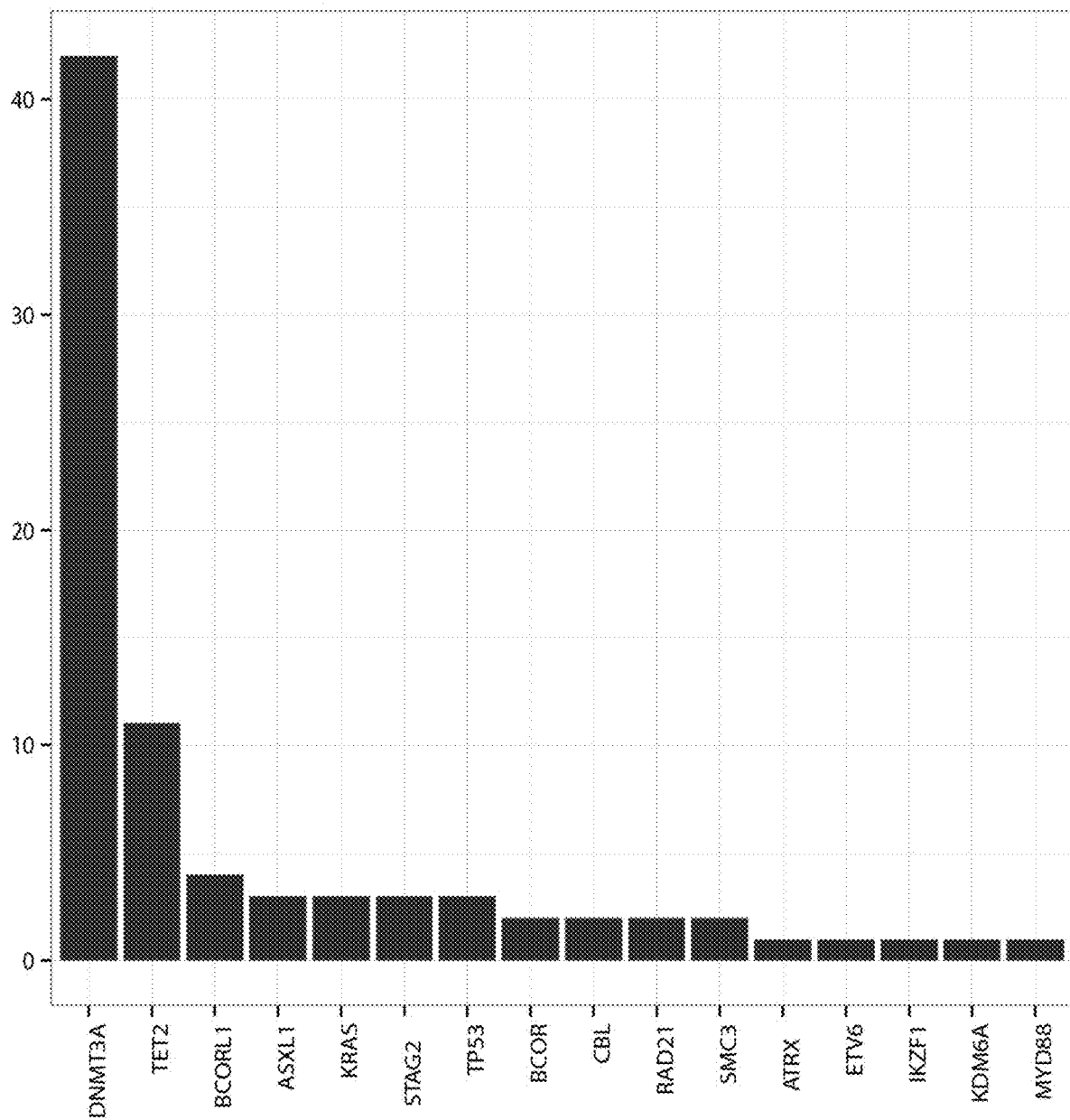
FIG. 16 depicts a graph showing that the detected exonic variants cluster in DNMT3A and TET2.
Figure 17:
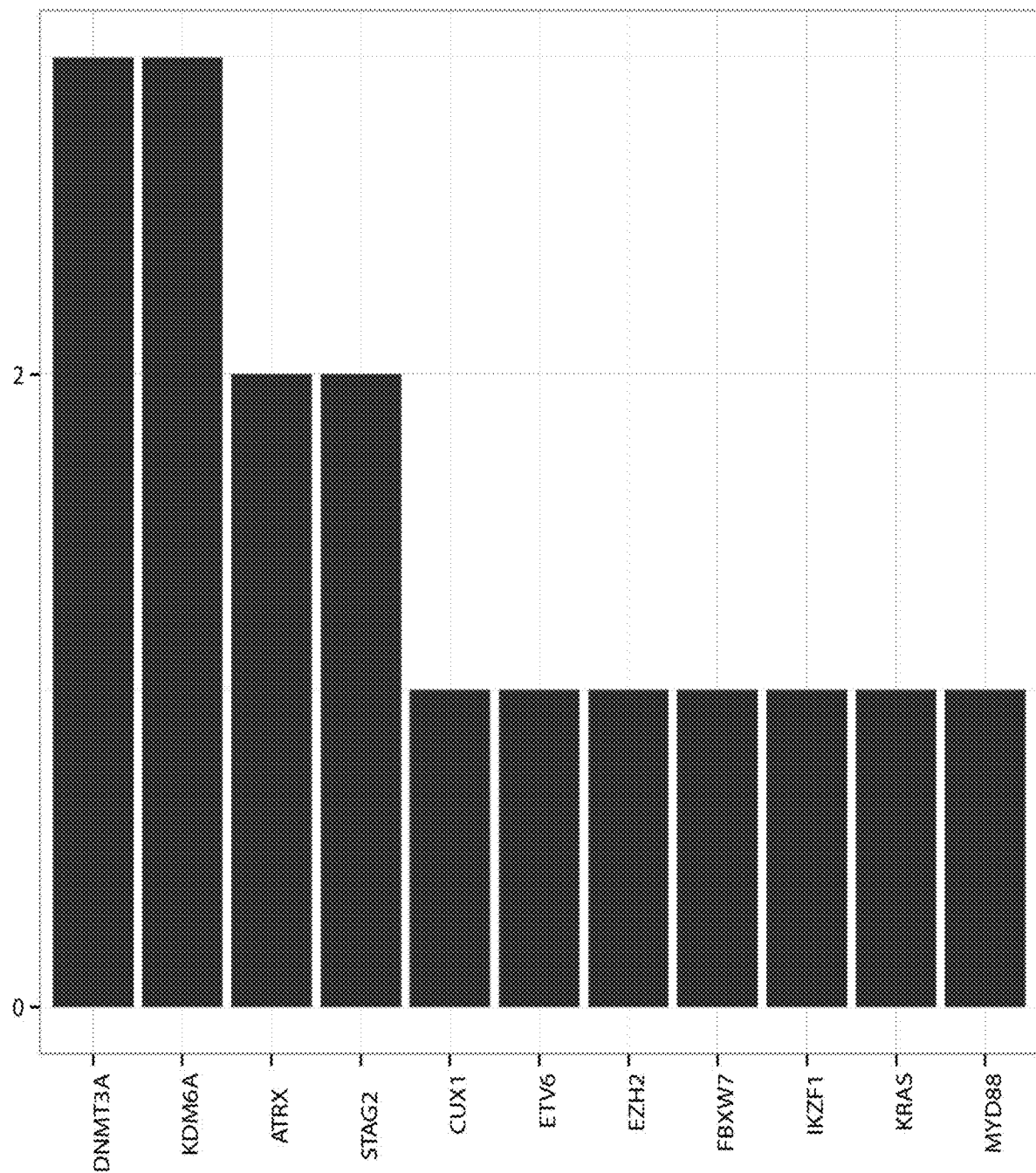
FIG. 17 depicts a graph showing that intronic variants are more evenly distributed.
Figure 18A:
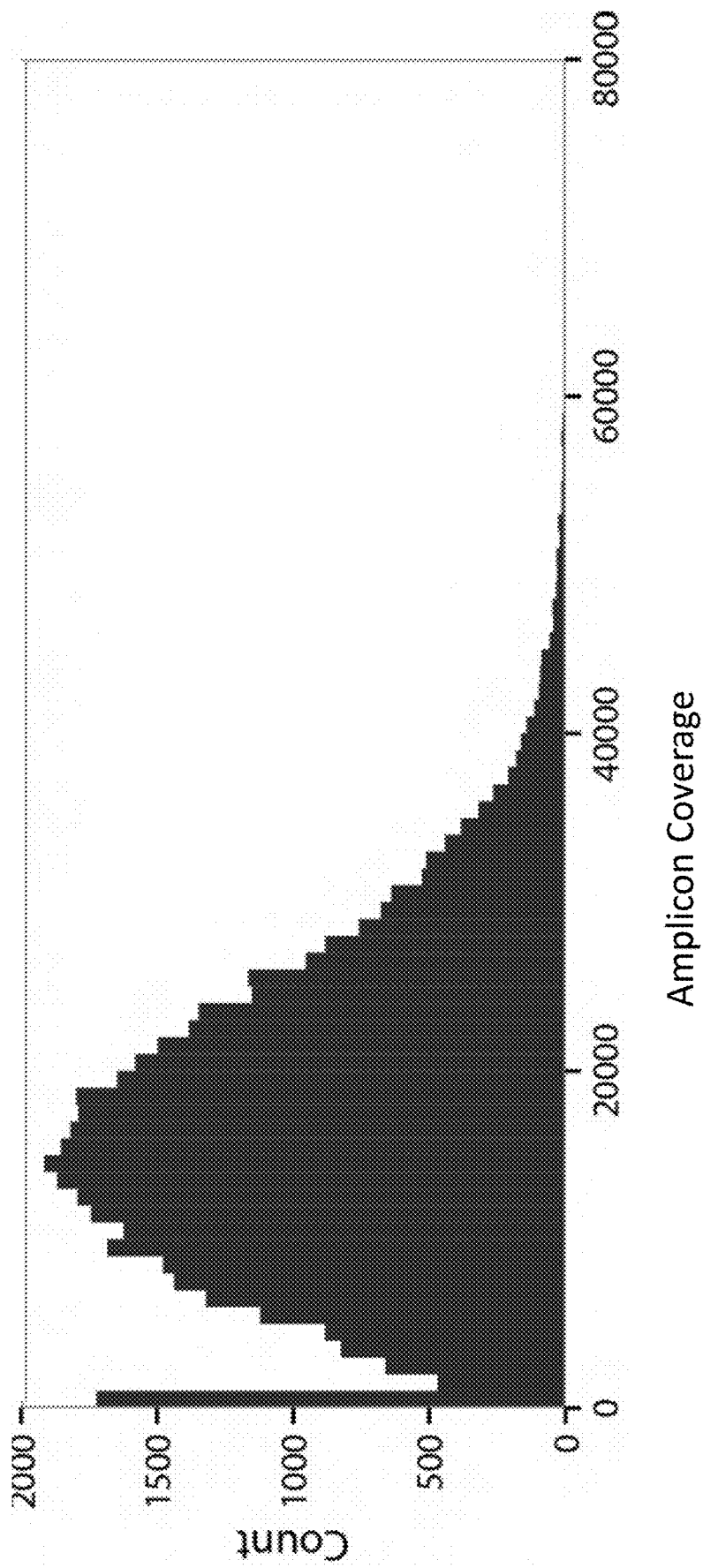
FIGS. 18A and 18B depict graphs show that the variants are not exclusively called in highly covered amplicons.
Figure 18B:
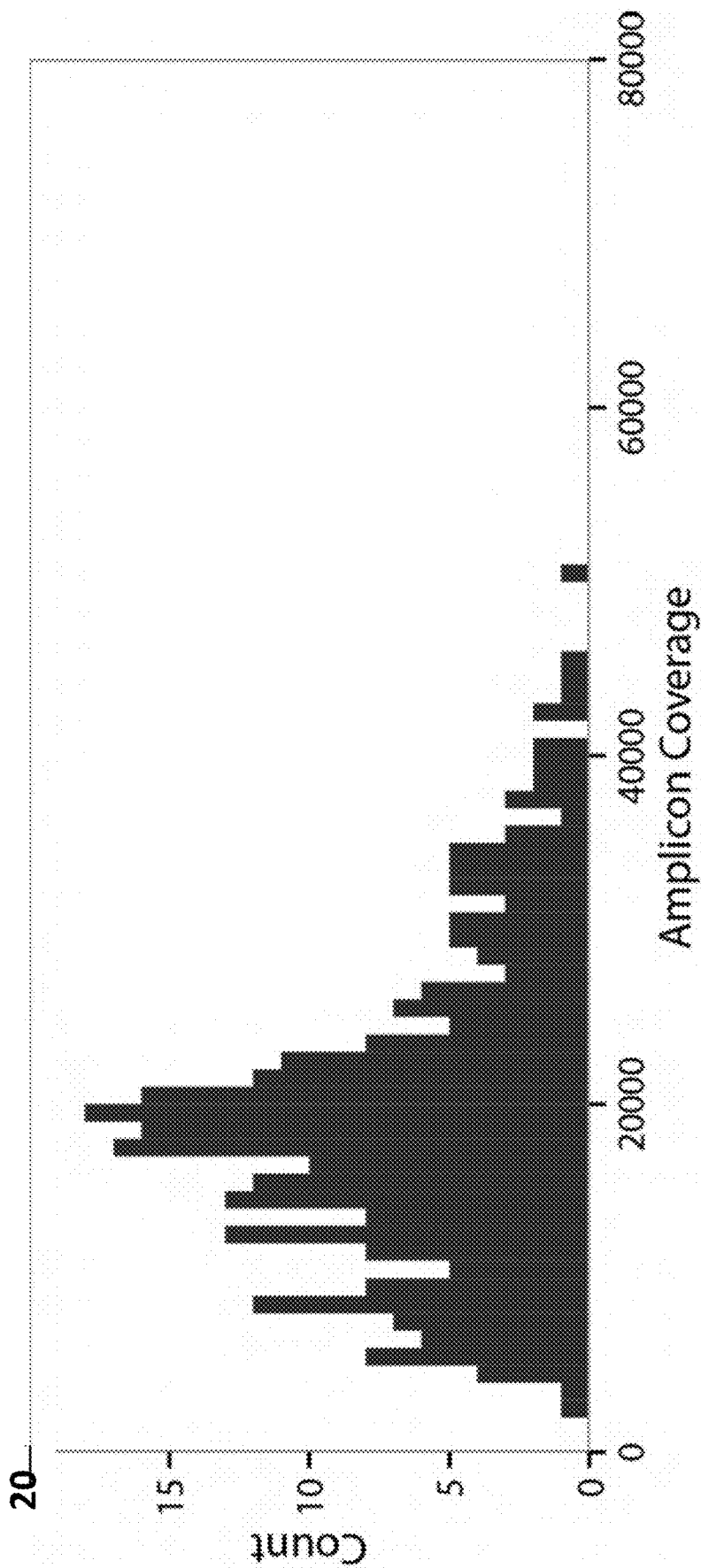
Figure 19A:
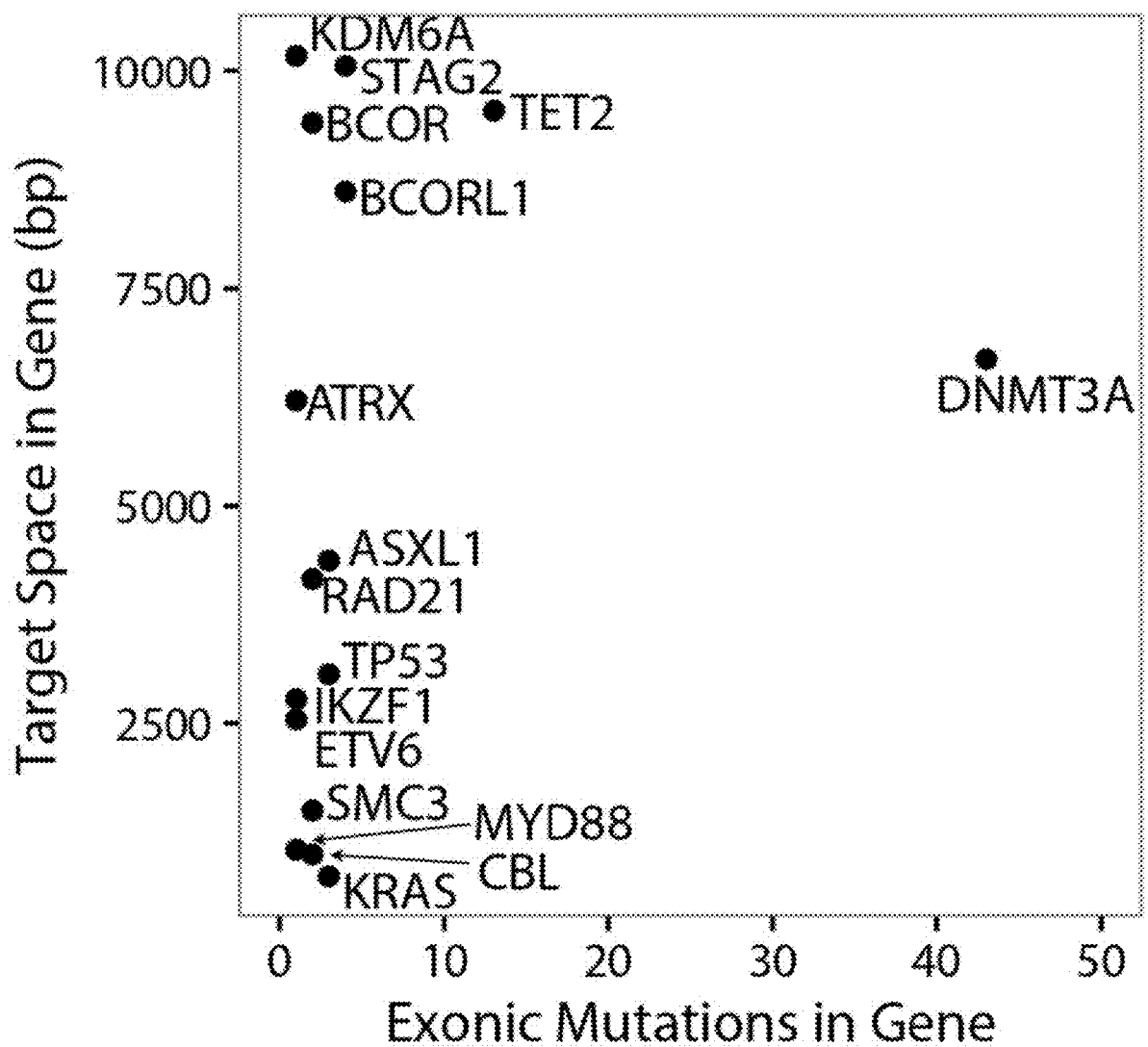
FIGS. 19A and 19B depict graphs showing the target space per gene does not correlated with SNV calls per gene.
Figure 19B:
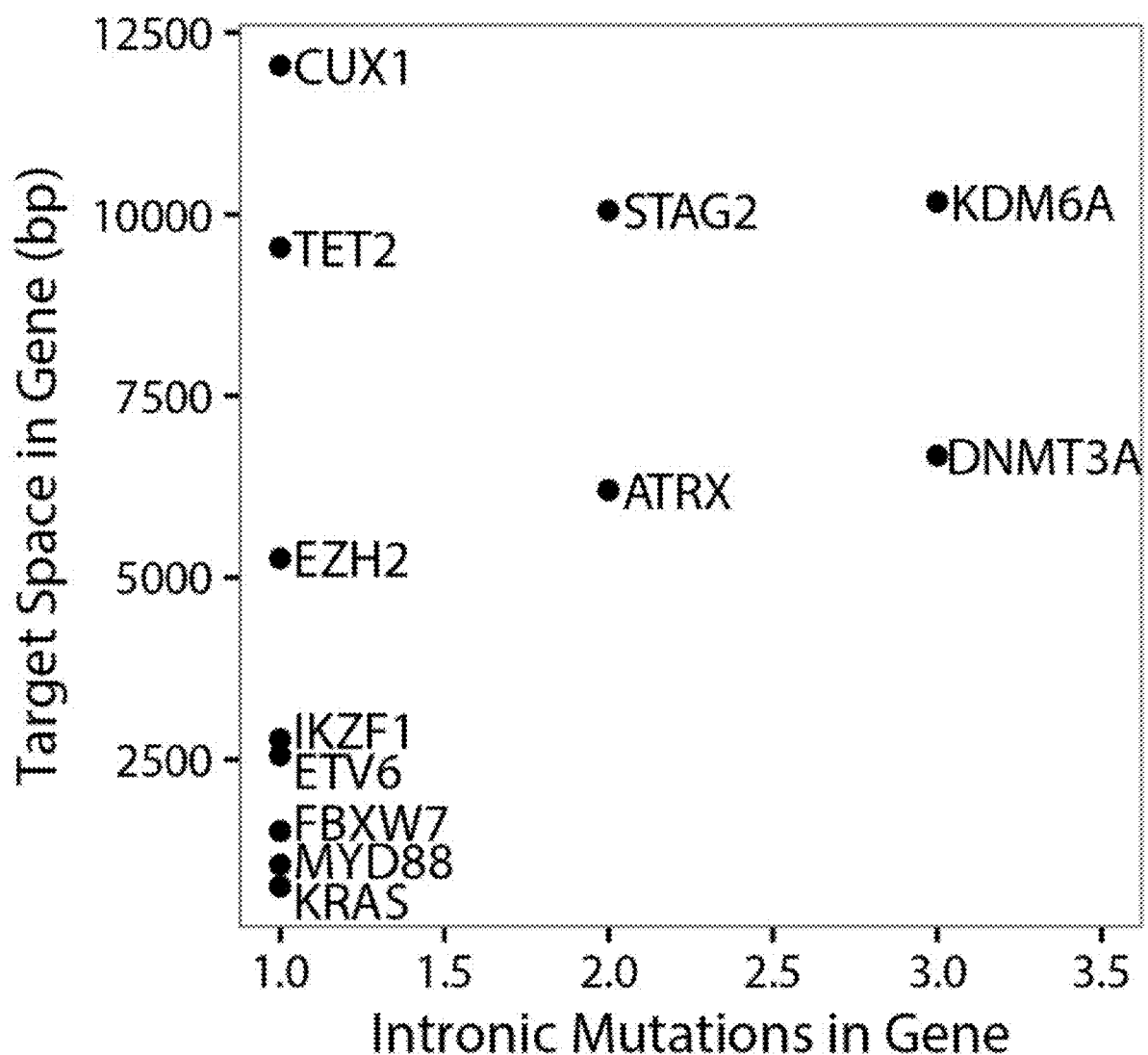
Figure 20:
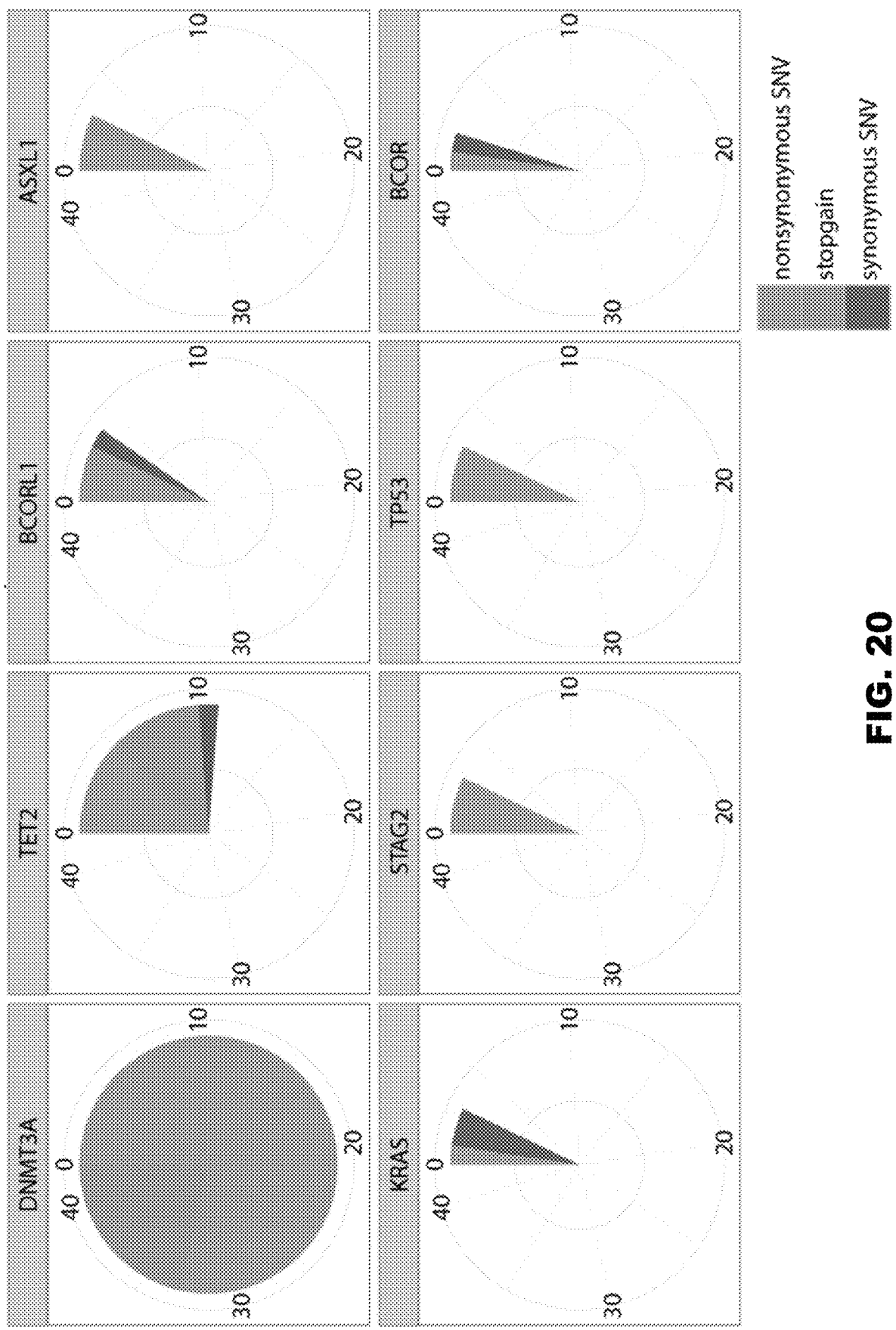
FIG. 20 depicts the distribution of exonic mutations by gene.

Subclonal single nucleotide variations (SNVs) were then called based on the TruSight-ECS libraries generated. A position-specific binomial error model was used to identify rare subclonal SNVs. For each sample, we generated a position specific error profile from all of the sequenced libraries in the study except for samples sequenced from the same individual (the other replicate from the same time point and both replicates from the other time point). Variants were reported if their binomial p-value was less that 0.05 after Bonferroni correction, the variant was observed in at least 5 ECCSs, the VAF was greater than 0.0001, and the variant was identified in at least two replicates from one of the collection time points. The identification of constitutional and rare SNVs in the samples is presented in FIG. 12. Forty-nine germline SNVs were identified (~0.5/1.0 VAF), 5 high VAF were identified (0.14-0.36 VAF) and 106 low VAF were identified (<0.1 VAF) for a total of 160 SNVs detected. Additionally, rare subclones were detected longitudinally in NHS participants (FIG. 13). FIG. 14 presents the total rare subclonal variants detected per individual. The majority of SNVs were present in the exonic regions. The subclonal variants were then classified. As shown in FIG. 15A, the majority of rare variants were present in the exonic regions followed by the intronic regions. Rare variants were occasionally found in ncRNA, splicing region and UTR3. FIG. 15B shows that the vast majority of rare variants were nonsynonymous SNVs. Additionally, detected exonic variants clustered in the DNMT3A and TET2 genes (FIG. 16). The intronic variants, in contrast, were more evenly distributed (FIG. 17). Notably, variants were not exclusively called in highly covered amplicons. FIG. 18A shows the histogram coverage per amplicon and FIG. 18B shows the histogram coverage per amplicon with variants called. It is also important to note that the target space per gene does not correlate with the SNV calls per gene. FIG. 19A shows that the exonic mutations were distributed throughout the target space in the gene and FIG. 19B shows that the intronic mutations were also distributed throughout the target space in the gene. FIG. 20 presents the distribution of exonic mutations by gene which different depending on the gene. For DNMT3A, mutations were only nonsynonymous or stopgain. For TET2 and BCORL1, mutations were nonsynonymous, stopgain and synonymous.

Figure 21:
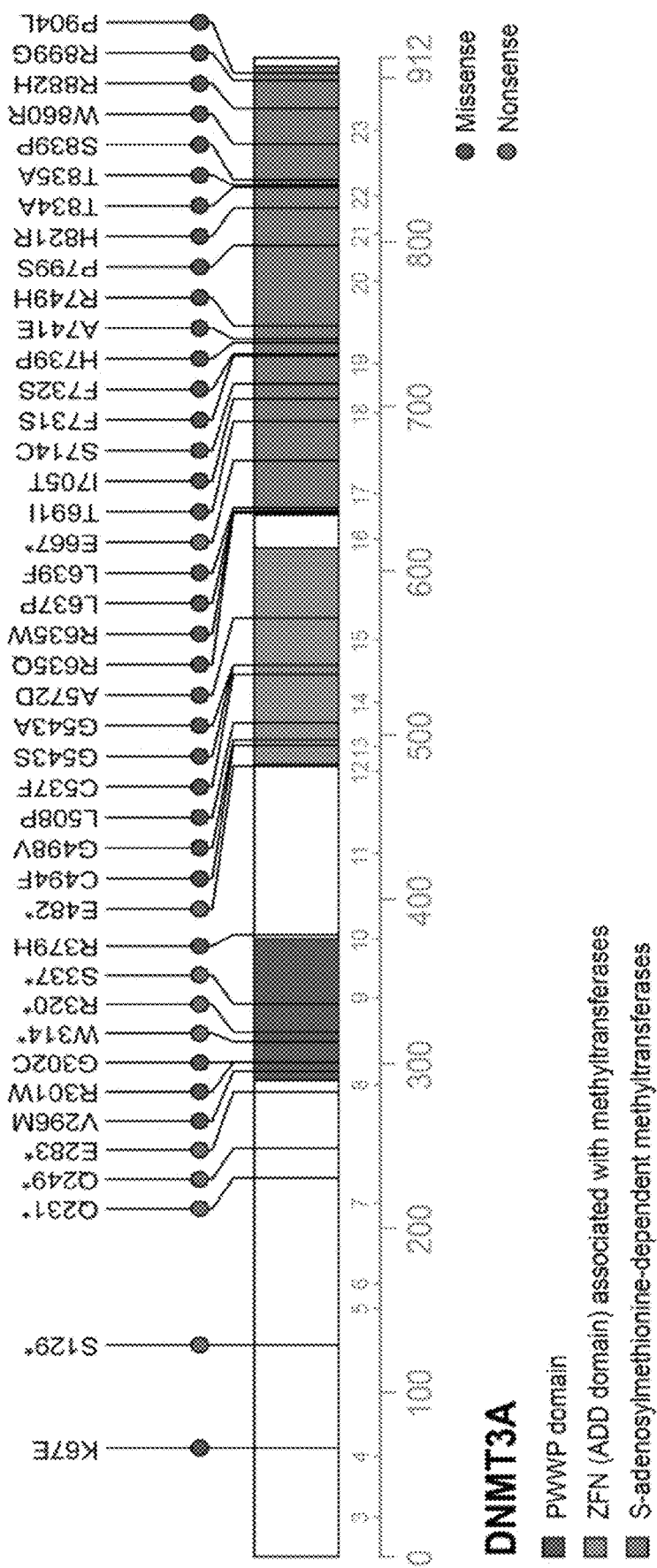
FIG. 21 depicts the spectrum of DNMT3A mutations.
Figure 22:
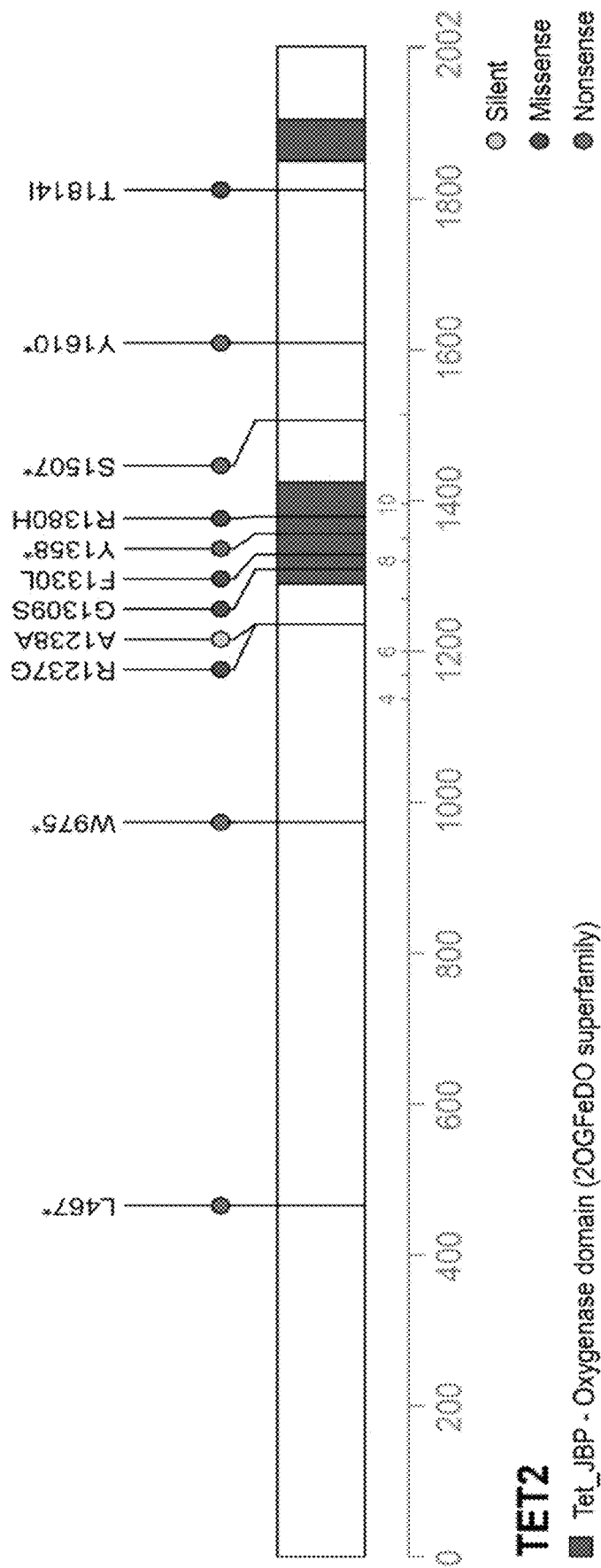
FIG. 22 depicts the spectrum of TET2 mutations.
Figure 23:
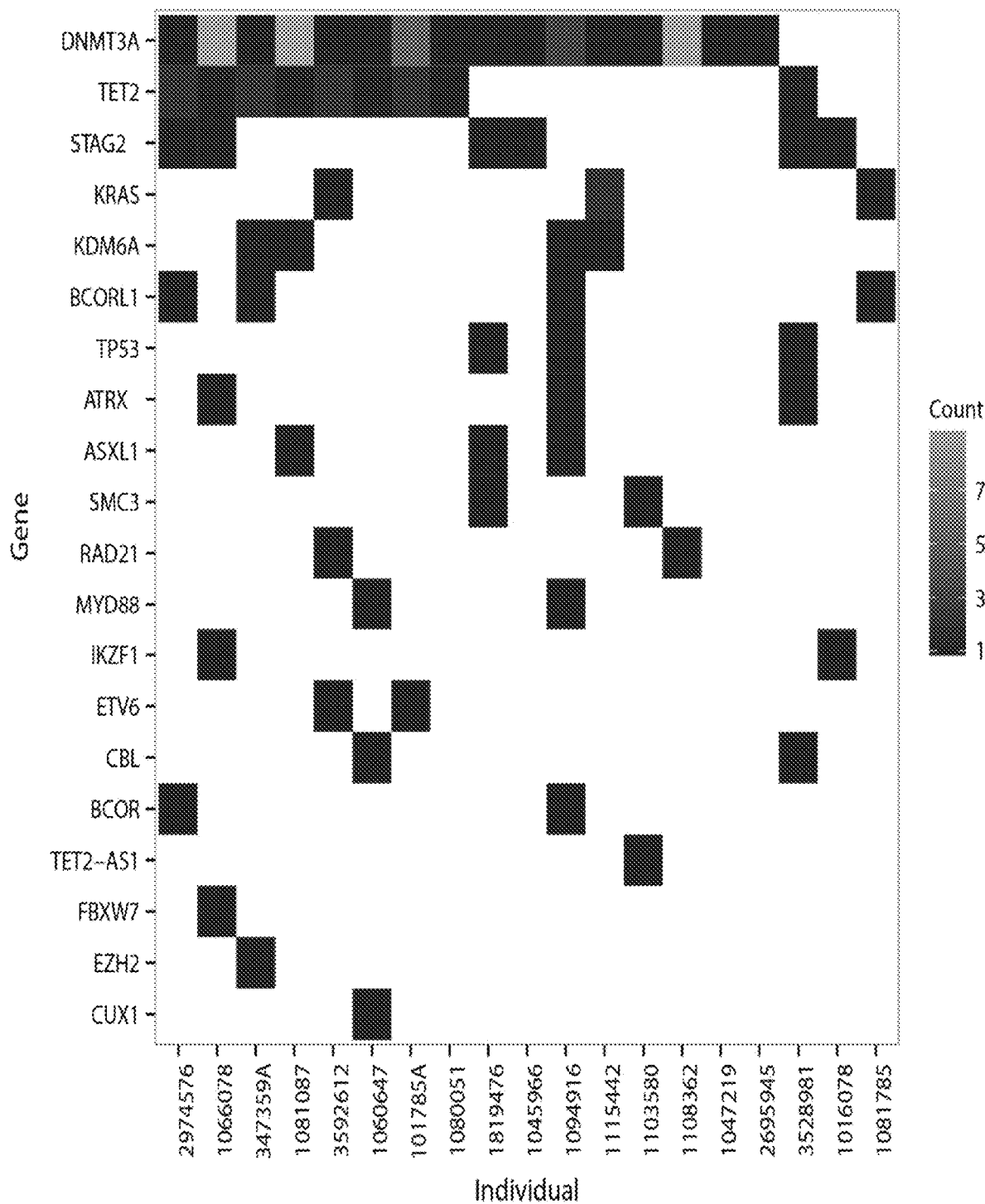
FIG. 23 depicts the distribution of rare subclonal mutations per person.

Given that mutations in DNMT3A and TET2 were the most prevalent mutations, we analyzed where each of the mutations was found on these two genes. Mapping out the spectrum of DNMT3A mutations shows the prevalence of early truncating mutations and the numerous missense mutations in the ZFN and methyltransferase domains (FIG. 21). Mapping out the spectrum of TET2 mutations shows several mutation in the oxygenase domain (FIG. 22). We then evaluated the distribution of rare subclonal mutations per person (FIG. 23). While the majority of individuals have mutations in DNMT3A, mutations in other genes were also detected in combination with the DNMT3A mutation.

In summary, we found that rare subclones harboring mutations in leukemia-associated genes are common in healthy individual (19/20 individuals). We also found that subclones frequently harbor mutations in DNMT3A (but not R882) and TET2. Additionally, since the samples were taken about 10 years apart, we found that subclones are stable over time. Notably, the detection of subclones is not likely due to coverage or target-space bias.

Example 4. VAF Measured with ECS Correlates with VAF Measured with ddPCR

Figure 24:
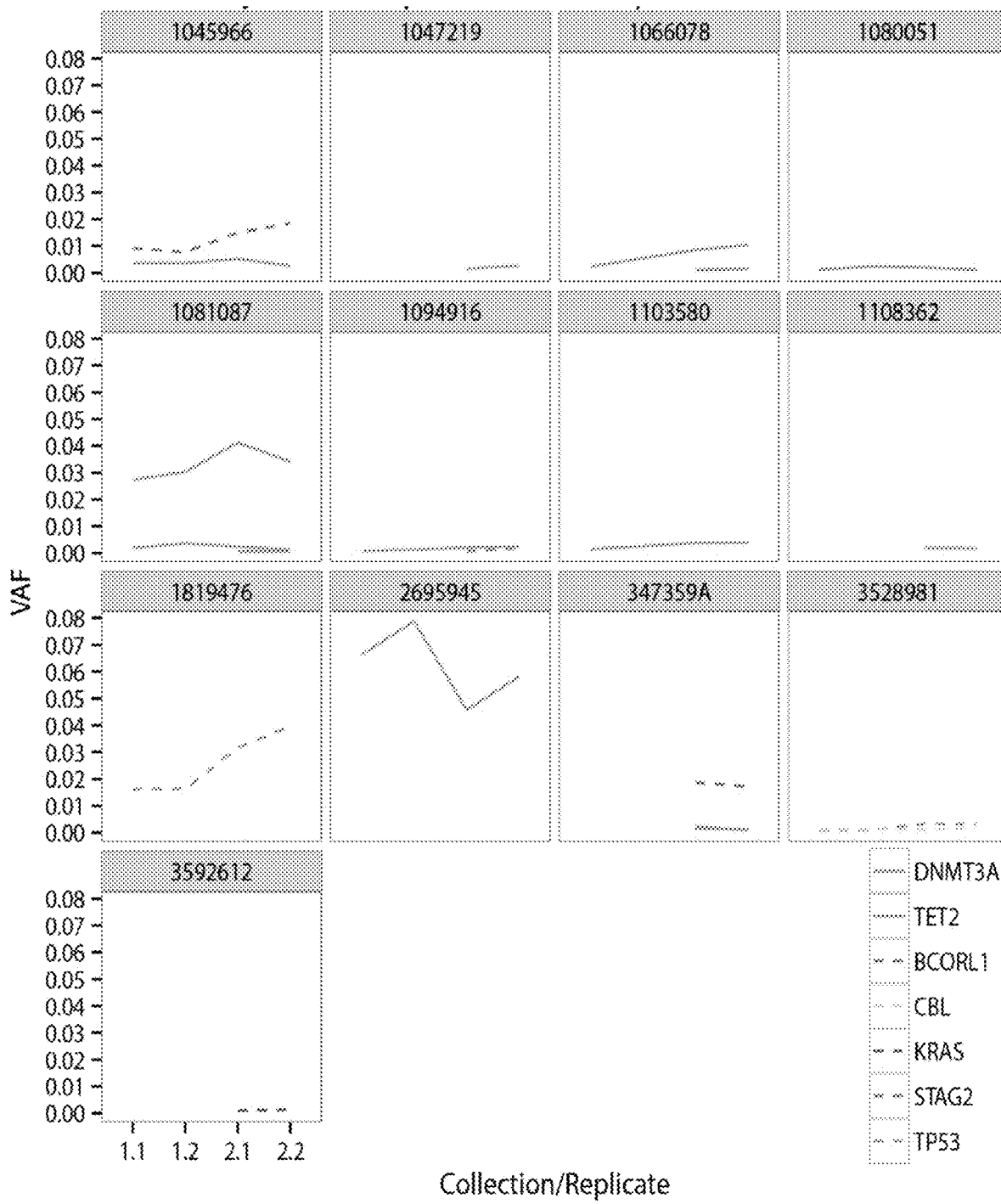
FIG. 24 depicts the COSMIC variants analyzed to validate the ECS methodology disclosed herein with ddPCR.
Figure 25A:
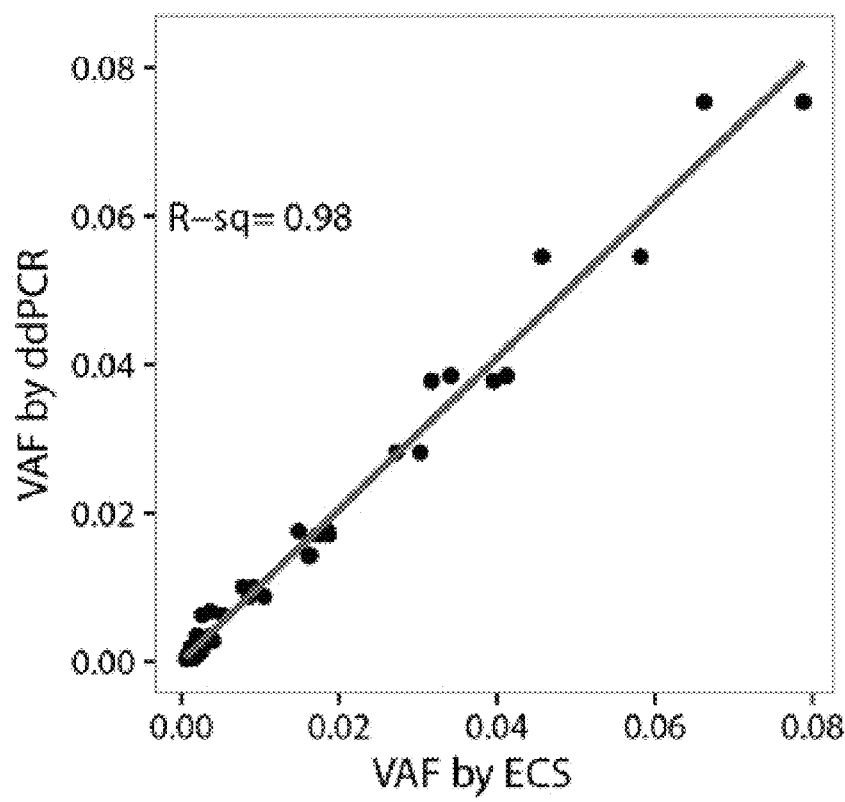
FIGS. 25A and 25B depict the concordance of VAF measured by ECS and ddPCR.
Figure 25B:
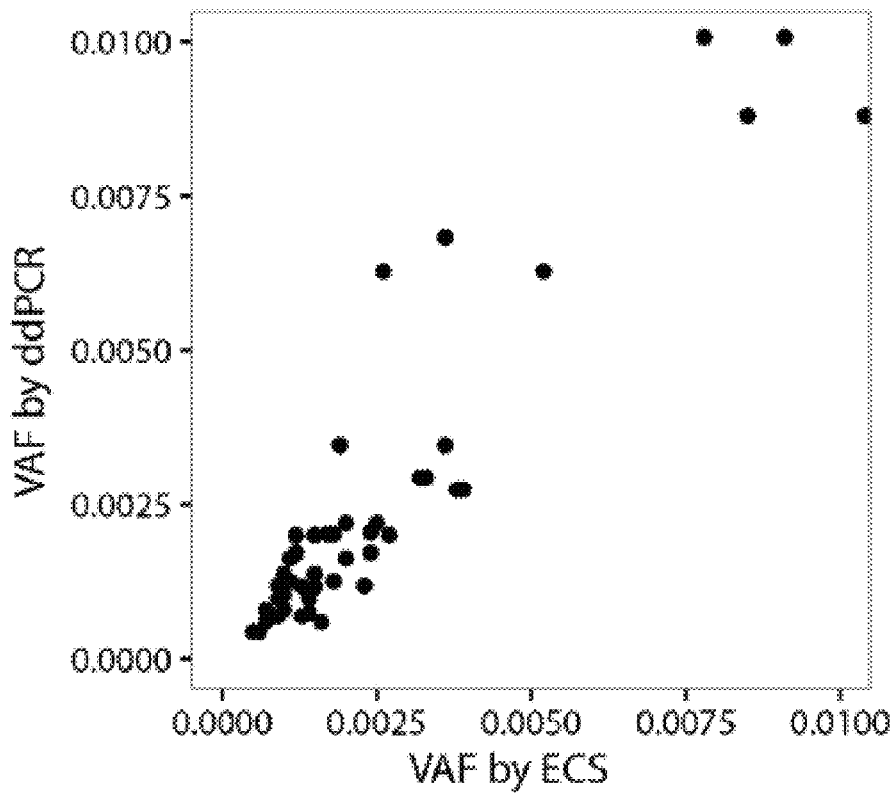

We next sought to validate the COSMIC (Catalogue of Somatic Mutation in Cancer) variants detected using ddPCR (FIG. 24). In the digital droplet validation method, 21 probes and 150,000 to 450,000 droplets per sample or control were used. We found that VAF measured by ECS is highly correlated with VAF measured by ddPCR ($R^2=0.98$) (FIG. 25A). When focusing on the VAF of <0.01, the VAF measured by ECF still correlated with the VAF measured by ddPCR ($R^2=0.72$) (FIG. 25B).

Figure 26:
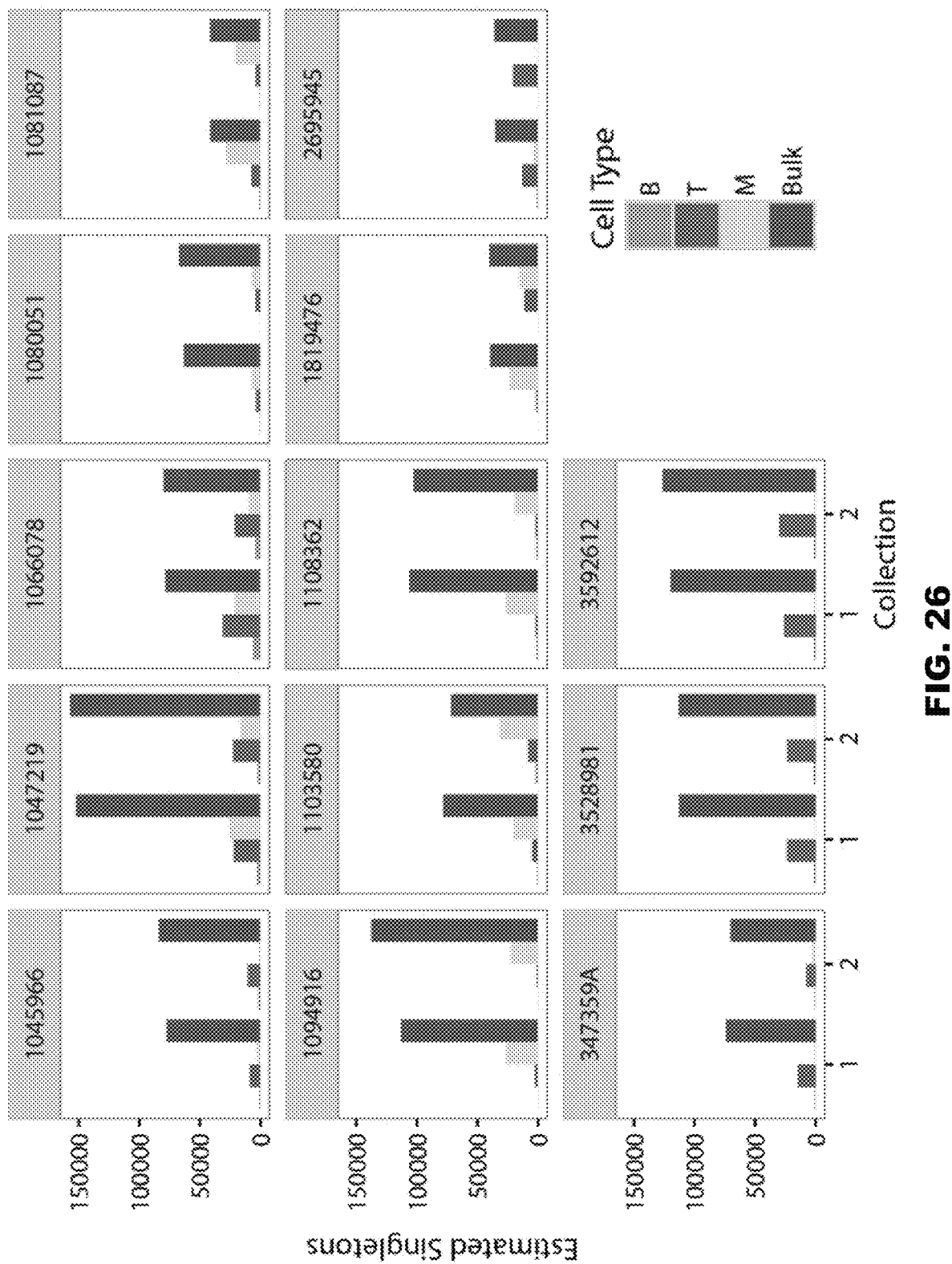
FIG. 26 depicts the number of singleton ddPCR droplets generated by flow sorting cells from the study participants and extracting genomic DNA from those flow sorted cells.
Figure 27:
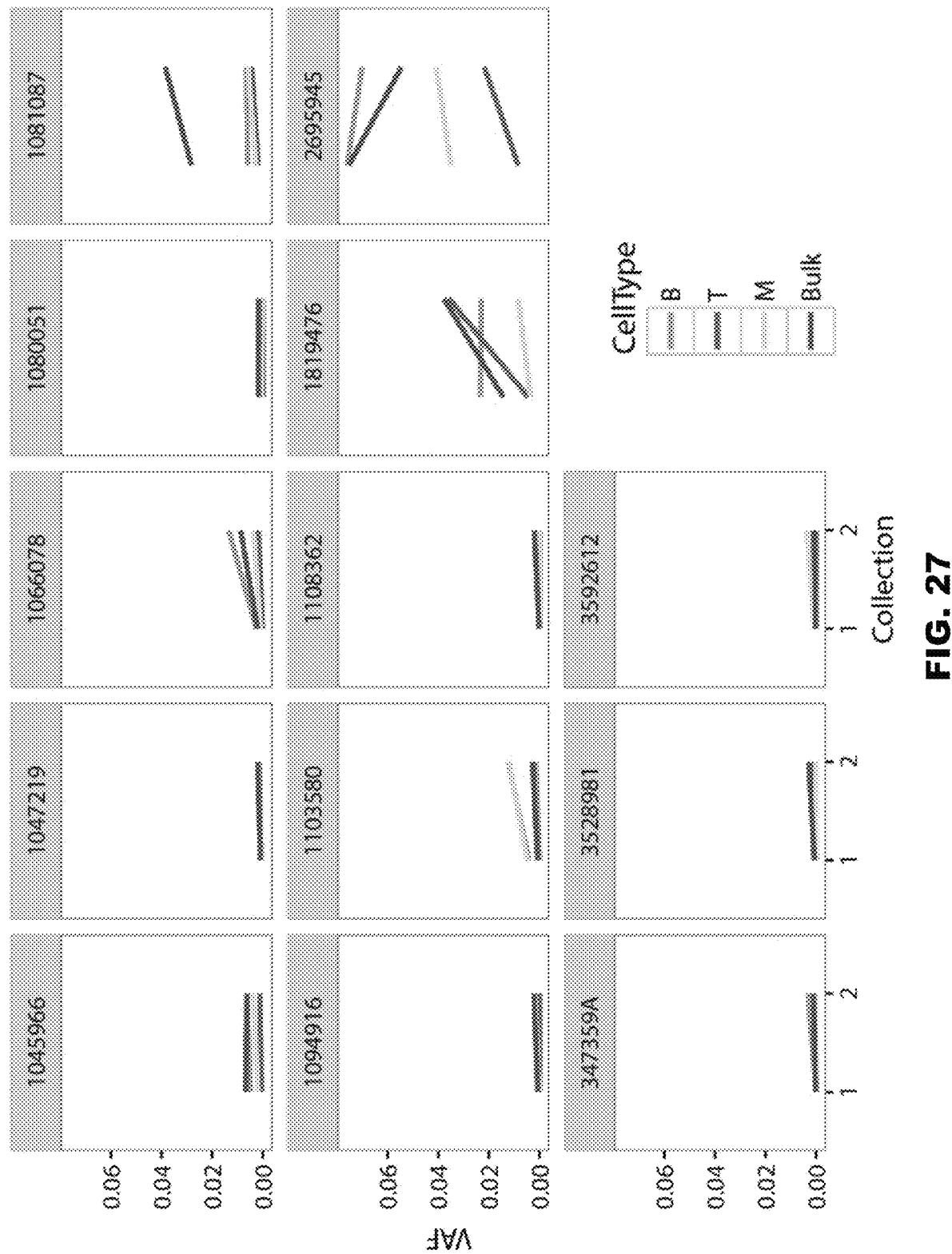
FIG. 27 depicts graphs showing that sublconal mutations are present in multiple lineages in all tested samples.
Figure 28:
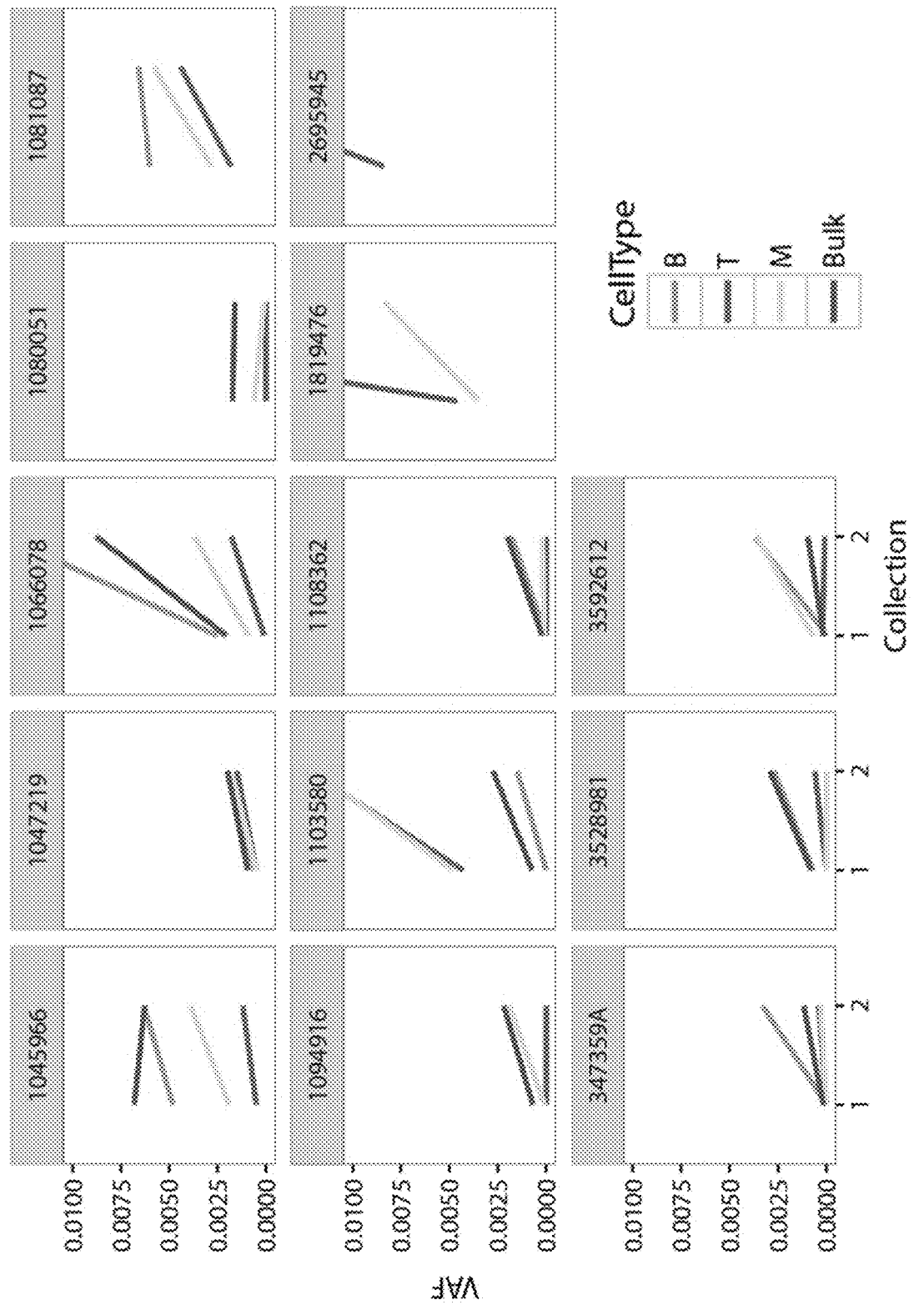
FIG. 28 depicts graphs showing and expanded view of FIG. 27 focusing on a VAF of <0.01.

We then sought to identify the subclones found in various cells types. Accordingly, subclone identification using ddPCR was performed on flow sorted buffy coat samples. Samples were selected from 13 individuals and then pan-leukocyte, myeloid, B-cells and T-cells were sorted. The sorting conditions included the following: pan-leukocyte: BV421 anti-CD45; myeloid: APC anti-CD33; B-cells: FITC anti-CD19; and T-cells: PE-CY7 anti-CD3. Enough DNA was extracted from the sorted samples to perform ddPCR without amplification, however variability in flow yield was detected (FIG. 26). We found that subclonal mutations are present in multiple cellular lineages in all tested samples (FIG. 27). These results are more apparent when focusing specifically on a VAF of <0.01 (FIG. 28).

In summary, we showed that there is a high concordance between VAF measured with ECS and VAF measured with ddPCR. Additionally, we demonstrated that subclonal mutations are present in distinct hematopoietic lineages. It was also demonstrated that subclone identification is improved with indel calling.

What is claimed is:

1. A method of identifying a genetic mutation in a biological sample comprising a nucleic acid obtained from a subject, the method comprising:
   a) forming a hybridization complex by hybridizing a primer pool comprising one or more primer pairs specific complementary to one or more regions of interest of the nucleic acid from the biological sample, producing an extension product by extending from an upstream primer of the primer pairs on the hybridization complex to a downstream primer of the primer pairs on the hybridization complex, and generating a ligation product by ligating the extension product to the downstream primer of the primer pairs, wherein the ligation product comprises the regions of interest flanked by sequences required for amplification;
   b) producing an attaching product by attaching an adapter comprising a random component and an adapter comprising an index sequence to the ligation product from step a) and generating an amplification product by amplifying the attaching product;
   c) sequencing the amplification product in step b), wherein redundant reads are generated by the sequencing of the amplification product and wherein the redundant reads are grouped by the random component, thereby identifying a consensus sequence from the nucleic acid; and
   d) comparing the consensus sequence from the nucleic acid to a wild-type reference sequence from the same species of the subject and identifying the genetic mutation in the biological sample if the consensus sequence differs from the reference sequence.

2. The method of claim 1, wherein the biological sample comprises about 400 to about 800 ng nucleic acid.

3. The method of claim 1, wherein the primer pairs of the primer pool in step a) are specific complementary to more than 500 regions of interest in the nucleic acid and the more than 500 regions of interest in the amplification product are sequenced.

4. The method of claim 1, wherein unbound primers of the primer pool in step a) are washed away prior to step (b).

5. The method of claim 1, wherein each of the adapter comprising a random component and the adapter comprising an index sequence is a Y-shaped adapter.

6. The method of claim 1, wherein the adapter comprising a random component and the adaptor comprising an index sequence are attached to the ligation product from step a) via PCR.

7. The method of claim 1, wherein the genetic mutation identified in step d) are clinical silent single-nucleotide variations (SNVs).

* * * * *

SEQUENCE LISTING

```
<160> NUMBER OF SEQ ID NOS: 36

<210> SEQ ID NO 1
<211> LENGTH: 66
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (17)..(32)
<223> OTHER INFORMATION: n is a, c, g, or t

<400> SEQUENCE: 1
agacggcata cgagatnnnn nnnnnnnnnn nngtgactgg agttcagacg tgtgctcttc    60
cgatct                                                              66
```

<210> SEQ ID NO 2
<211> LENGTH: 57
<212> TYPE: DNA
<213> ORGANISM: Artificial Sequence
<220> FEATURE:
<223> OTHER INFORMATION: SYNTHESIZED

<400> SEQUENCE: 2
gatcggaaga gcgtcgtgta gggaaagagt gtagatctcg gtggtcgccg tatcatt    57

<210> SEQ ID NO 3
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 3
ggagcctctg accctgcatc cctcc    25

<210> SEQ ID NO 4
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 4
cccgcctcac agctgtactc cccag    25

<210> SEQ ID NO 5
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 5
agacctcagg cggctcatag ggcac    25

<210> SEQ ID NO 6
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 6
ggggctggag agacgacagg gctg    24

<210> SEQ ID NO 7
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 7
tcactagaat tttgaaatgt gggtttgttg cc    32

<210> SEQ ID NO 8
<211> LENGTH: 26
<212> TYPE: DNA
<213> ORGANISM: Artificial Sequence
<220> FEATURE:

<223> OTHER INFORMATION: SYNTHESIZED

<400> SEQUENCE: 8
gcactctggt cactgtgatg gctggc                                              26

<210> SEQ ID NO 9
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 9
ggcgatgttg aatgcatgtt ccagt                                               25

<210> SEQ ID NO 10
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 10
aggactatgg gcattggttg tcaat                                               25

<210> SEQ ID NO 11
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 11
ggaccctcgc agacattaaa gcccgt                                              26

<210> SEQ ID NO 12
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 12
gcctcaccac catcaccact gctgc                                               25

<210> SEQ ID NO 13
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 13
ccacaggtgc catgtgtcca gccag                                               25

<210> SEQ ID NO 14
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 14
ctgtggcggg gtgggaggaa tgttg                                               25

```
<210> SEQ ID NO 15
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 15
tgaacacaaa tggaaaatac aactacgaga gaaaa                                35

<210> SEQ ID NO 16
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 16
cccagcaaaa taatcagctc tcattttccc                                      30

<210> SEQ ID NO 17
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 17
cactatgaag gatcctgtaa atgtgacccc                                      30

<210> SEQ ID NO 18
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 18
tggtttgggc tgtttcacta cctca                                           25

<210> SEQ ID NO 19
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 19
ccacgtgggg actcactcag gca                                             23

<210> SEQ ID NO 20
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 20
aataagacgg tctctgtgcc tcctg                                           25

<210> SEQ ID NO 21
<211> LENGTH: 23
<212> TYPE: DNA
<213> ORGANISM: Artificial Sequence
<220> FEATURE:
<223> OTHER INFORMATION: SYNTHESIZED
```

<400> SEQUENCE: 21
tggtacacgc cttcatcctc ggg					23

<210> SEQ ID NO 22
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 22
gctcagctct gtccctgccc agct					24

<210> SEQ ID NO 23
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 23
accctggtgt ctgtggcatt ctctg					25

<210> SEQ ID NO 24
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 24
agtcacagca tcattcctct tgcggt					26

<210> SEQ ID NO 25
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 25
caaatgcgcg gctcctttaa ccgga					25

<210> SEQ ID NO 26
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 26
gcgtggctga gcgggtgtcc					20

<210> SEQ ID NO 27
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 27
taccacattc gggactggga actgc					25

<210> SEQ ID NO 28
<211> LENGTH: 23

<212> TYPE: DNA
<213> ORGANISM: Artificial Sequence
<220> FEATURE:
<223> OTHER INFORMATION: SYNTHESIZED

<400> SEQUENCE: 28
ctcccagggt cccggcgaac tcc                                       23

<210> SEQ ID NO 29
<211> LENGTH: 28
<212> TYPE: DNA
<213> ORGANISM: Artificial Sequence
<220> FEATURE:
<223> OTHER INFORMATION: SYNTHESIZED

<400> SEQUENCE: 29
tggcaatcac ccaaaccaaa gcatcggt                                  28

<210> SEQ ID NO 30
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 30
aacccagatc acctcggagc aggcg                                     25

<210> SEQ ID NO 31
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 31
ggggacacag ttcgcagggg tc                                        22

<210> SEQ ID NO 32
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 32
gactggggtg cgggaggtca cagg                                      24

<210> SEQ ID NO 33
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 33
ggcgtgcctg ccaatggtga tggg                                      24

<210> SEQ ID NO 34
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 34

```
ccgtctggct gtgttgttgc ttgggg                                            26

<210> SEQ ID NO 35
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 35
acatggtccc tgagtatacc agcct                                             25

<210> SEQ ID NO 36
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 36
ggccaccaac ctcattctgt tttgt                                             25
```